US011011711B2

(12) United States Patent
Kim et al.

(10) Patent No.: US 11,011,711 B2
(45) Date of Patent: May 18, 2021

(54) ORGANOMETALLIC COMPOUND, ORGANIC LIGHT-EMITTING DEVICE INCLUDING THE ORGANOMETALLIC COMPOUND, AND DIAGNOSIS COMPOSITION INCLUIDNG THE ORGANOMETALLIC COMPOUND

(71) Applicant: SAMSUNG ELECTRONICS CO., LTD., Suwon-si (KR)

(72) Inventors: Soyeon Kim, Seoul (KR); Yoonhyun Kwak, Seoul (KR); Ohyun Kwon, Seoul (KR); Hyeonho Choi, Seoul (KR); Hyun Koo, Seoul (KR); Youngjae Park, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 505 days.

(21) Appl. No.: 15/424,390

(22) Filed: Feb. 3, 2017

(65) Prior Publication Data

US 2017/0237023 A1 Aug. 17, 2017

(30) Foreign Application Priority Data

Feb. 11, 2016 (KR) .......................... 10-2016-0015678

(51) Int. Cl.
| | | |
|---|---|---|
| *H01L 51/00* | (2006.01) | |
| *G01N 33/52* | (2006.01) | |
| *A61K 49/00* | (2006.01) | |
| *C07F 15/00* | (2006.01) | |
| *C09K 11/02* | (2006.01) | |

(Continued)

(52) U.S. Cl.
CPC ...... *H01L 51/0087* (2013.01); *A61K 49/0015* (2013.01); *C07F 15/0086* (2013.01);
(Continued)

(58) Field of Classification Search
None
See application file for complete search history.

(56) References Cited

U.S. PATENT DOCUMENTS 7,732,606 B2  6/2010 Ise et al.
2005/0137459 A1  6/2005 Chin et al.
(Continued)

FOREIGN PATENT DOCUMENTS

EP         2891659 A2    7/2015
KR   10-2016-0037007 A  4/2016
WO      2005058149 A1   6/2005

OTHER PUBLICATIONS

Extended Search Report dated Jul. 18, 2017, issued by the European Patent Office for EP Patent Application No. 17155485.0-1451.

(Continued)

*Primary Examiner* — Jay Yang
(74) *Attorney, Agent, or Firm* — Cantor Colburn LLP

(57) ABSTRACT

An organometallic compound represented by Formula 1:

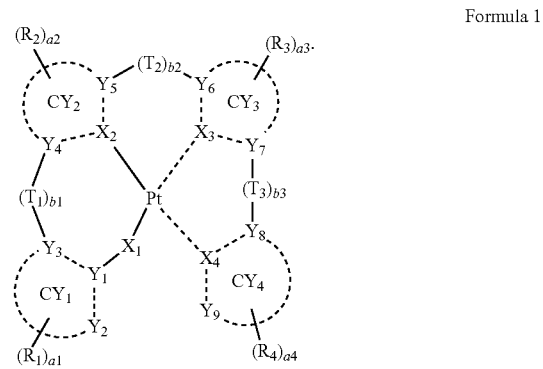

wherein in Formula 1, groups and variables are the same as described in the specification.

11 Claims, 1 Drawing Sheet

(51) Int. Cl.
 C09K 11/06 (2006.01)
 H05B 33/14 (2006.01)
 C09K 11/00 (2006.01)
 H01L 51/50 (2006.01)
(52) U.S. Cl.
 CPC ............ *C09K 11/00* (2013.01); *C09K 11/025* (2013.01); *C09K 11/06* (2013.01); *G01N 33/52* (2013.01); *H01L 51/0072* (2013.01); *H05B 33/14* (2013.01); *C09K 2211/1007* (2013.01); *C09K 2211/1011* (2013.01); *C09K 2211/1022* (2013.01); *C09K 2211/1029* (2013.01); *C09K 2211/185* (2013.01); *H01L 51/5012* (2013.01); *H01L 51/5016* (2013.01)

(56) References Cited

U.S. PATENT DOCUMENTS

| | | | | |
|---|---|---|---|---|
| 2005/0227112 | A1* | 10/2005 | Ise et al. | C09K 11/06 428/690 |
| 2006/0060842 | A1* | 3/2006 | Sano et al. | C09K 11/06 257/40 |
| 2007/0103060 | A1* | 5/2007 | Itoh et al. | C07D 213/06 313/504 |
| 2013/0274473 | A1 | 10/2013 | Che et al. | |
| 2015/0287937 | A1 | 10/2015 | Che et al. | |
| 2015/0303384 | A1 | 10/2015 | Kim et al. | |
| 2017/0012226 | A1 | 1/2017 | Hwang et al. | |

OTHER PUBLICATIONS

English Translation of Office Action issued by the Chinese Patent Office dated Jun. 17, 2020 in the examination of the Chinese Patent Application No. 201710066097.X, which corresponds to the U.S. Application above.

Office Action issued by the Chinese Patent Office dated Jun. 17, 2020 in the examination of the Chinese Patent Application No. 201710066097.X, which corresponds to the U.S. Application above.

* cited by examiner

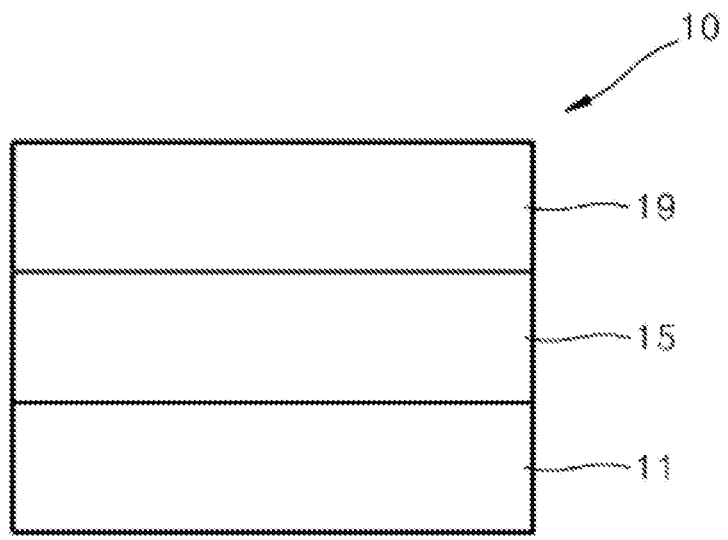

ORGANOMETALLIC COMPOUND, ORGANIC LIGHT-EMITTING DEVICE INCLUDING THE ORGANOMETALLIC COMPOUND, AND DIAGNOSIS COMPOSITION INCLUIDNG THE ORGANOMETALLIC COMPOUND

CROSS-REFERENCE TO RELATED APPLICATION

This application claims priority to Korean Patent Application No. 10-2016-0015678, filed on Feb. 11, 2016, in the Korean Intellectual Property Office, and all the benefits accruing therefrom under 35 U.S.C. § 119, the content of which is incorporated herein in its entirety by reference.

BACKGROUND

1. Field

One or more embodiments relate to an organometallic compound, an organic light-emitting device including the organometallic compound, and a diagnosis composition including the organometallic compound.

2. Description of the Related Art

Organic light-emitting devices (OLEDs) are self-emission devices that have wide viewing angles, and short response times. OLEDs also exhibit excellent brightness, driving voltage, and response speed characteristics, and produce full-color images.

In an example, an organic light-emitting device includes an anode, a cathode, and an organic layer that is disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons transition from an excited state to a ground state, thereby generating light.

Luminescent compounds, for example, phosphorescent luminescent compounds may be used to monitor, sense, or detect biological materials, such as cells or proteins.

Various types of organic light emitting devices are known. However, there still remains a need in OLEDs having low driving voltage, high efficiency, high brightness, and long lifespan.

SUMMARY

One or more embodiments include a novel organometallic compound, an organic light-emitting device including the novel organometallic compound, and a diagnosis composition including the novel organometallic compound.

Additional aspects will be set forth in part in the description which follows and, in part, will be apparent from the description, or may be learned by practice of the presented embodiments.

According to one or more embodiments, an organometallic compound is represented by Formula 1:

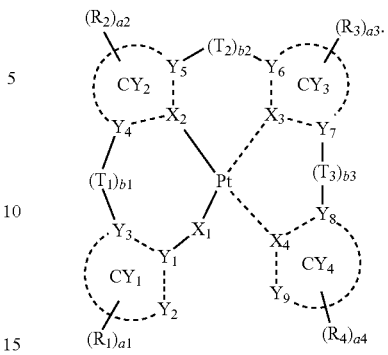

Formula 1

In Formula 1,
$X_1$ may be O or S,
$X_2$ may be C, and
$X_3$ and $X_4$ may be N,
A bond between Pt and $X_1$ and a bond between Pt and $X_2$ may be a covalent bond, and a bond between Pt and $X_3$ and a bond between Pt and $X_4$ may be a coordinate bond,
$Y_1$ and $Y_3$ to $Y_8$ may each independently be C or N,
$Y_2$ and $Y_9$ may each independently be C, N, O, or S,
$Y_1$ and $Y_2$ may be connected to each other via a single bond or a double bond, $Y_1$ and $Y_3$ may be connected to each other via a single bond or a double bond, $X_2$ and $Y_4$ may be connected to each other via a single bond or a double bond, $X_2$ and $Y_5$ may be connected to each other via a single bond or a double bond, $X_3$ and $Y_6$ may be connected to each other via a single bond or a double bond, $X_3$ and $Y_7$ may be connected to each other via a single bond or a double bond, $X_4$ and $Y_8$ may be connected to each other via a single bond or a double bond, and $X_4$ and $Y_9$ may be connected to each other via a single bond or a double bond,
$CY_1$ to $CY_4$ may each independently be selected from a $C_5$-$C_{30}$ carbocyclic group and a $C_1$-$C_{30}$ heterocyclic group,
$T_1$ and $T_2$ may each be a group independently be selected from a single bond, *—O—*', *—S—*', *—C($R_5$)($R_6$)—*', *—C($R_5$)=*', *=O($R_5$)—*', *—C($R_5$)=C($R_6$)—*', *—C(=O)—*', *—C(=S)—*', *—C≡C—*', *—N($R_5$)—*', *—Si($R_5$)($R_6$)—*', and *—P($R_5$)($R_6$)—*', wherein * and *' in each of the foregoing groups independently indicate a binding site to a neighboring atom,
$T_3$ may be a group selected from *—O—*', *—S—*', *—C($R_7$)($R_8$)—*', *—C($R_7$)=*', *=C($R_7$)—*', *—C($R_7$)=C($R_8$)—*', *—C(=O)—*', *—C(=S)—*', *—C≡C—*', *—N($R_7$)—*', *—Si($R_7$)($R_8$)—*', and *—P($R_7$)($R_8$)—*', wherein * and *' in each of the foregoing groups independently indicate a binding site to a neighboring atom,
$R_5$ and $R_6$ may be optionally connected to each other via a first linking group to form a substituted or unsubstituted $C_5$-$C_{30}$ carbocyclic group or a substituted or unsubstituted $C_1$-$C_{30}$ heterocyclic group,
$R_7$ and $R_8$ may be optionally connected to each other via a second linking group to form a substituted or unsubstituted $C_5$-$C_{30}$ carbocyclic group or a substituted or unsubstituted $C_1$-$C_{30}$ heterocyclic group,
b1 to b3 may each independently be 1, 2, or 3,
$R_1$ to $R_8$ may each independently be selected from hydrogen, deuterium, —F, —Cl, —Br, —I, —SF$_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), and —P(=O)($Q_8$)($Q_9$), a1 to a4 may each independently be 0, 1, 2, 3, 4, or 5, two groups selected from groups $R_1$ in the number of a1 may be optionally connected to each other to form a substituted or unsubstituted $C_5$-$C_{30}$ carbocyclic group or a substituted or unsubstituted $C_1$-$C_{30}$ heterocyclic group, two groups selected from groups $R_2$ in the number of a2 may be optionally connected to each other to form a substituted or unsubstituted $C_5$-$C_{30}$ carbocyclic group or a substituted or unsubstituted $C_1$-$C_{30}$ heterocyclic group, two groups selected from groups $R_3$ in the number of a3 may be optionally connected to each other to form a substituted or unsubstituted $C_5$-$C_{30}$ carbocyclic group or a substituted or unsubstituted $C_1$-$C_{30}$ heterocyclic group, two groups selected from groups $R_4$ in the number of a4 may be optionally connected to each other to form a substituted or unsubstituted $C_5$-$C_{30}$ carbocyclic group or a substituted or unsubstituted $C_1$-$C_{30}$ heterocyclic group, two or more neighboring groups selected from $R_1$ to $R_4$ may be optionally connected to each other to form a substituted or unsubstituted $C_5$-$C_{30}$ carbocyclic group or a substituted or unsubstituted $C_1$-$C_{30}$ heterocyclic group, at least one substituent selected from a substituent(s) of the substituted $C_5$-$C_{30}$ carbocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted heterocycloalkyl group, the substituted $C_3$-$C_{10}$ cycloalkenyl group, the substituted heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —P(=O)($Q_{18}$)($Q_{19}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), wherein $Q_1$ to $Q_9$, $Q_{11}$ to $Q_{19}$, $Q_{21}$ to $Q_{29}$, and $Q_{31}$ to $Q_{39}$ may each independently be selected from hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

According to one or more embodiments, an organic light-emitting device includes:

a first electrode;

a second electrode; and an organic layer disposed between the first electrode and the second electrode, wherein the organic layer including an emission layer, and wherein the organic layer includes at least one organometallic compound described above.

The organometallic compound in the emission layer may act as a dopant.

According to one or more embodiments, a diagnosis composition includes at least one organometallic compound represented by Formula 1.

BRIEF DESCRIPTION OF THE DRAWING

These and/or other aspects will become apparent and more readily appreciated from the following description of the embodiments, taken in conjunction with FIGURE which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

An organometallic compound according to an embodiment may be represented by Formula 1:

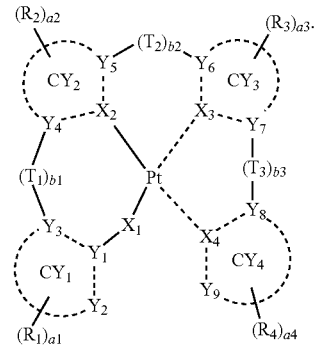

Formula 1

$X_1$ in Formula 1 may be O or S. For example, $X_1$ may be O, but is not limited thereto.

In Formula 1, $X_2$ may be C, and $X_3$ and $X_4$ may be N.

In Formula 1, a bond between Pt and $X_1$ and a bond between Pt and $X_2$ may be a covalent bond, and a bond between Pt and $X_3$ and a bond between Pt and $X_4$ may be a coordinate bond.

In Formula 1, $Y_1$ and $Y_3$ to $Y_8$ may each independently be C or N, and $Y_2$ and $Y_9$ may each independently be C, N, O, or S.

In one or more embodiments, in Formula 1, $X_1$ may be 0, and $Y_1$ and $Y_3$ to $Y_8$ may be C, but embodiments are not limited thereto.

In Formula 1, $Y_1$ and $Y_2$ may be connected to each other via a single bond or a double bond, $Y_1$ and $Y_3$ may be connected to each other via a single bond or a double bond, $X_2$ and $Y_4$ may be connected to each other via a single bond or a double bond, $X_2$ and $Y_5$ may be connected to each other via a single bond or a double bond, $X_3$ and $Y_6$ may be connected to each other via a single bond or a double bond, $X_3$ and $Y_7$ may be connected to each other via a single bond or a double bond, $X_4$ and $Y_9$ may be connected to each other via a single bond or a double bond, and $X_4$ and $Y_9$ may be connected to each other via a single bond or a double bond.

$CY_1$ to $CY_4$ in Formula 1 may each independently be selected from a $C_5$-$C_{30}$ carbocyclic group and a $C_1$-$C_{30}$ heterocyclic group.

For example, $CY_1$ and $CY_2$ in Formula 1 may each independently be selected from a benzene group, a naphthalene group, an anthracene group, a phenanthrene group, a triphenylene group, a pyrene group, a chrysene group, a cyclopentadiene group, an indene group, a fluorene group, a pyrrole group, an indole group, a carbazole group, a furan group, a benzofuran group, a dibenzofuran group, a thiophene group, a benzothiophene group, a dibenzothiophene group, a pyridine group, a pyrimidine group, and a 1,2,3,4-tetrahydronaphthalene group.

In one or more embodiments, $CY_3$ and $CY_4$ in Formula 1 may each independently be selected from a pyridine group, a pyrimidine group, a pyrazine group, a pyridazine group, a triazine group, a quinoline group, an isoquinoline group, a quinoxaline group, a quinazoline group, a phenanthroline group, a pyrazole group, an imidazole group, a triazole group, an oxazole group, an iso-oxazole group, a thiazole group, an isothiazole group, an oxadiazole group, a thiadiazole group, a benzopyrazole group, a benzoimidazole group, a benzoxazole group, a benzothiazole group, a benzooxadiazole group, a benzothiadiazole group, a 5,6,7,8-tetrahydroisoquinoline group, and a 5,6,7,8-tetrahydroquinoline group.

In one or more embodiments, in Formula 1, $CY_1$ and $CY_2$ may each independently be a benzene group, a naphthalene group, a fluorene group, a dibenzofuran group, or a dibenzothiophene group, and $CY_3$ and $CY_4$ may each independently be a pyridine group, a pyrimidine group, a quinoline group, an isoquinoline group, a quinoxaline group, a quinazoline group, a 5,6,7,8-tetrahydroisoquinoline group, or a 5,6,7,8-tetrahydroquinoline group.

In one or more embodiments, in Formula 1, $CY_1$ and $CY_2$ may be a benzene group, and $CY_3$ and $CY_4$ may be a pyridine group;

$CY_1$ may be a benzene group, $CY_2$ may be a naphthalene group, a dibenzofuran group, or a dibenzothiophene group, and $CY_3$ and $CY_4$ may be a pyridine group;

$CY_1$ may be a naphthalene group, a dibenzofuran group, or a dibenzothiophene group, $CY_2$ may be a benzene group, and $CY_3$ and $CY_4$ may be a pyridine group;

$CY_1$ may be a dibenzofuran group or a dibenzothiophene group, $CY_2$ may be a naphthalene group, and $CY_3$ and $CY_4$ may be a pyridine group;

$CY_1$ and $CY_2$ may be a benzene group, $CY_3$ may be a quinoline group, an isoquinoline group, a 5,6,7,8-tetrahydroisoquinoline group, or a 5,6,7,8-tetrahydroquinoline group, and $CY_4$ may be a pyridine group;

$CY_1$ may be a benzene group, $CY_2$ may be a naphthalene group, $CY_3$ may be a quinoline group, an isoquinoline group, a 5,6,7,8-tetrahydroisoquinoline group, or a 5,6,7,8-tetrahydroquinoline group, and $CY_4$ may be a pyridine group; or $CY_1$ and $CY_2$ may be a benzene group, $CY_3$ may be a pyridine group, $CY_4$ may be a quinoline group, an isoquinoline group, a 5,6,7,8-tetrahydroisoquinoline group, or a 5,6,7,8-tetrahydroquinoline group, but embodiments are not limited thereto.

In Formula 1, $T_1$ and $T_2$ may each be a group independently selected from a single bond, *—O—*', *—S—*', *—C($R_5$)($R_6$)—*', *—C($R_5$)=*', *=C($R_5$)—*', *—C($R_5$)=C($R_6$)—*', *—C(=O)—*', *—C(=S)—*', *—C≡C—*', *—N($R_5$)—*', *—Si($R_5$)($R_6$)—*', wherein * and *' in each of the foregoing groups independently indicate a binding site to a neighboring atom, and *—P($R_5$)($R_6$)—*', and $T_3$ may be a group selected from *—O—*', *—S—*', *—C($R_7$)($R_8$)—*', *—C($R_7$)=*', *=C($R_7$)—*', *—C($R_7$)=C($R_8$)—*', *—C(=O)—*', *—C(=S)—*', *—C≡C—*', *—N($R_7$)—*', *—Si($R_7$)($R_8$)—*', and *—P($R_7$)($R_8$)—*', wherein * and *' in each of the foregoing groups independently indicate a binding site to a neighboring atom. $R_5$ to $R_8$ are the same as described below.

$R_5$ and $R_6$ may be optionally connected to each other via a first linking group to form a substituted or unsubstituted $C_6$-$C_{30}$ carbocyclic group or a substituted or unsubstituted $C_1$-$C_{30}$ heterocyclic group, and $R_7$ and $R_8$ may be optionally connected to each other via a second linking group to form a substituted or unsubstituted $C_5$-$C_{30}$ carbocyclic group or a substituted or unsubstituted $C_1$-$C_{30}$ heterocyclic group.

The first linking group and the second linking group may each independently be selected from a single bond, *—O—*', *—C($R_9$)($R_{10}$)—*', *—C($R_9$)=*', *=C($R_9$)—*', *—C($R_9$)=C($R_{10}$)—*', *—C(=O)—*', *—C(=S)—*', *—C≡C—*', *—N($R_9$)—*', *—Si($R_9$)($R_{10}$)—*', and *—P($R_9$)($R_{10}$)—*', wherein * and *' in each of the foregoing groups independently indicate a binding site to a neighboring atom, and $R_9$ and $R_{10}$ are each independently the same as described above in connection with $R_7$.

In one or more embodiments, the first linking group and the second linking group may each independently be selected from a single bond, *—O—*', *—S—*', *—C($R_9$)($R_{10}$)—*', *—N($R_9$)—*', *—Si($R_9$)($R_{10}$)—*', and *—P($R_9$)($R_{10}$)—*', wherein * and *' in each of the foregoing groups independently indicate a binding site to a neighboring atom, but are not limited thereto.

b1 in Formula 1 indicates the number of groups $T_1$ and may be 1, 2, or 3. When b1 is 2 or greater, two or more groups $T_1$ may be identical to or different from each other. b2 and b3 may be understood by referring to the description provided in connection with b1 and Formula 1.

b1 to b3 in Formula 1 may each independently be 1, 2, or 3. For example, b1 to b3 in Formula 1 may be 1, but are not limited thereto.

In one or more embodiments, in Formula 1, $T_1$ may be a single bond, $T_2$ may be a group selected from a single bond, *—O—*', *—C($R_5$)($R_6$)—*', *—N($R_5$)—*', *—Si($R_5$)($R_6$)—*', and *—P($R_5$)($R_6$)—*', wherein * and *' in each of the foregoing groups independently indicate a binding site to a neighboring atom, and $T_3$ may be a group selected from *—C($R_7$)($R_5$)—*', *—N($R_7$)—*', *—Si($R_7$)($R_5$)—*', and *—P($R_7$)($R_5$)—*', wherein * and *' in each of the foregoing groups independently indicate a binding site to a neighboring atom, but embodiments are not limited thereto.

In one or more embodiments, in Formula 1, $T_3$ may be a group selected from *—C($R_7$)($R_8$)—*', *—Si($R_7$)($R_8$)—*', and *—P($R_7$)($R_8$)—*', wherein * and *' in each of the foregoing groups independently indicate a binding site to a neighboring atom, b3 may be 1, and $R_7$ and $R_8$ may be connected to each other via a second linking group. The second linking group is the same as described above.

$R_1$ to $R_8$ may each independently be selected from hydrogen, deuterium, —F, —Cl, —Br, —I, —SF$_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), and —P(=O)($Q_8$)($Q_9$).

For example, $R_1$ to $R_8$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —N($Q_1$)($Q_2$), —Si($Q_3$)($Q_4$)($Q_5$), —B($Q_6$)($Q_7$), and —P(=O)($Q_8$)($Q_9$), wherein $Q_1$ to $Q_9$ may each independently be selected from:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

In one or more embodiments, $R_1$ to $R_8$ may each independently be selected from:

hydrogen, deuterium, —F, a cyano group, a nitro group, —SF$_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group; and —$N(Q_1)(Q_2)$, —$Si(Q_3)(Q_4)(Q_5)$, —$B(Q_6)(Q_7)$, and —$P(=O)(Q_5)(Q_9)$, wherein $Q_1$ to $Q_9$ may each independently be selected from:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group, but embodiments are not limited thereto.

In one or more embodiments, $R_1$ to $R_8$ may each independently be selected from hydrogen, deuterium, —F, a cyano group, a nitro group, —$SF_5$, —$CH_3$, —$CD_3$, —$CD_2H$, —$CDH_2$, —$CF_3$, —$CF_2H$, —$CFH_2$, groups represented by Formulae 9-1 to 9-19, groups represented by Formulae 10-1 to 10-46, and —$Si(Q_3)(Q_4)(Q_5)$, but are not limited thereto:

-continued
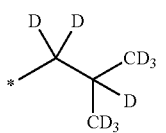
Formula 9-17
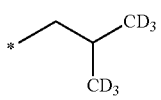
Formula 9-18
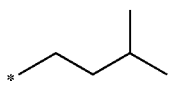
Formula 9-19
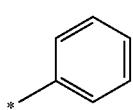
Formula 10-1
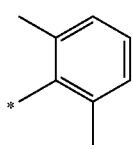
Formula 10-2
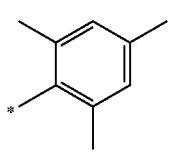
Formula 10-3
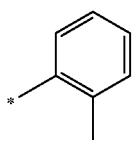
Formula 10-4
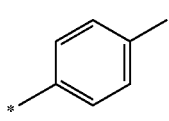
Formula 10-5
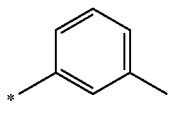
Formula 10-6
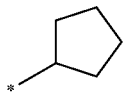
Formula 10-7
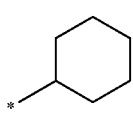
Formula 10-8
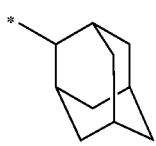
Formula 10-9
-continued
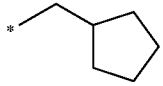
Formula 10-10
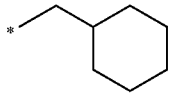
Formula 10-11
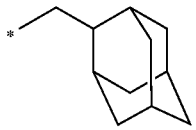
Formula 10-12
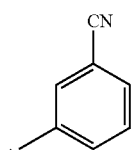
Formula 10-13
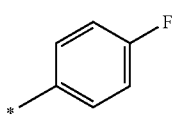
Formula 10-14
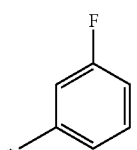
Formula 10-15
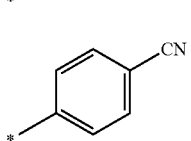
Formula 10-16
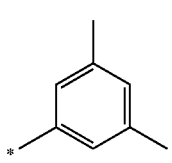
Formula 10-17
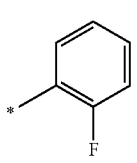
Formula 10-18
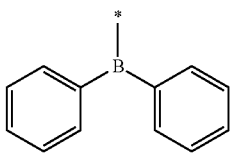
Formula 10-19
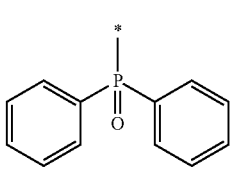
Formula 10-20

-continued
Formula 10-21
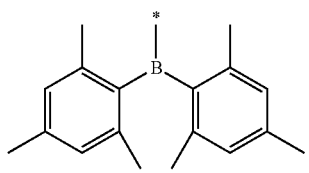
Formula 10-22
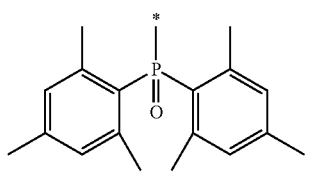
Formula 10-23
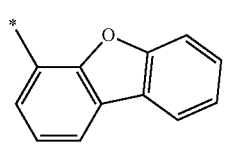
Formula 10-24
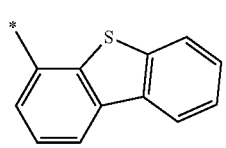
Formula 10-25
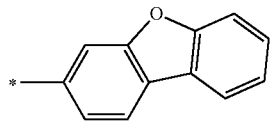
Formula 10-26
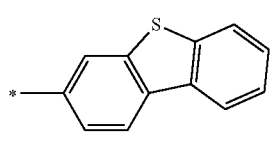
Formula 10-27
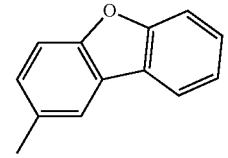
Formula 10-28
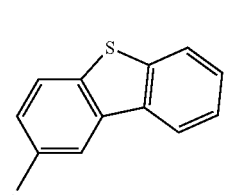
Formula 10-29
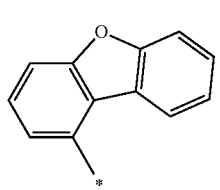
-continued
Formula 10-30
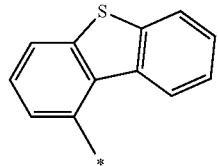
Formula 10-23
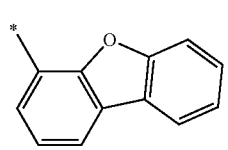
Formula 10-24
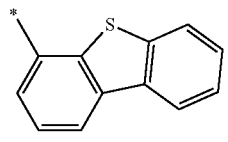
Formula 10-25
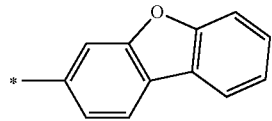
Formula 10-26
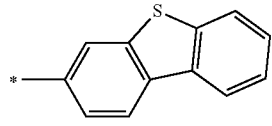
Formula 10-27
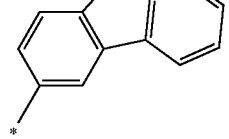
Formula 10-28
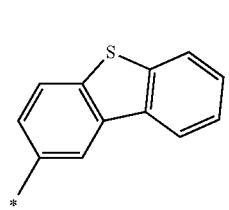
Formula 10-29
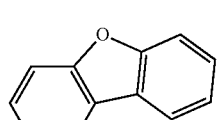
Formula 10-30
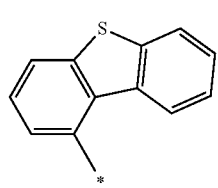

Formula 10-31
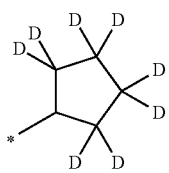
Formula 10-32
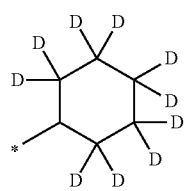
Formula 10-33
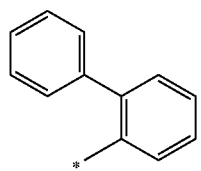
Formula 10-34
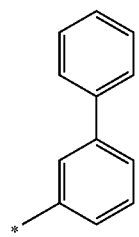
Formula 10-35
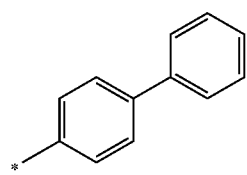
Formula 10-36
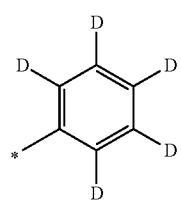
Formula 10-37
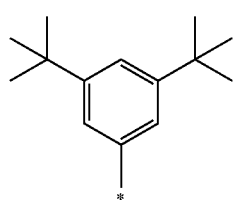
Formula 10-38
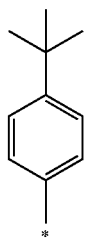
Formula 10-39
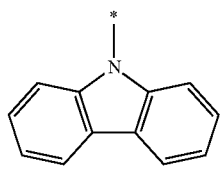
Formula 10-40
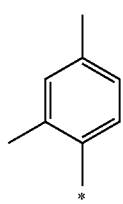
Formula 10-41
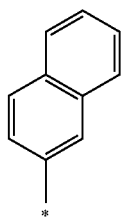
Formula 10-42
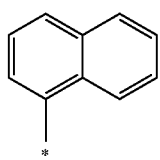
Formula 10-43
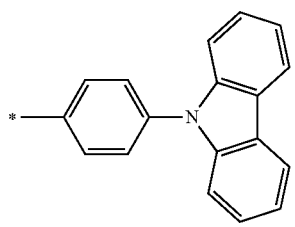
Formula 10-44
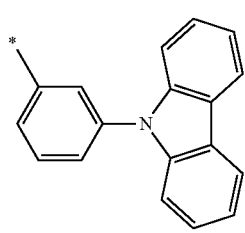

19

-continued

Formula 10-45

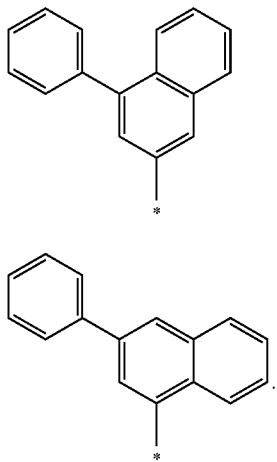

Formula 10-46

In Formulae 9-1 to 9-19 and 10-1 to 10-46, * indicates a binding site to a neighboring atom. $Q_3$ to $Q_5$ are the same as described above.

a1 in Formula 1 indicates the number of groups $R_1$ and may be 0, 1, 2, 3, 4, or 5. When a1 is 2 or greater, two or more groups $R_1$ may be identical to or different from each other. a2 to a4 may be understood by referring to the description provided in connection with a1 and Formula 1.

a1 to a4 in Formula 1 may each independently be 0, 1, 2, 3, 4, or 5. In one or more embodiments, a1 to a4 may each independently be 0, 1, or 2, but are not limited thereto.

In Formula 1, two groups selected from groups $R_1$ in the number of a1 may be optionally connected to each other to form a substituted or unsubstituted $C_5$-$C_{30}$ carbocyclic group or a substituted or unsubstituted $C_1$-$C_{30}$ heterocyclic group, two groups selected from groups $R_2$ in the number of a2 may be optionally connected to each other to form a substituted or unsubstituted $C_5$-$C_{30}$ carbocyclic group or a substituted or unsubstituted $C_1$-$C_{30}$ heterocyclic group, two groups selected from groups $R_3$ in the number of a3 may be optionally connected to each other to form a substituted or unsubstituted $C_5$-$C_{30}$ carbocyclic group or a substituted or unsubstituted $C_1$-$C_{30}$ heterocyclic group, and two groups selected from groups $R_4$ in the number of a4 may be optionally connected to each other to form a substituted or unsubstituted $C_5$-$C_{30}$ carbocyclic group or a substituted or unsubstituted $C_1$-$C_{30}$ heterocyclic group. Examples of the substituted or unsubstituted $C_5$-$C_{30}$ carbocyclic group or the substituted or unsubstituted $C_1$-$C_{30}$ heterocyclic group may include a substituted or unsubstituted pentadiene group, a substituted or unsubstituted cyclohexane group, a substituted or unsubstituted adamantane group, a substituted or unsubstituted benzene group, a substituted or unsubstituted pyridine group, a substituted or unsubstituted pyrimidine group, a substituted or unsubstituted pyrazine group, a substituted or unsubstituted pyridazine group, a substituted or unsubstituted naphthalene group, a substituted or unsubstituted anthracene group, a substituted or unsubstituted tetracene group, a substituted or unsubstituted phenanthrene group, a substituted or unsubstituted dihydronaphthalene group, a substituted or unsubstituted phenalene group, a substituted or unsubstituted benzothiophene group, a substituted or unsubstituted benzofuran group, a substituted or unsubstituted indene group, and a substituted or unsubstituted indole group.

20

In one or more embodiments, the organometallic compound may be represented by Formula 1-1:

Formula 1-1

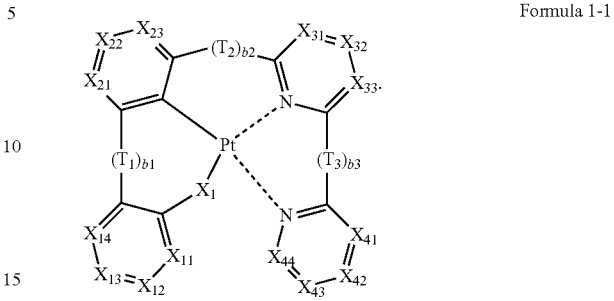

In Formula 1-1, $X_1$, $T_1$ to $T_3$, and b1 to b3 are the same as described above, $X_{11}$ may be N or $C(R_{11})$, $X_{12}$ may be N or $C(R_{12})$, $X_{13}$ may be N or $C(R_{13})$, $X_{14}$ may be N or $C(R_{14})$, $X_{21}$ may be N or $C(R_{21})$, $X_{22}$ may be N or $C(R_{22})$, $X_{23}$ may be N or $C(R_{23})$, $X_{31}$ may be N or $C(R_{31})$, $X_{32}$ may be N or $C(R_{32})$, $X_{33}$ may be N or $C(R_{33})$, $X_{41}$ may be N or $C(R_{41})$, $X_{42}$ may be N or $C(R_{42})$, $X_{43}$ may be N or $C(R_{43})$, and $X_{44}$ may be N or $C(R_{44})$, $R_{11}$ to $R_{14}$ are each independently the same as described above in connection with $R_1$, and two groups selected from $R_{11}$ to $R_{14}$ may be optionally connected to each other to form a substituted or unsubstituted $C_5$-$C_{30}$ carbocyclic group or a substituted or unsubstituted $C_1$-$C_{30}$ heterocyclic group, $R_{21}$ to $R_{23}$ are each independently the same as described above in connection with $R_2$, and two groups selected from $R_{21}$ to $R_{23}$ may be optionally connected to each other to form a substituted or unsubstituted $C_5$-$C_{30}$ carbocyclic group or a substituted or unsubstituted $C_1$-$C_{30}$ heterocyclic group, $R_{31}$ to $R_{33}$ are each independently the same as described above in connection with $R_3$, and two groups selected from $R_{31}$ to $R_{33}$ may be optionally connected to each other to form a substituted or unsubstituted $C_5$-$C_{30}$ carbocyclic group or a substituted or unsubstituted $C_1$-$C_{30}$ heterocyclic group, $R_{41}$ to $R_{44}$ are each independently the same as described above in connection with $R_4$, and two groups selected from $R_{41}$ to $R_{44}$ may be optionally connected to each other to form a substituted or unsubstituted $C_5$-$C_{30}$ carbocyclic group or a substituted or unsubstituted $C_1$-$C_{30}$ heterocyclic group, and two groups selected from $R_{11}$ to $R_{14}$, $R_{21}$ to $R_{23}$, $R_{31}$ to $R_{33}$, and $R_{41}$ to $R_{44}$ may be optionally connected to each other to form a substituted or unsubstituted $C_5$-$C_{30}$ carbocyclic group or a substituted or unsubstituted $C_1$-$C_{30}$ heterocyclic group.

In one or more embodiments, the organometallic compound may be represented by Formula 1-1A:

Formula 1-1A

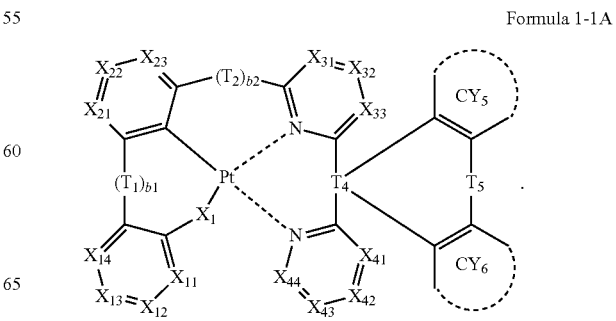

In Formula 1-1A, $T_1$, $T_2$, b1, and b2 are the same as described above, $X_{11}$ to $X_{14}$, $X_{21}$ to $X_{23}$, $X_{31}$ to $X_{33}$, and $X_{41}$ to $X_{44}$ are the same as described above, $T_4$ may be C, Si, or P, $T_5$ may be selected from a single bond, *—O—*', *—S—*', *—C($R_9$)($R_{10}$)—*', *—C($R_9$)=*', *=C($R_9$)—*', *—C($R_9$)=C($R_{10}$)—*', *—C(=O)—*', *—C(=S)—*' *—C≡C—*', *—N($R_9$)—*', *—Si($R_9$)($R_{10}$)—*', and *—P($R_9$)($R_{10}$)—*', wherein * and *' in each of the foregoing groups independently indicate a binding site to a neighboring atom, $R_9$ and $R_{10}$ are each independently the same as described above in connection with $R_7$, and $CY_5$ and $CY_6$ may each independently be selected from:

a cyclopentane group, a cyclohexane group, a cycloheptane group, a benzene group, a naphthalene group, a fluorene group, a phenanthrene group, an anthracene group, a triphenylene group, a pyrene group, a chrysene group, a pyridine group, a pyrimidine group, a quinoline group, an isoquinoline group, a quinazoline group, and a quinoxaline group; and a cyclopentane group, a cyclohexane group, a cycloheptane group, a benzene group, a naphthalene group, a fluorene group, a phenanthrene group, an anthracene group, a triphenylene group, a pyrene group, a chrysene group, a pyridine group, a pyrimidine group, a quinoline group, an isoquinoline group, a quinazoline group, and a quinoxaline group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a phenyl group, a naphthyl group, a pyridinyl group, and a pyrimidinyl group, but embodiments are not limited thereto.

In one or more embodiments, the organometallic compound may be represented by one selected from Formulae 1(1) to 1(41):

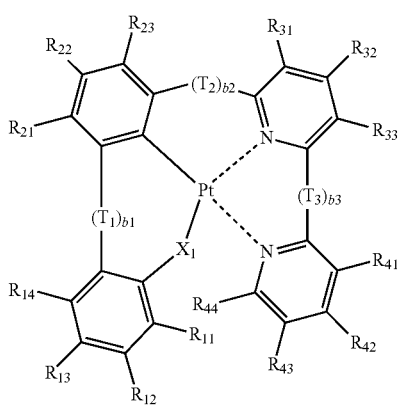

Formula 1(1)

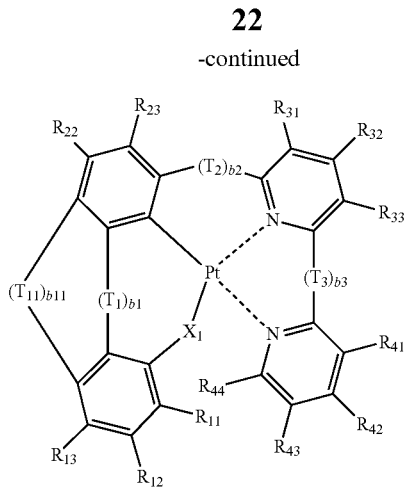

Formula 1(2)

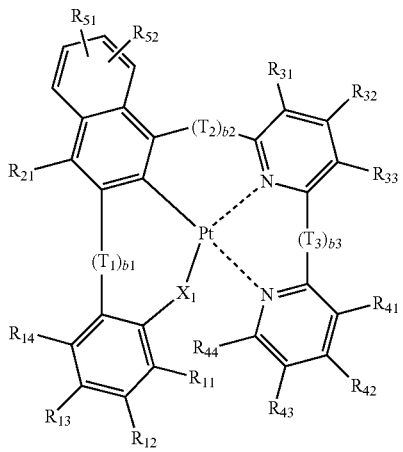

Formula 1(3)

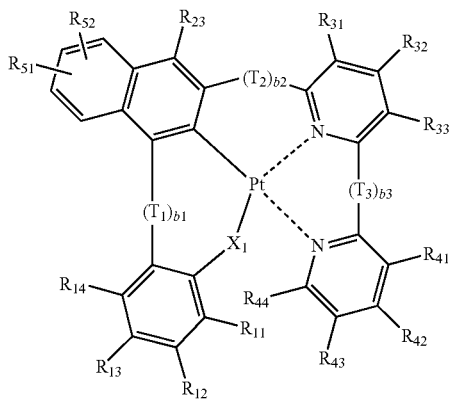

Formula 1(4)

Formula 1(5)
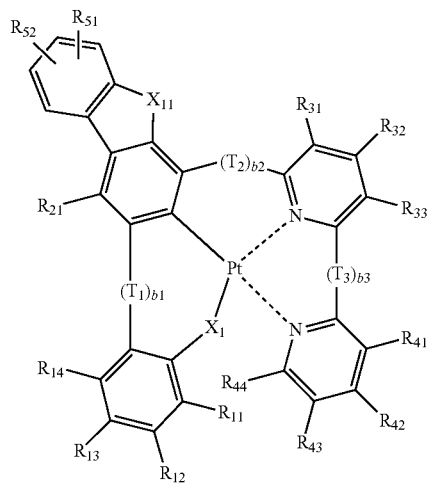
Formula 1(6)
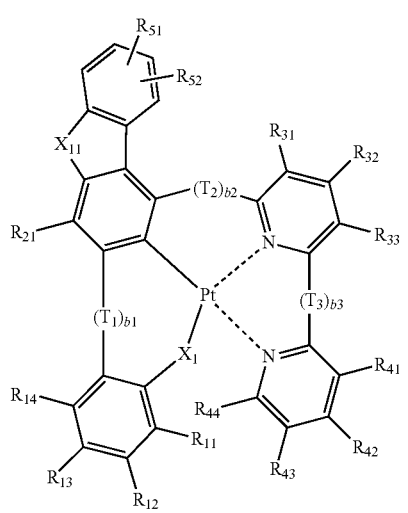
Formula 1(7)
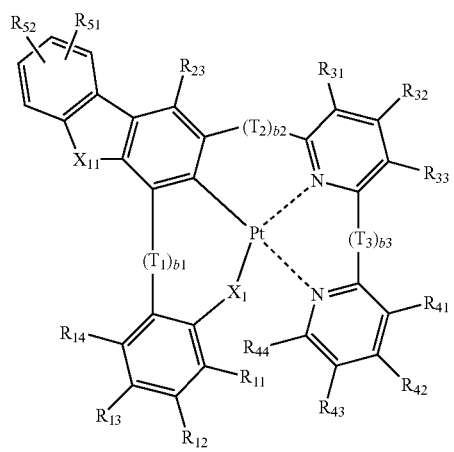
Formula 1(8)
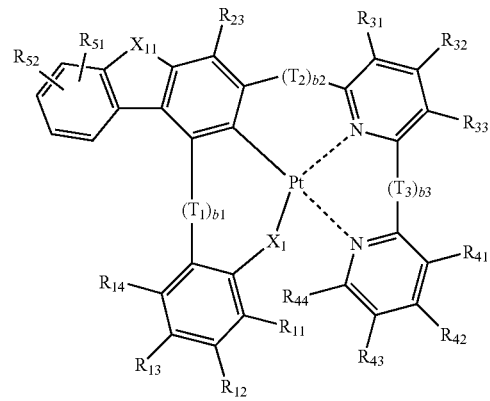
Formula 1(9)
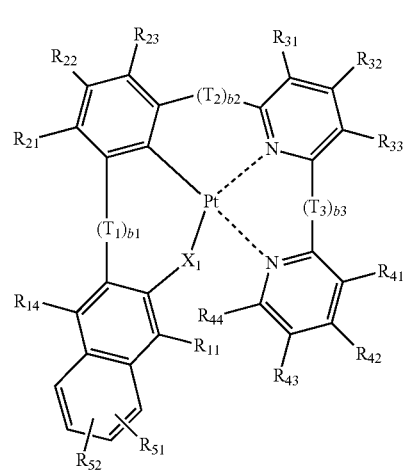
Formula 1(10)
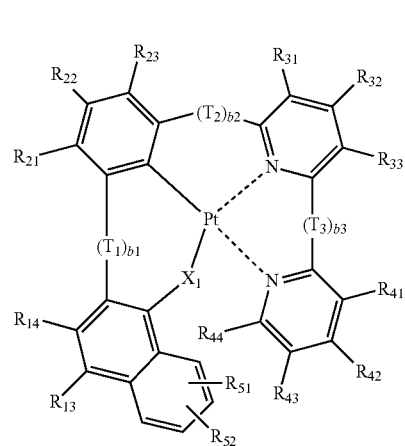

Formula 1(11)
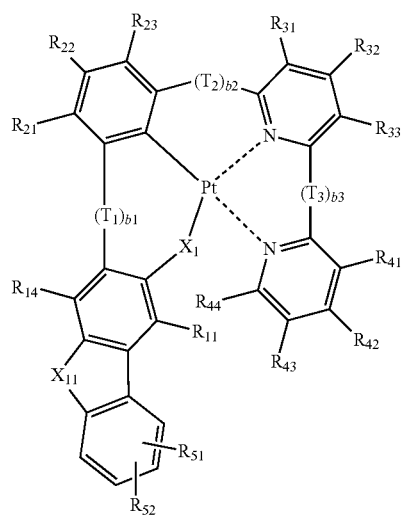
Formula 1(12)
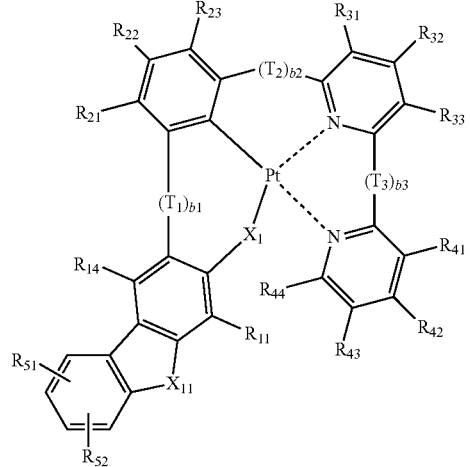
Formula 1(13)
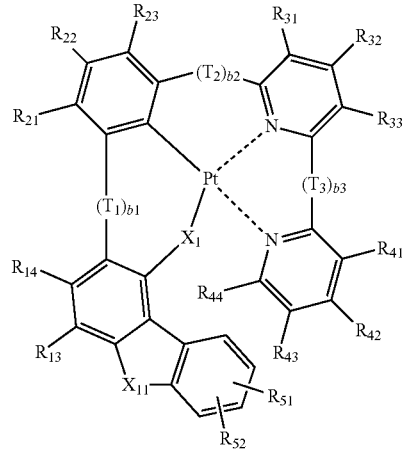
Formula 1(14)
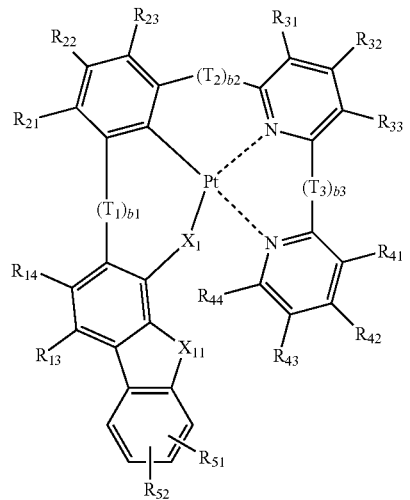
Formula 1(15)
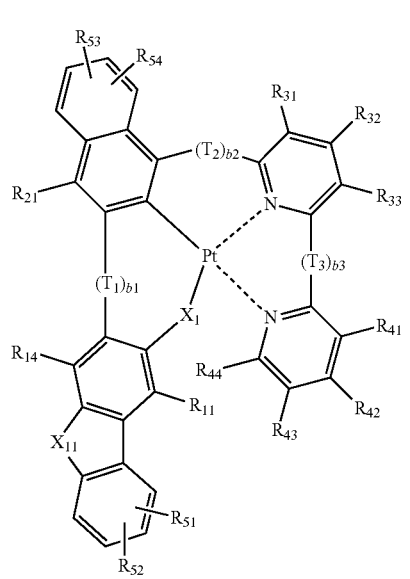
Formula 1(16)
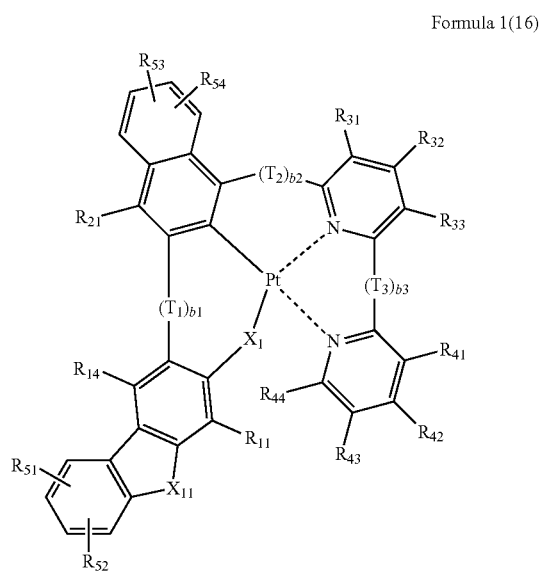

Formula 1(17)
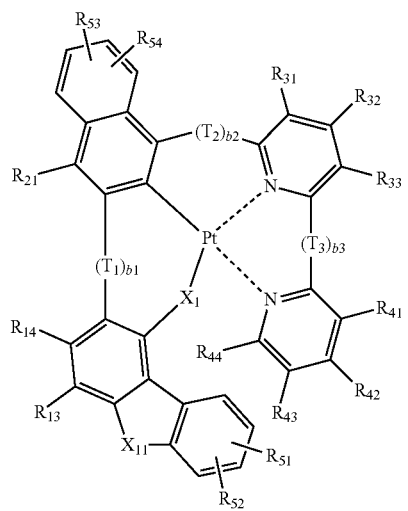
Formula 1(18)
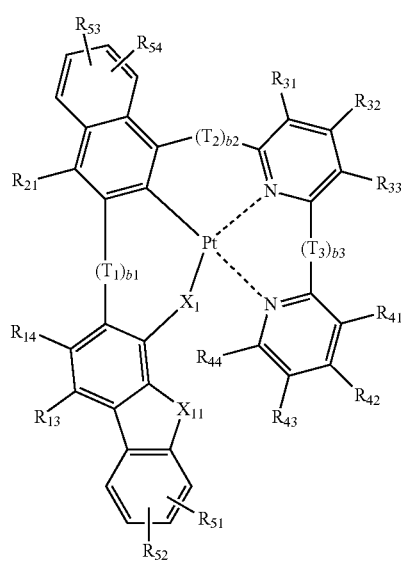
Formula 1(19)
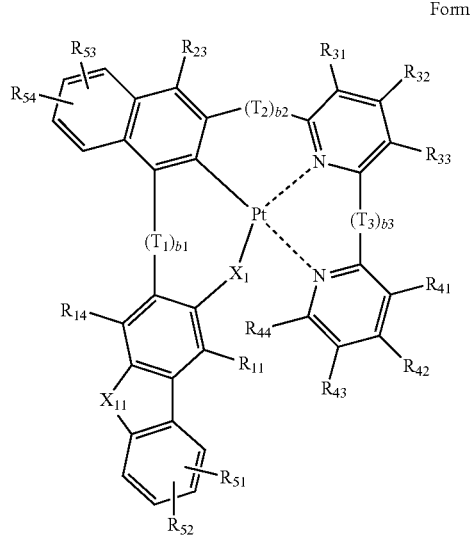
Formula 1(20)
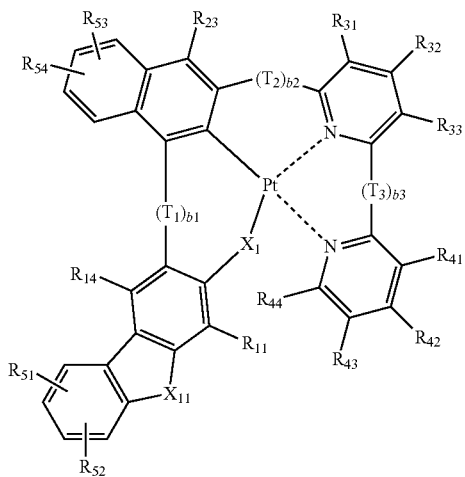
Formula 1(21)
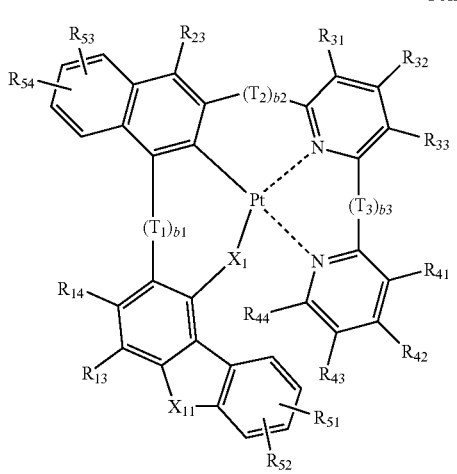
Formula 1(22)
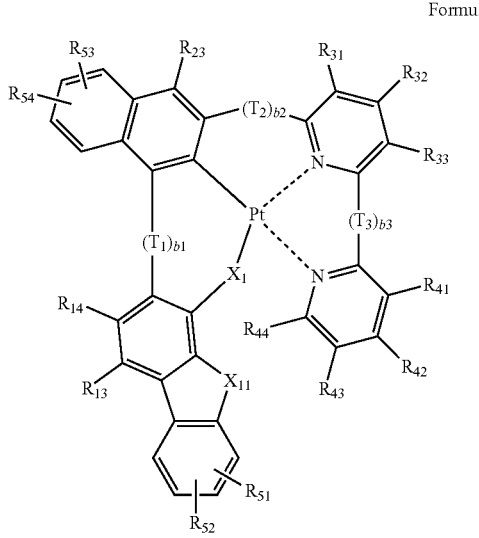

Formula 1(23)
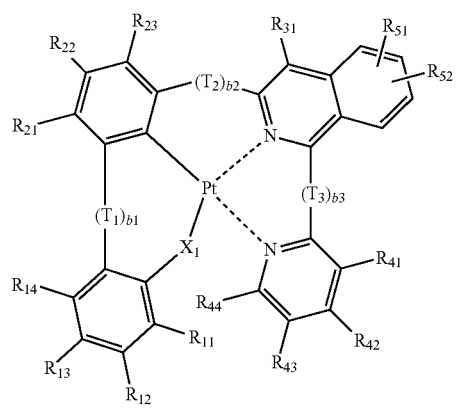
Formula 1(24)
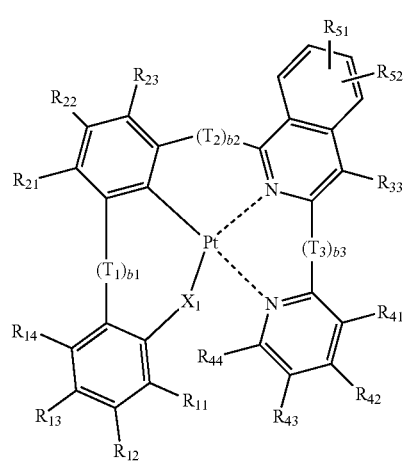
Formula 1(25)
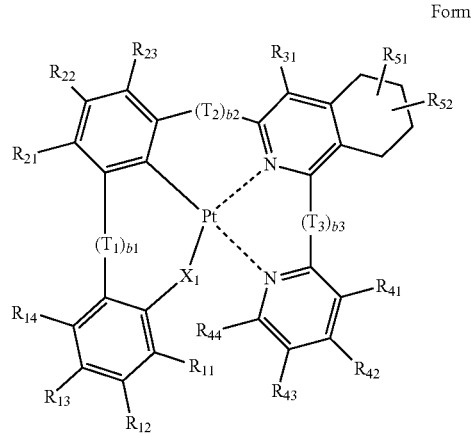
Formula 1(26)
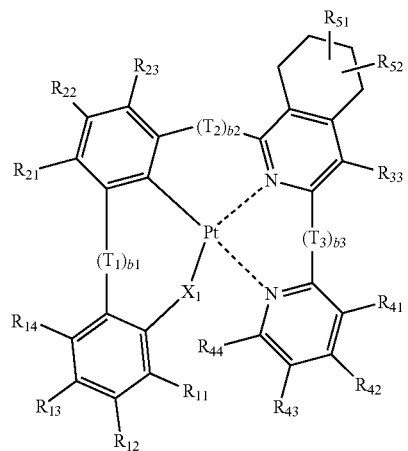
Formula 1(27)
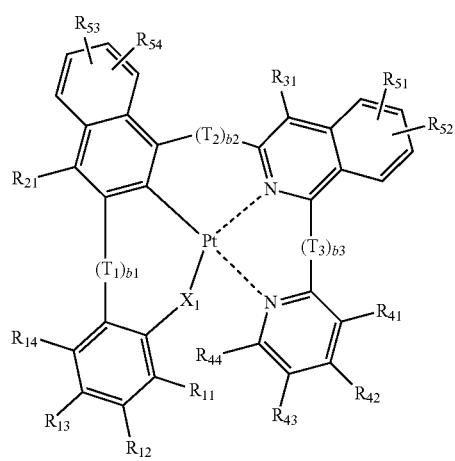
Formula 1(28)
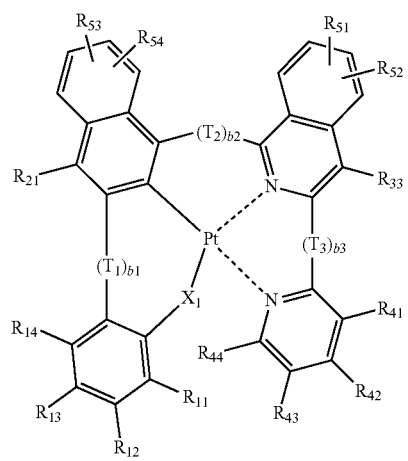

-continued
Formula 1(29)
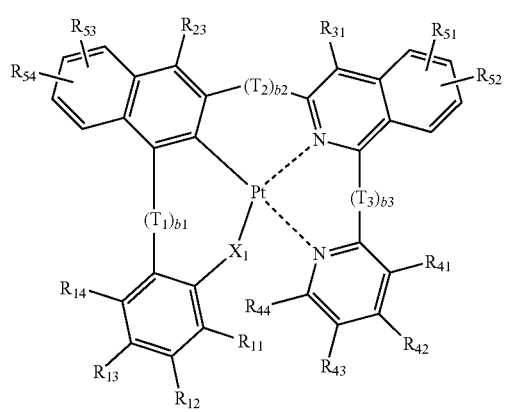
Formula 1(30)
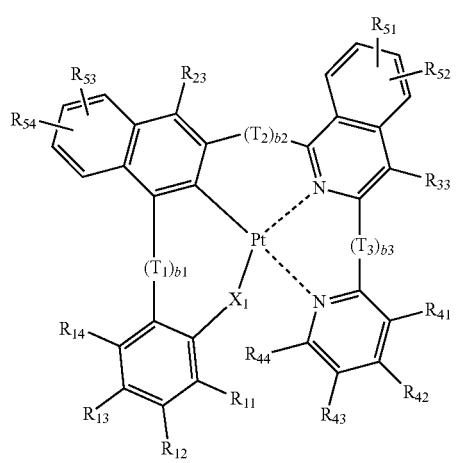
Formula 1(31)
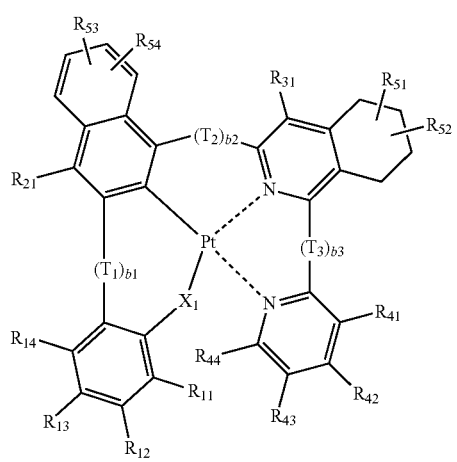
-continued
Formula 1(32)
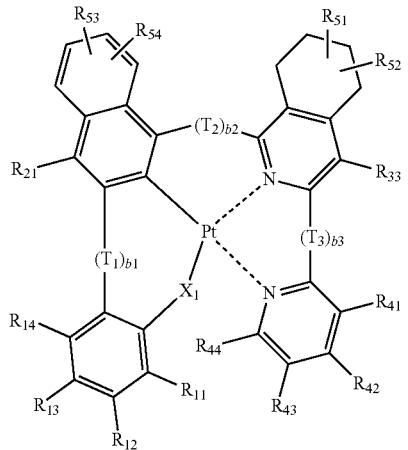
Formula 1(33)
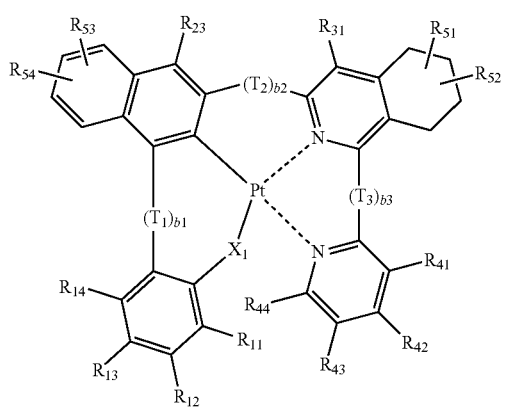
Formula 1(34)
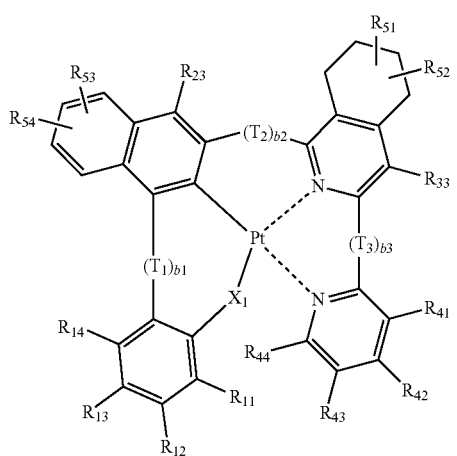

Formula 1(35)
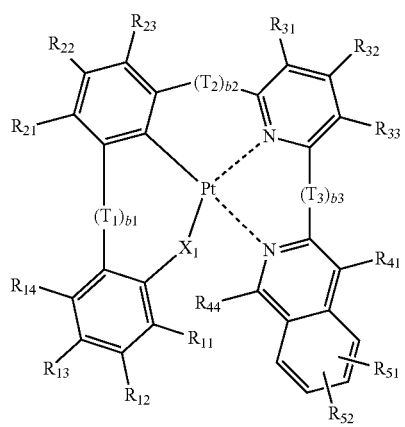
Formula 1(36)
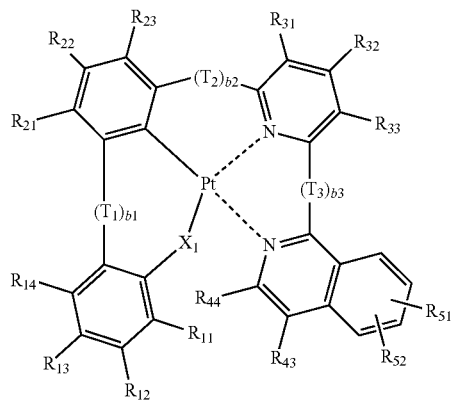
Formula 1(37)
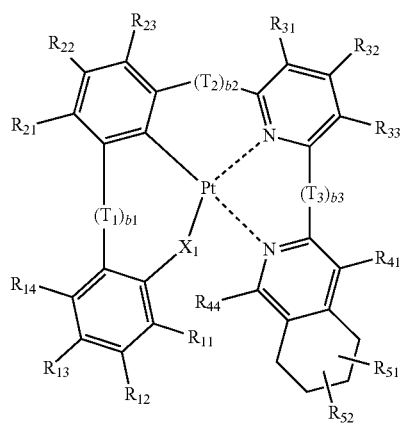
Formula 1(38)
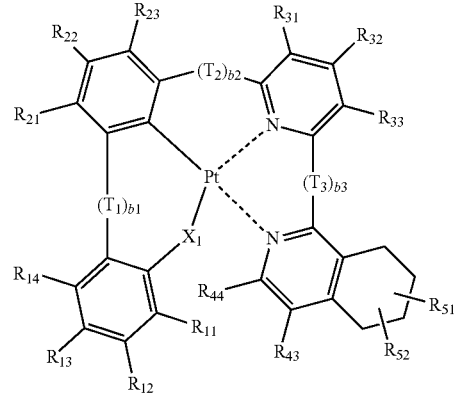
Formula 1(39)
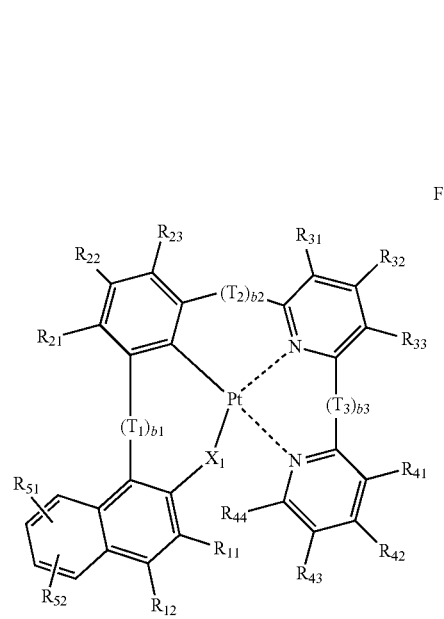
Formula 1(40)
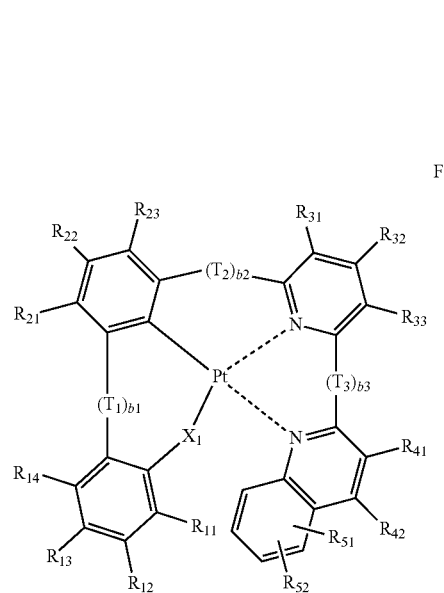

-continued

Formula 1(41)

In Formulae 1(1) to 1(41), $X_1$, $T_1$ to $T_3$, and b1 to b3 are the same as described above, $R_{11}$ to $R_{14}$ are each independently the same as described above in connection with $R_1$, $R_{21}$ to $R_{23}$ are each independently the same as described above in connection with $R_2$, $R_{31}$ to $R_{33}$ are each independently the same as described above in connection with $R_3$, $R_{41}$ to $R_{44}$ are each independently the same as described above in connection with $R_4$, $X_{11}$ may be O or S, $R_{51}$ to $R_{54}$ are each independently the same as described above in connection with $R_1$, $T_{11}$ may be a group selected from *—O—*', *—S—*', *—C($R_{61}$)($R_{62}$)—*', *—C($R_{61}$)=*', *=C($R_{61}$)—*', *—C($R_{61}$)=C($R_{62}$)—*', *—C(=O)—*', *—C(=S)—*', *—C≡C—*', *—N($R_{61}$)—*', *—Si($R_{61}$)($R_{62}$)—*', and *—P($R_{61}$)($R_{62}$)—*', wherein * and *' in each of the foregoing groups independently indicate a binding site to a neighboring atom, $R_{61}$ and $R_{62}$ are each independently the same as described above in connection with $R_7$, and b11 may be 1, 2, or 3.

For example, in Formulae 1-1, 1-1A, and 1(1) to 1(41), $T_1$ may be a single bond, $T_2$ may be a group selected from a single bond, *—O—*', *—S—*', *—C($R_5$)($R_6$)—*', *—N($R_5$)—*', *—Si($R_5$)($R_6$)—*', and *—P($R_5$)($R_6$)—*', wherein * and *' in each of the foregoing groups independently indicate a binding site to a neighboring atom, $T_3$ may be a group selected from *—O—*', *—S—*', *—C($R_7$)($R_8$)—*', *—N($R_7$)—*', *—Si($R_7$)($R_8$)—*', and *—P($R_7$)($R_8$)—*', wherein * and *' in each of the foregoing groups independently indicate a binding site to a neighboring atom, b1 to b3 may be 1, and $R_5$ to $R_8$, $R_{11}$ to $R_{14}$, $R_{21}$ to $R_{23}$, $R_{31}$ to $R_{33}$, $R_{41}$ to $R_{44}$, $R_{51}$ to $R_{54}$, $R_{61}$, and $R_{62}$ may each independently be selected from hydrogen, deuterium, —F, a cyano group, a nitro group, —SF$_5$, —CH$_3$, —CD$_3$, —CD$_2$H, —CDH$_2$, —CF$_3$, —CF$_2$H, —CFH$_2$, groups represented by Formulae 9-1 to 9-19, groups represented by Formulae 10-1 to 10-46, and —Si($Q_3$)($Q_4$)($Q_5$), but are not limited thereto. $Q_3$ to $Q_5$ are the same as described above.

In one or more embodiments, in Formulae 1-1 and 1-1A, a) two groups selected from $R_{11}$ to $R_{14}$, b) two groups selected from $R_{21}$ to $R_{23}$, c) two groups selected from $R_{31}$ to $R_{33}$, or d) two groups selected from $R_{41}$ to $R_{44}$ may be optionally connected to each other to form one selected from:

a cyclopentane group, a cyclohexane group, an adamantane group, a norbornane group, a benzene group, a pyridine group, a pyrimidine group, a naphthalene group, a pyrene group, and a chrysene group; and a cyclopentane group, a cyclohexane group, an adamantane group, a norbornane group, a benzene group, a pyridine group, a pyrimidine group, a naphthalene group, a pyrene group, and a chrysene group, each substituted with at least one selected from deuterium, —F, —CD$_3$, —CD$_2$H, —CDH$_2$, —CF$_3$, —CF$_2$H, —CFH$_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, but embodiments are not limited thereto.

In one or more embodiments, the organometallic compound may be one selected from Compounds 1 to 78, but is not limited thereto:

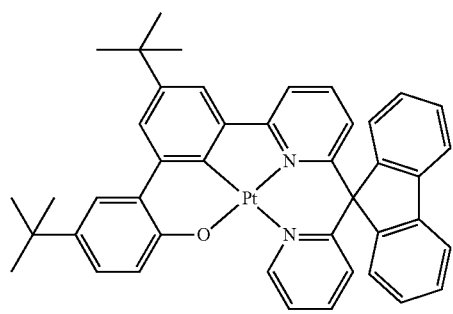
4
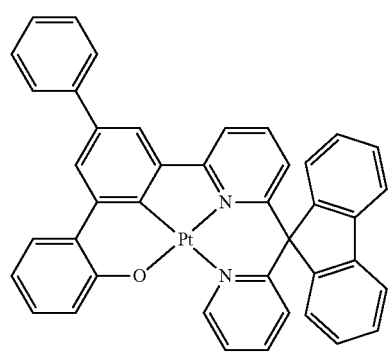
5
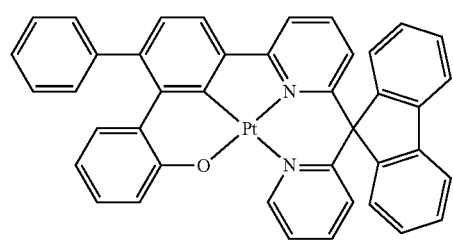
6
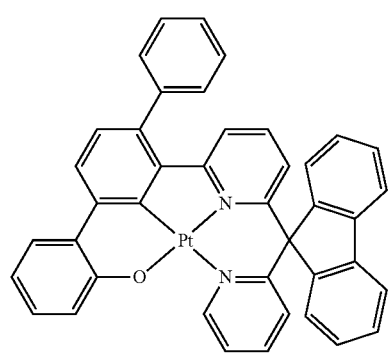
7
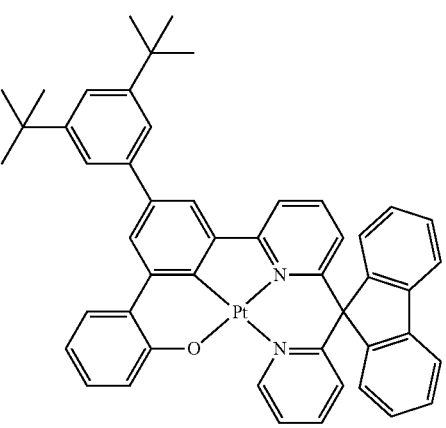
8
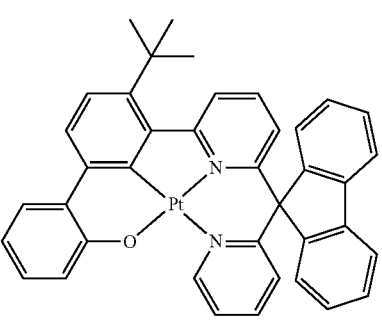
9
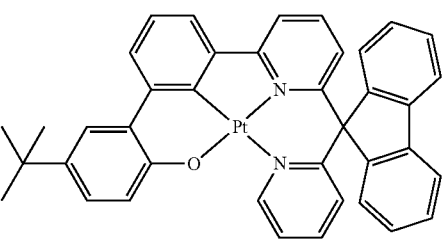
10
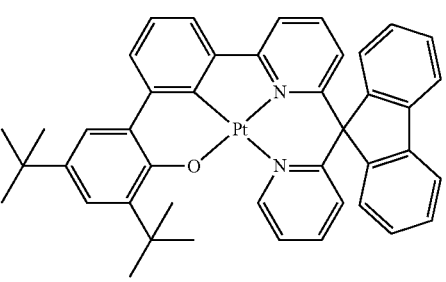
11

12
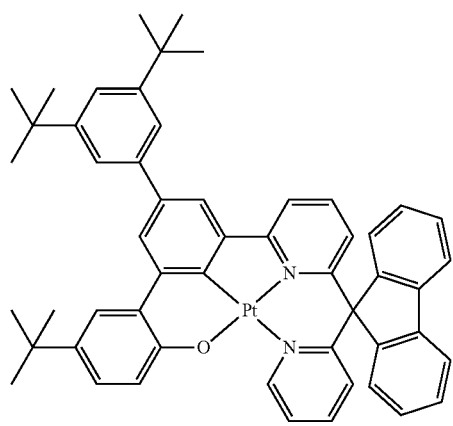
13
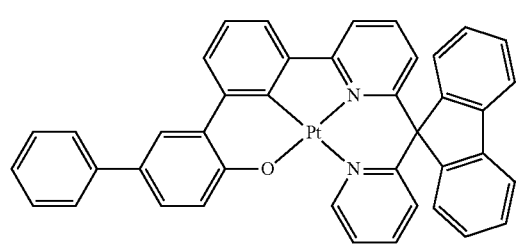
14
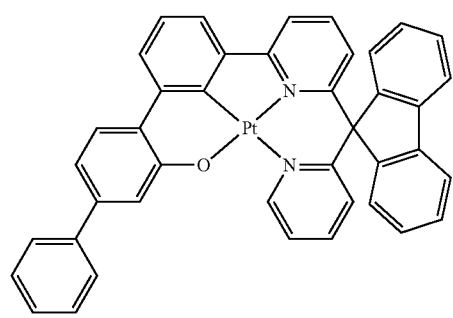
15
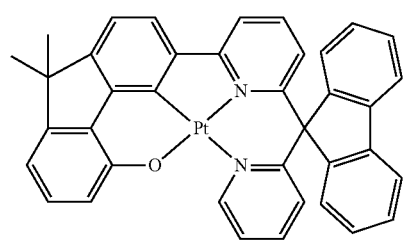
16
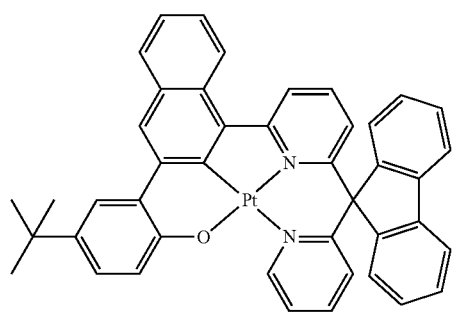
17
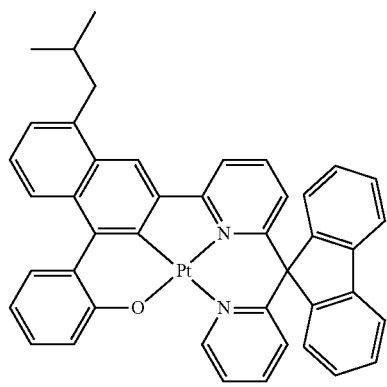
18
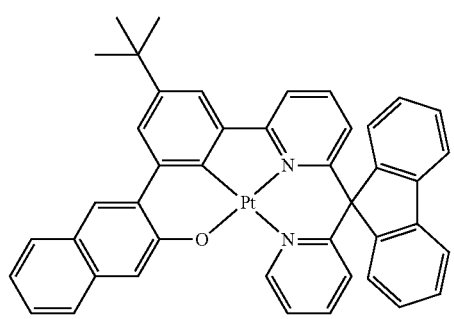
19
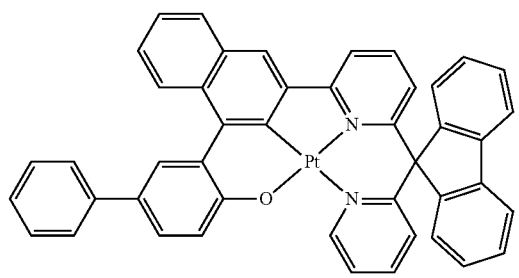
20
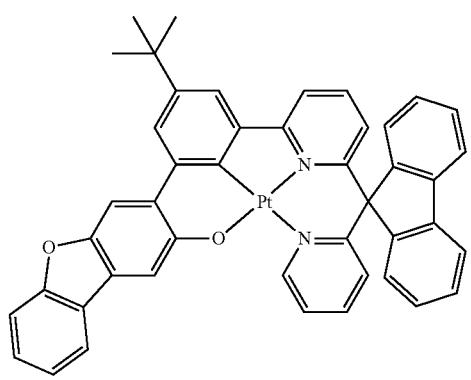
21
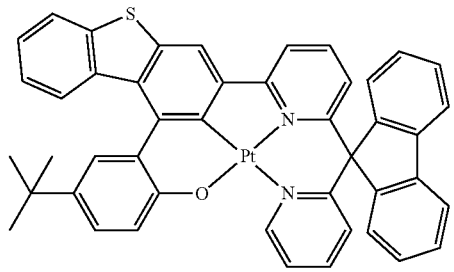

22
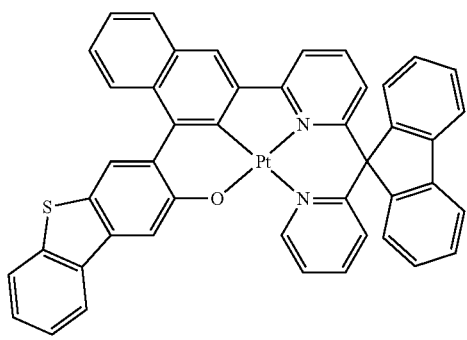
23
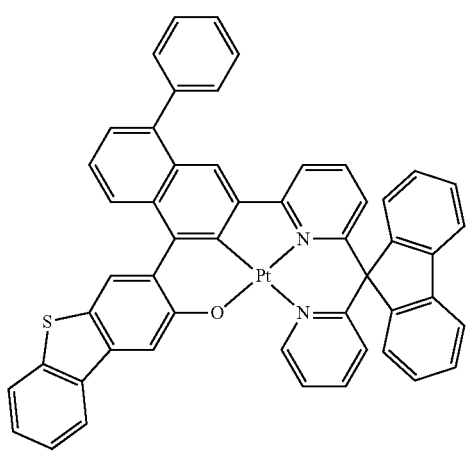
24
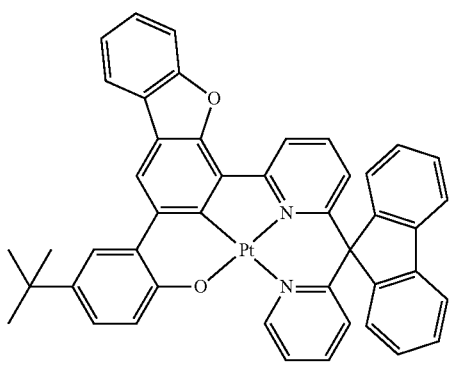
25
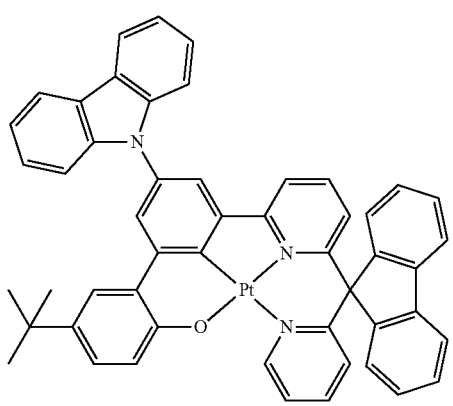
26
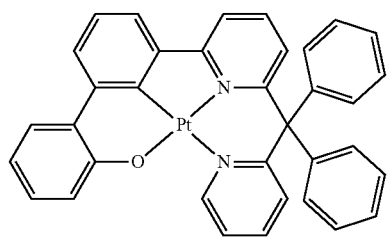
27
28
29

30
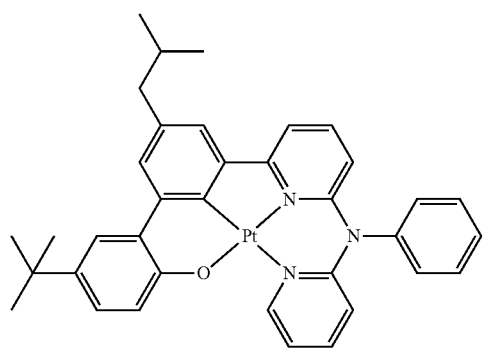
34
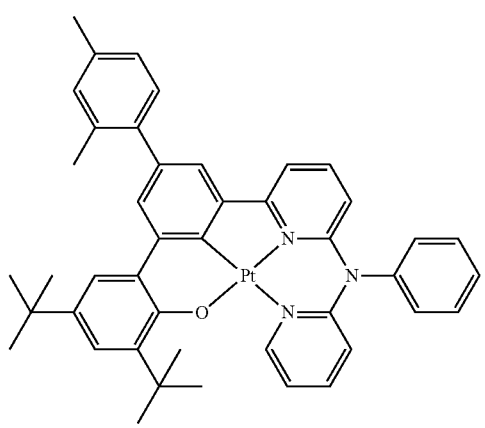
31
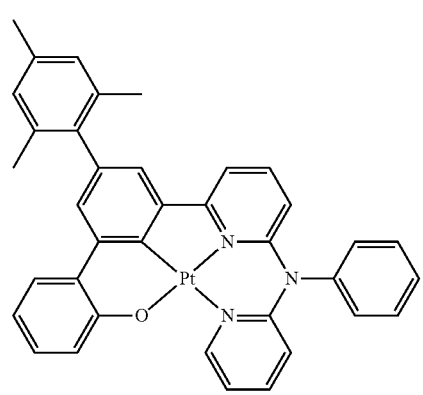
35
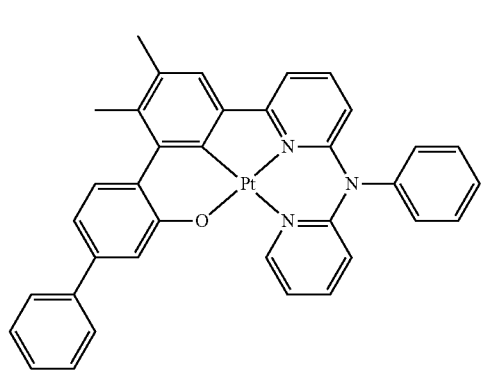
32
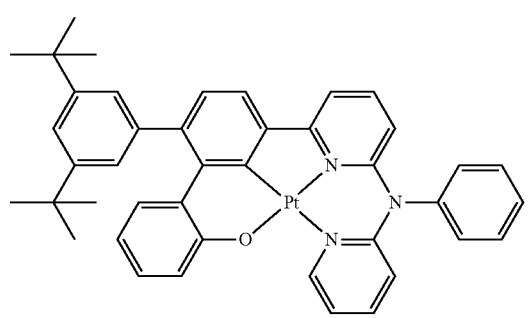
36
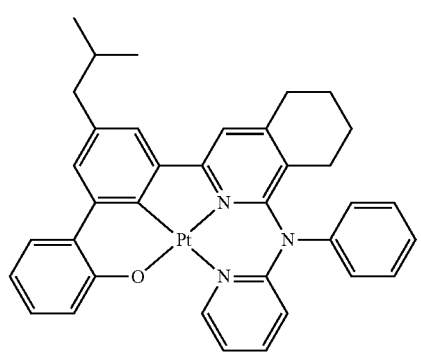
33
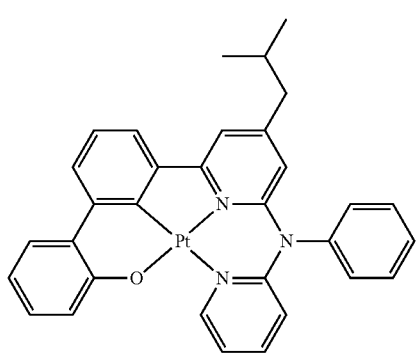
37
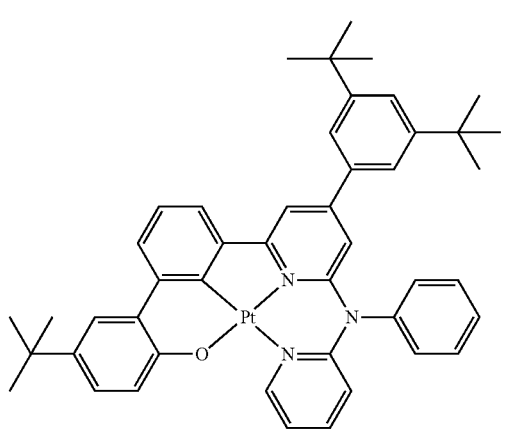

38
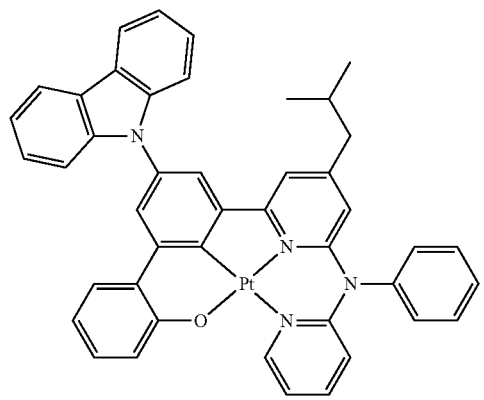
39
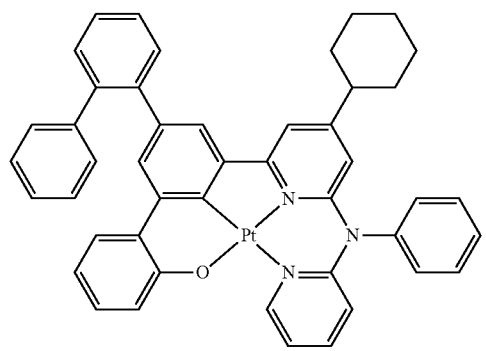
40
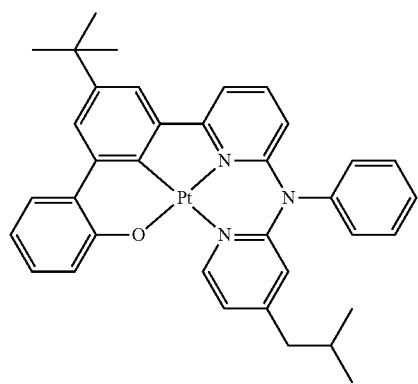
41
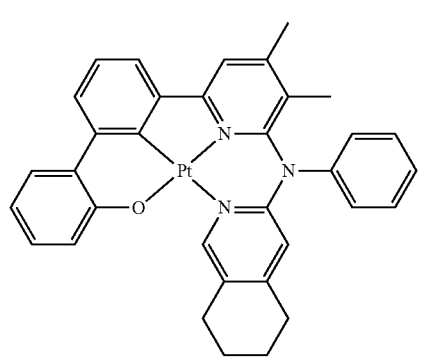
42
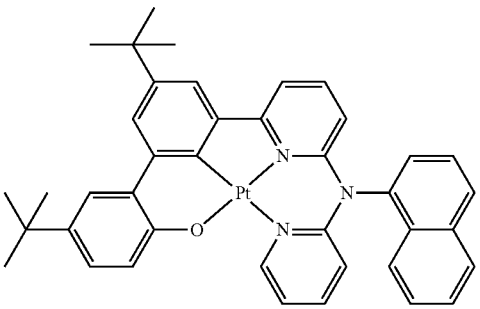
43
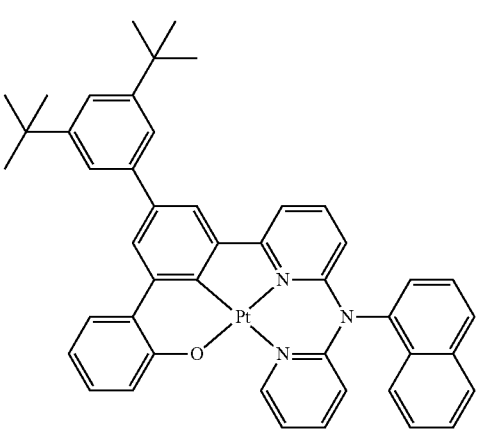
44
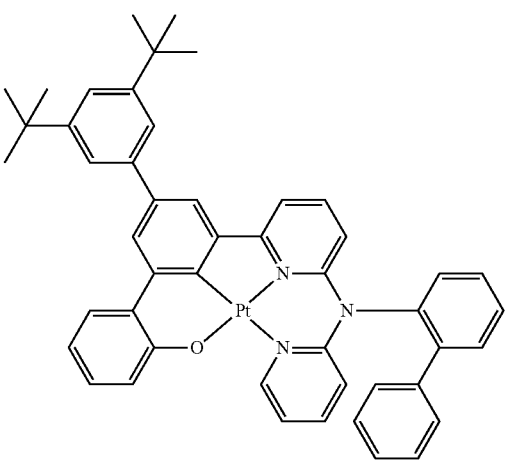
45

-continued
46
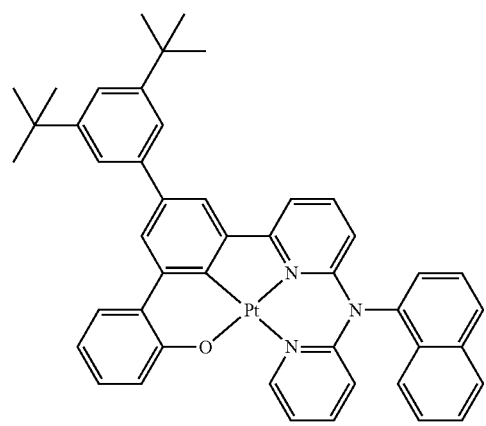
47
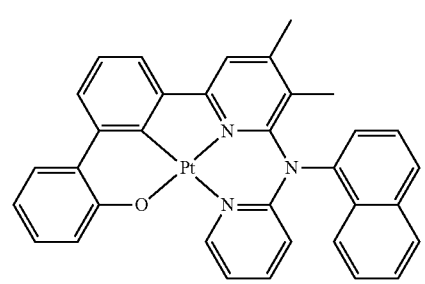
48
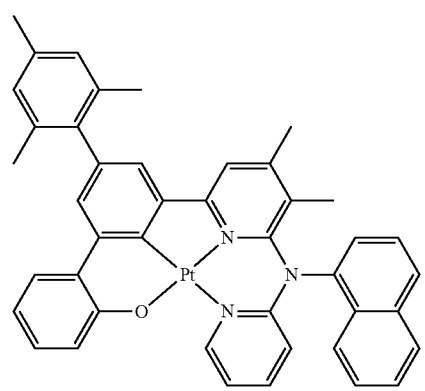
49
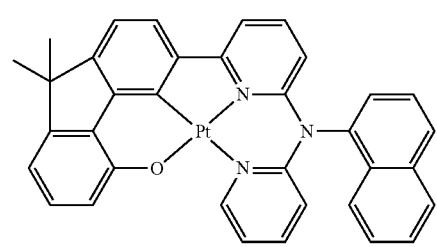
50
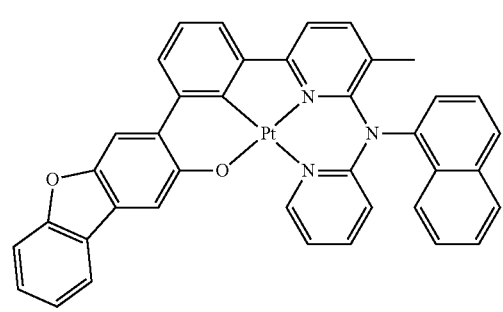
-continued
51
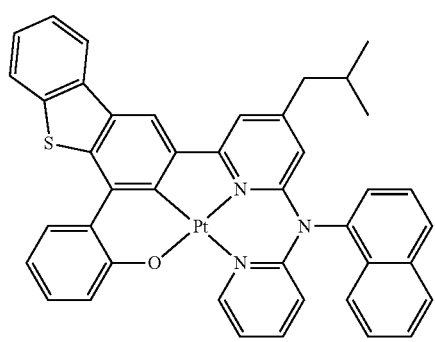
52
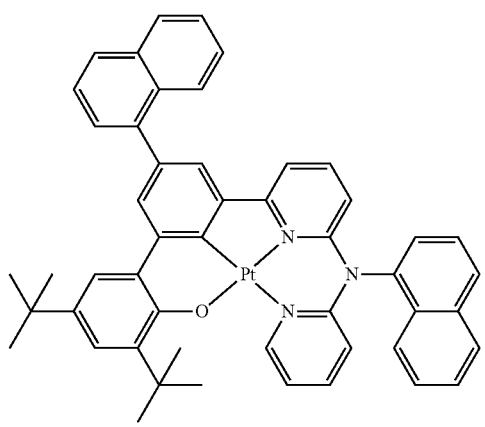
53
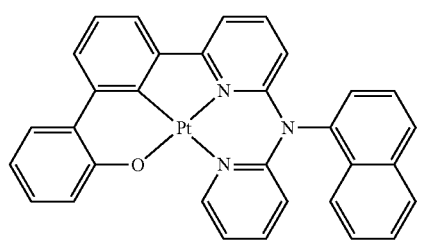
54
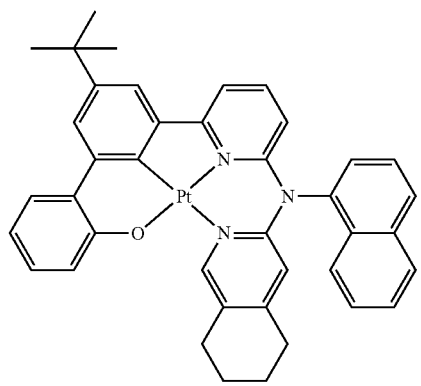

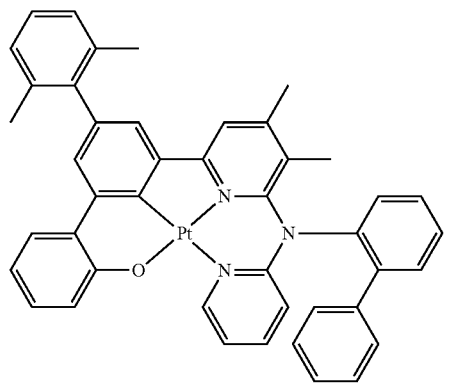
55
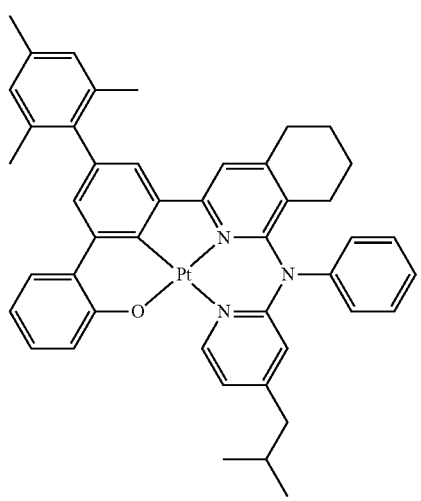
59
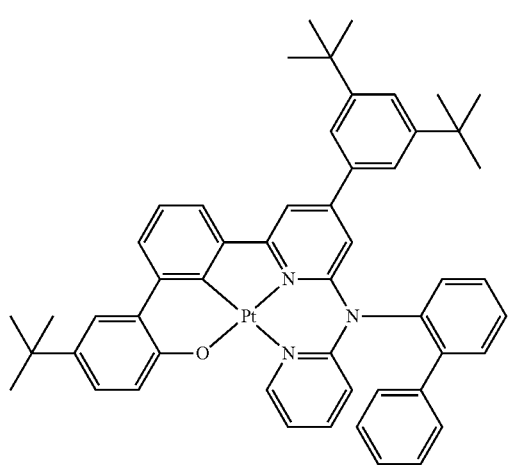
56
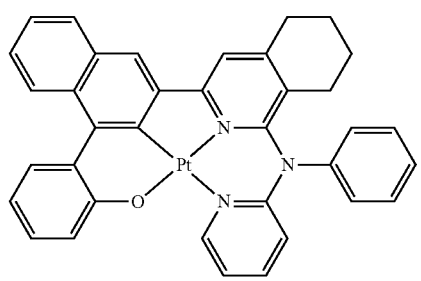
60
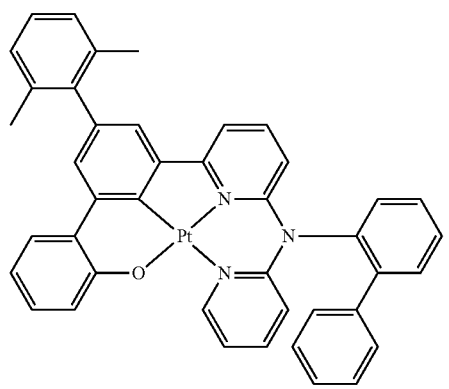
57
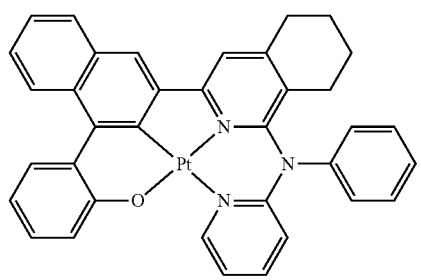
61
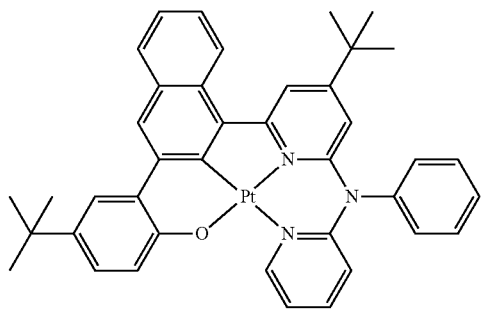
62
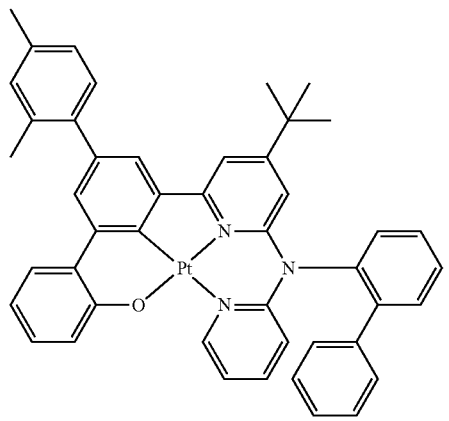
58
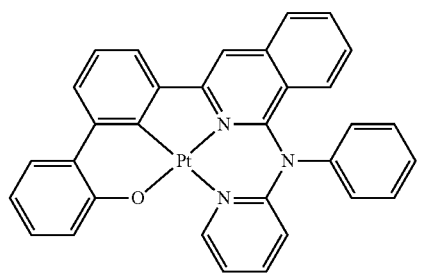
63

64
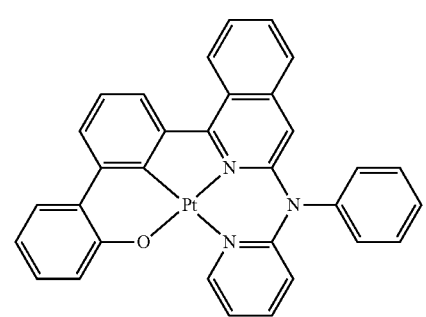
65
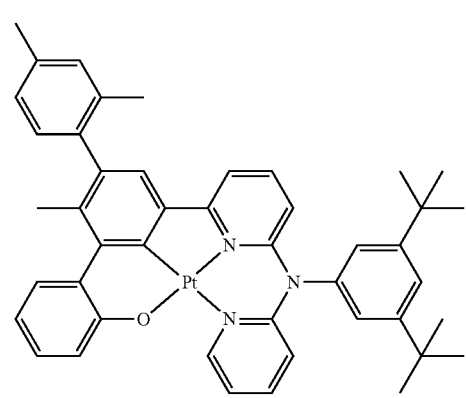
66
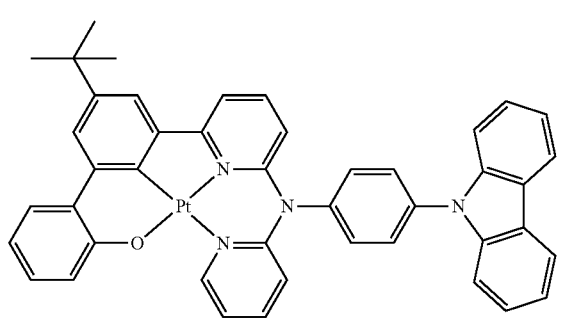
67
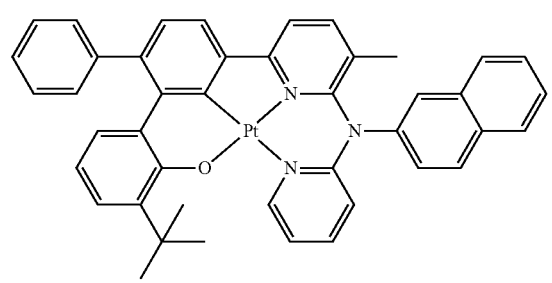
68
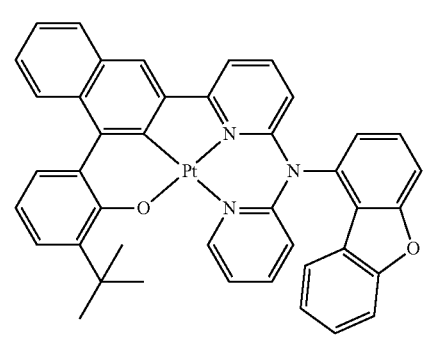
69
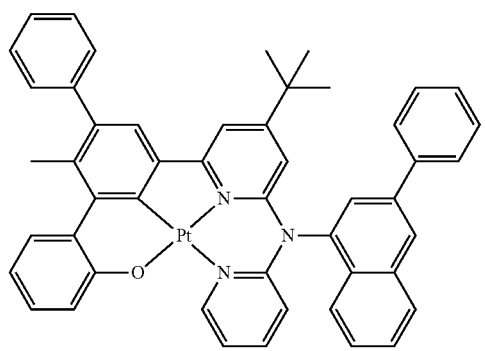
70
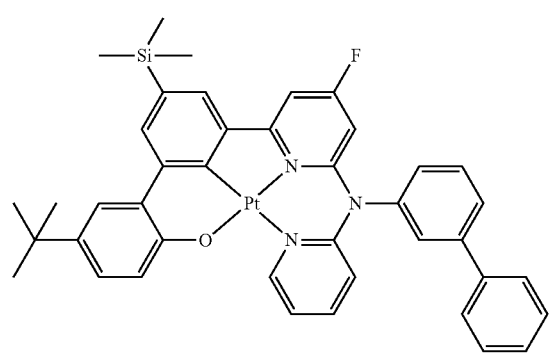
71
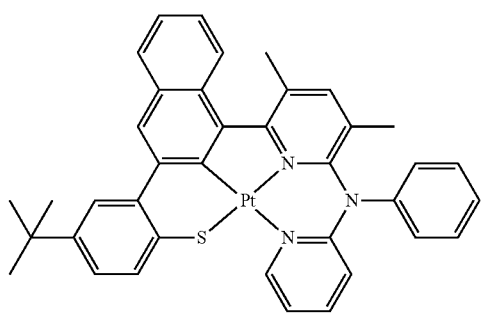
72
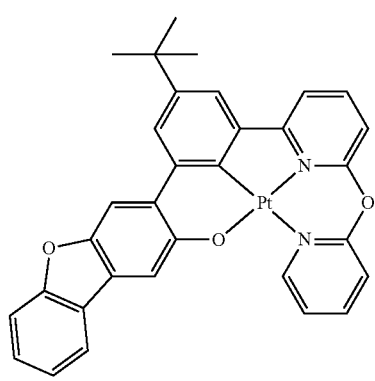

-continued

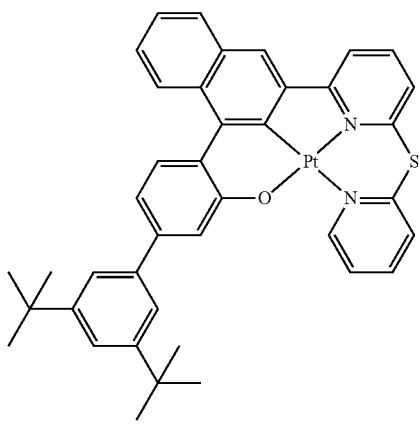
73

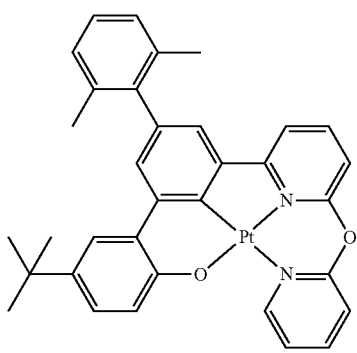
74

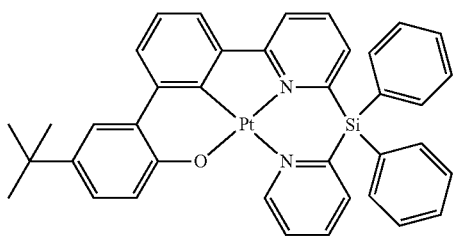
75

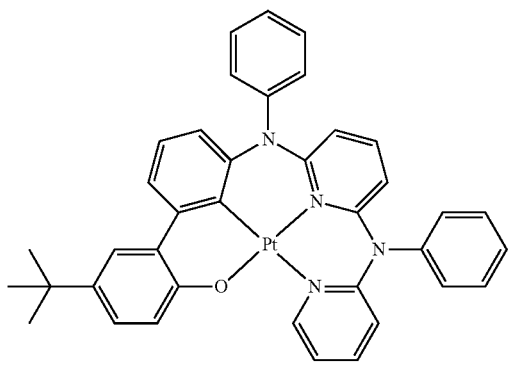
76

-continued

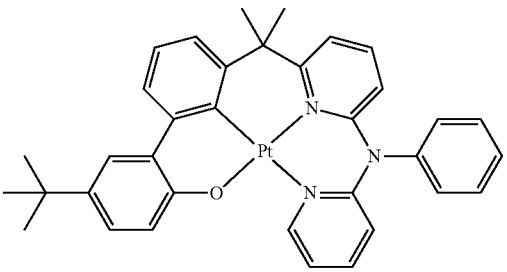
77

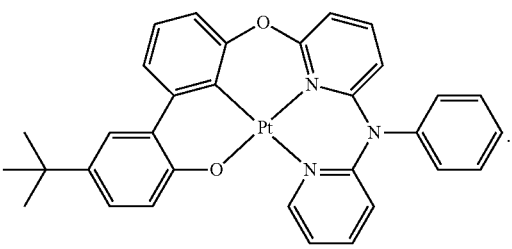
78

In Formula 1, $X_1$ may be O or S, $X_2$ may be C, and $X_3$ and $X_4$ may be N. Therefore, the highest occupied molecular orbital (HOMO) and the lowest unoccupied molecular orbital (LUMO) may be effectively separated within a molecule of the organometallic compound represented by Formula 1, thereby improving efficiency of an electronic device, for example, an organic light-emitting device including the compound represented by Formula 1.

In addition, $T_3$ in Formula 1 may be a group selected from *—O—*', *—S—*', *—C($R_7$)($R_8$)—*' *—C($R_7$)=*', *=C($R_7$)—*', *—C($R_7$)=C($R_8$)—*', *—C(=O)—*', *—C(=S)—*', *—C≡C—*', *—N($R_7$)—*', *—Si($R_7$)($R_8$)—*', and *—P($R_7$)($R_8$)—*', wherein * and *' in each of the foregoing groups independently indicate a binding site to a neighboring atom. That is, $T_3$ in Formula 1 may not be a single bond. Therefore, a self-quenching reduction group may be introduced to Formula 1 (that is, $T_3$ in Formula 1 may act as the self-quenching reduction group), thereby reducing a roll-off ratio of an electronic device, for example, an organic light-emitting device including the compound represented by Formula 1, and improving efficiency thereof.

For example, the HOMO, the LUMO, a singlet (Si) energy level, and a triplet ($T_1$) energy level of Compounds 1, 2, 3, 5, 8, 10, 12, 15, 36, 44, and 66 and Compounds A and B below were evaluated by using a Gaussian program density functional theory (DFT) method (the structure was optimized at B3LYP, 6-31G(d,p) level). Results thereof are shown in Table 1.

TABLE 1

| Compound No. | HOMO (eV) | LUMO (eV) | $S_1$ energy level (eV) | $T_1$ energy level (eV) |
|---|---|---|---|---|
| 1 | −4.440 | −1.636 | 2.233 | 2.028 |
| 2 | −4.405 | −1.607 | 2.224 | 2.021 |
| 3 | −4.478 | −1.680 | 2.221 | 2.020 |
| 5 | −4.475 | −1.677 | 2.220 | 2.019 |
| 8 | −4.446 | −1.647 | 2.220 | 2.019 |
| 10 | −4.369 | −1.625 | 2.184 | 1.985 |
| 12 | −4.374 | −1.639 | 2.170 | 1.974 |
| 15 | −4.400 | −1.634 | 2.214 | 1.985 |
| 36 | −4.378 | −1.716 | 2.136 | 1.965 |
| 44 | −4.332 | −1.599 | 2.152 | 1.964 |

TABLE 1-continued

| Compound No. | HOMO (eV) | LUMO (eV) | S₁ energy level (eV) | T₁ energy level (eV) |
|---|---|---|---|---|
| 66 | −4.532 | −1.921 | 2.082 | 1.879 |
| A | −4.782 | −1.521 | 2.678 | 2.443 |
| B | −4.704 | −2.538 | 1.662 | 1.485 |

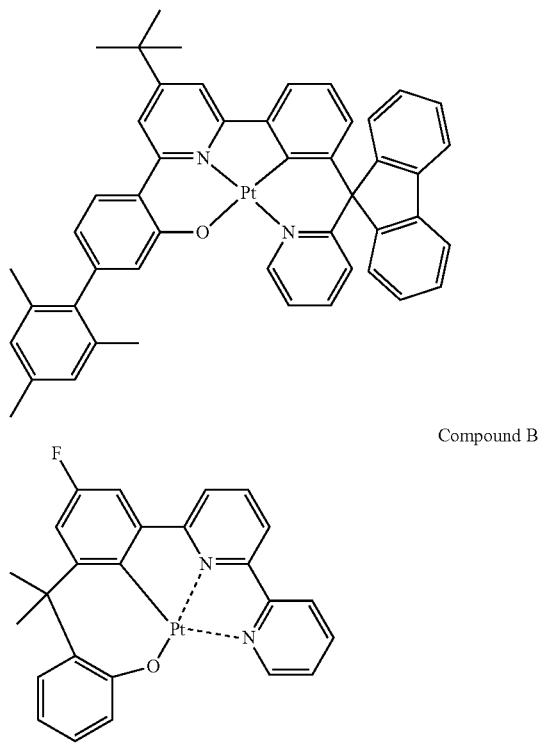

Compound A

Compound B

Based on the results of Table 1, it is determined that the organometallic compound represented by Formula 1 has electric characteristics that are suitable for use in an electronic device, for example, for use as a dopant of an organic light-emitting device.

Synthesis methods of the organometallic compound represented by Formula 1 may be recognizable by one of ordinary skill in the art by referring to Synthesis Examples provided below.

The organometallic compound represented by Formula 1 is suitable for use in an organic layer of an organic light-emitting device, for example, for use as a dopant in an emission layer of the organic layer. Thus, another aspect provides an organic light-emitting device that includes:

a first electrode;

a second electrode; and an organic layer that is disposed between the first electrode and the second electrode, wherein the organic layer includes an emission layer and at least one organometallic compound represented by Formula 1.

The organic light-emitting device may have, due to the inclusion of an organic layer including the organometallic compound represented by Formula 1, low driving voltage, high efficiency, high power, high quantum efficiency, a long lifespan, a low roll-off ratio, and excellent color purity.

The organometallic compound of Formula 1 may be used between a pair of electrodes of an organic light-emitting device. For example, the organometallic compound represented by Formula 1 may be included in the emission layer. In this regard, the organometallic compound may act as a dopant, and the emission layer may further include a host (that is, an amount of the organometallic compound represented by Formula 1 is smaller than an amount of the host).

The expression that "(an organic layer) includes at least one organometallic compound" as used herein may refer to an embodiment in which "(an organic layer) includes identical organometallic compounds represented by Formula 1 and an embodiment in which (an organic layer) includes two or more different organometallic compounds represented by Formula 1.

For example, the organic layer may include only Compound 1 as the organometallic compound. In this regard, Compound 1 may be included only in the emission layer of the organic light-emitting device. In one or more embodiments, the organic layer may include, as the organometallic compound, Compound 1 and Compound 2. In this regard, Compound 1 and Compound 2 may be included in the same layer (for example, Compound 1 and Compound 2 all may be included in an emission layer).

The first electrode may be an anode, which is a hole injection electrode, and the second electrode may be a cathode, which is an electron injection electrode; or the first electrode may be a cathode, which is an electron injection electrode, and the second electrode may be an anode, which is a hole injection electrode.

For example, regarding the organic light-emitting device, the first electrode may be an anode, and the second electrode may be a cathode, and the organic layer may further include a hole transport region disposed between the first electrode and the emission layer, and an electron transport region disposed between the emission layer and the second electrode, and the hole transport region may include a hole injection layer, a hole transport layer, an electron blocking layer, or any combination thereof, and the electron transport region may include a hole blocking layer, an electron transport layer, an electron injection layer, or any combination thereof.

The term "organic layer" as used herein refers to a single layer and/or a plurality of layers disposed between the first electrode and the second electrode of the organic light-emitting device. The "organic layer" may include, in addition to an organic compound, an organometallic complex including a metal.

FIGURE is a schematic view of an organic light-emitting device 10 according to an embodiment. Hereinafter, the structure of an organic light-emitting device according to an embodiment and a method of manufacturing an organic light-emitting device according to an embodiment will be described in connection with FIGURE. The organic light-emitting device 10 includes a first electrode 11, an organic layer 15, and a second electrode 19, which are sequentially stacked in this stated order.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water-resistance.

The first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode 11 may be, for example, indium tin oxide (ITO), indium zinc oxide (IZO), tin oxide ($SnO_2$), and zinc oxide (ZnO). In one or more embodiments, magnesium (Mg), aluminum (Al), aluminum-lithium (Al—Li), calcium (Ca), magnesium-indium (Mg—In), or magnesium-silver (Mg—Ag) may be used as the material for forming the first electrode 11.

The first electrode 11 may have a single-layered structure or a multi-layered structure including two or more layers. For example, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include a hole injection layer, a hole transport layer, an electron blocking layer, a buffer layer, or any combination thereof.

The hole transport region may include only either a hole injection layer or a hole transport layer. In one or more embodiments, the hole transport region may have a structure of hole injection layer/hole transport layer or hole injection layer/hole transport layer/electron blocking layer, which are sequentially stacked in this stated order from the first electrode 11.

A hole injection layer may be formed on the first electrode 11 by using one or more suitable methods selected from vacuum deposition, spin coating, casting, or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100° C. to about 500° C., a vacuum pressure of about $10^{-8}$ torr to about $10^{-3}$ torr, and a deposition rate of about 0.01 Å/sec to about 100 Å/sec. However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrene sulfonate) (PEDOT/PSS), polyaniline/camphor sulfonic acid (Pani/CSA), polyaniline/poly(4-styrene sulfonate) (Pani/PSS), a compound represented by Formula 201 below, and a compound represented by Formula 202 below:

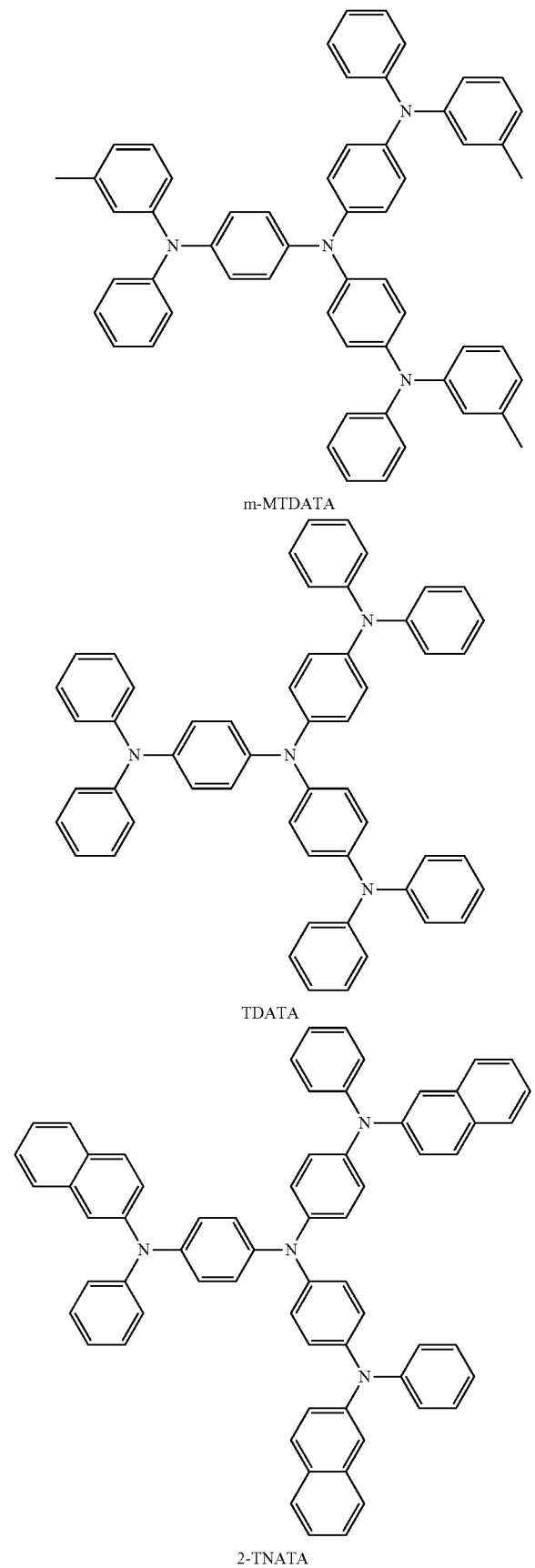

m-MTDATA

TDATA

2-TNATA

-continued
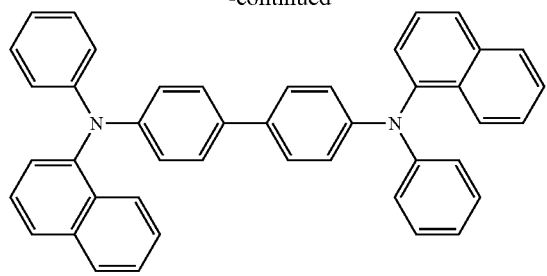
NPB
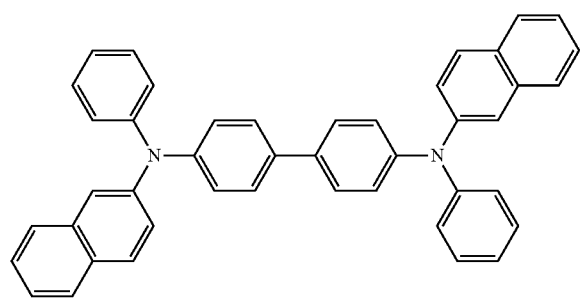
β-NPB
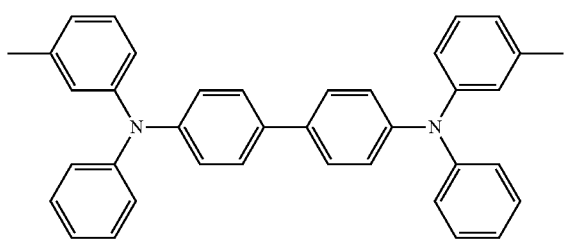
TPD
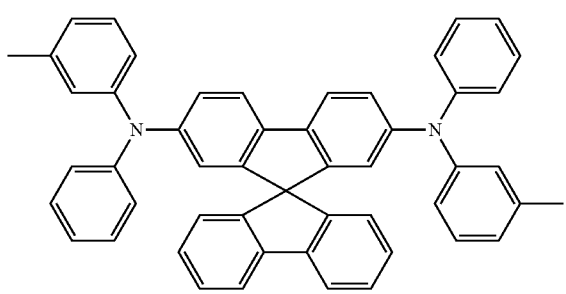
Spiro-TPD
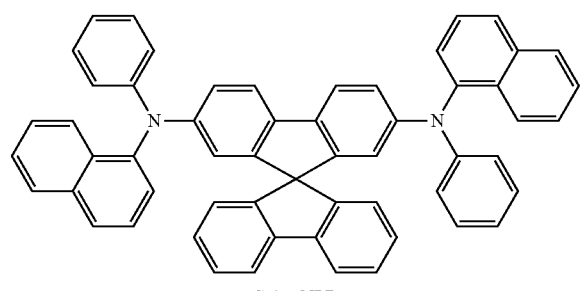
Spiro-NPB
-continued
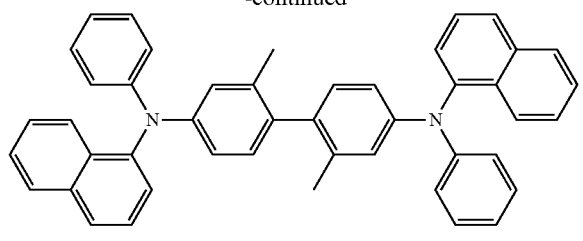
methylated NPB
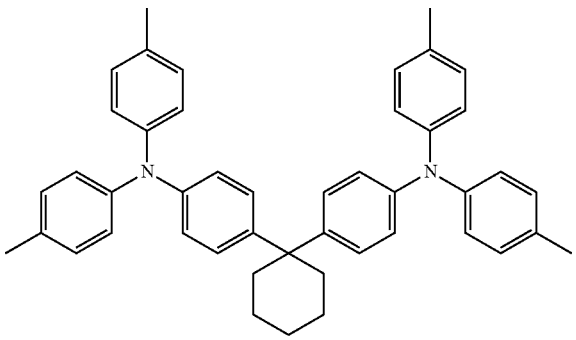
TAPC
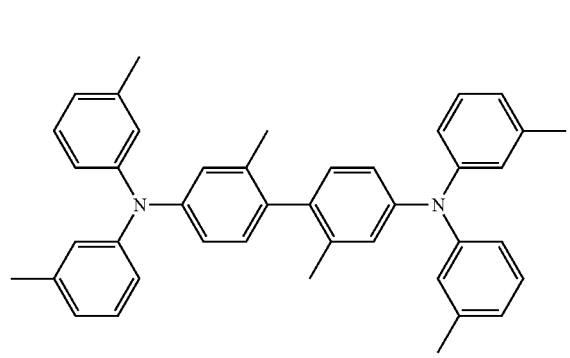
HMTPD
Formula 201
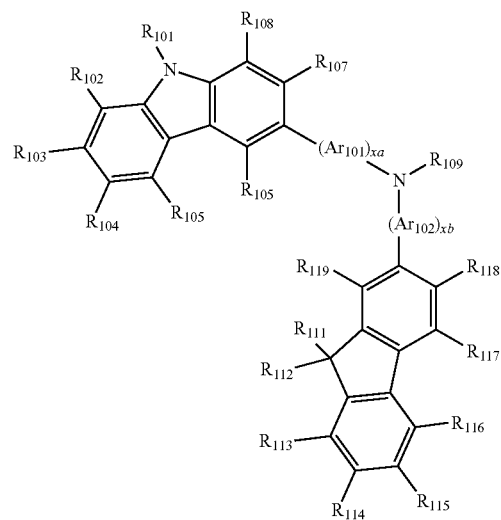

Formula 202

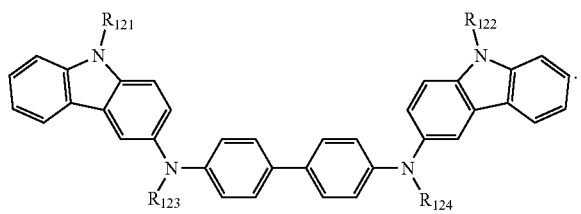

Ar$_{101}$ and Ar$_{102}$ in Formula 201 may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may each independently be an integer selected from 0 to 5, or 0, 1, or 2. For example, xa is 1 and xb is 0, but xa and xb are not limited thereto.

R$_{101}$ to R$_{108}$, R$_{111}$ to R$_{119}$, and R$_{121}$ to R$_{124}$ in Formulae 201 and 202 may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and so on), and a $C_1$-$C_{10}$ alkoxy group (for example, a methoxy group, an ethoxy group, a propoxy group, a butoxy group, a pentoxy group, and so on);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group and $C_1$-$C_{10}$ alkoxy group, but are not limited thereto.

R$_{109}$ in Formula 201 may be selected from:

a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In one or more embodiments, the compound represented by Formula 201 may be represented by Formula 201A, but is not limited thereto:

Formula 201A

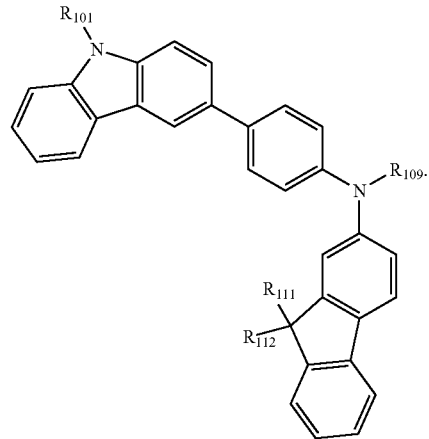

R$_{101}$, R$_{111}$, R$_{112}$, and R$_{109}$ in Formula 201A may be the same as described above.

For example, the compound represented by Formula 201, and the compound represented by Formula 202 may include compounds HT1 to HT20 illustrated below, but are not limited thereto:

HT1

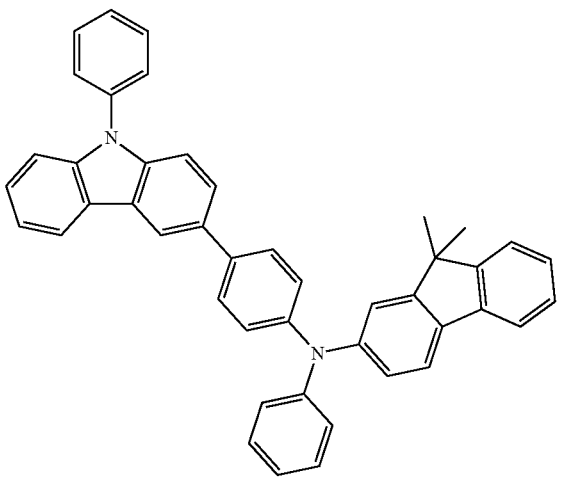

HT2
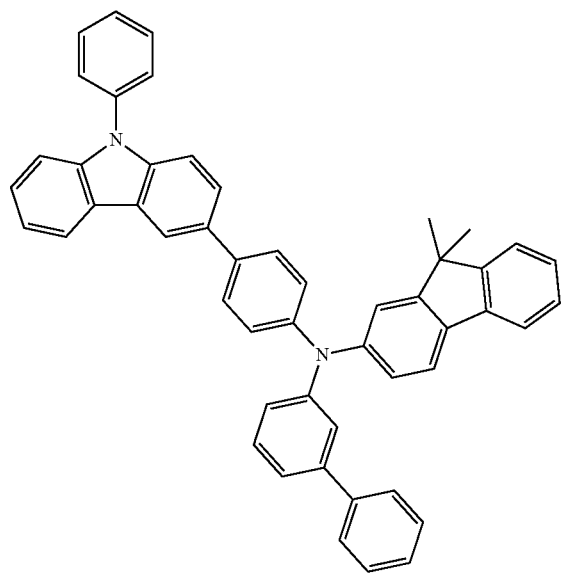
HT4
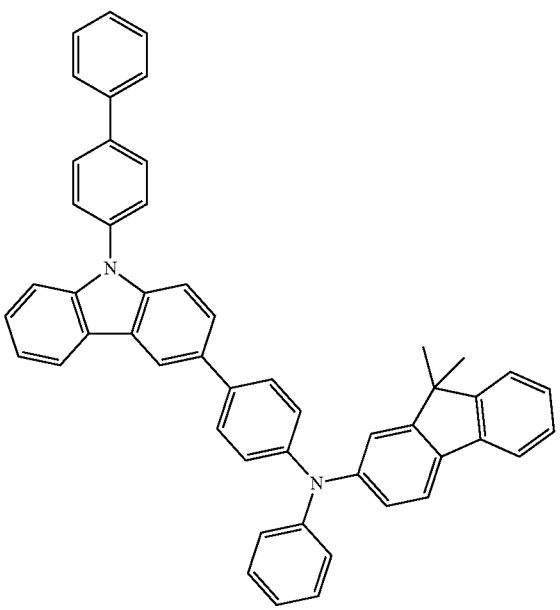
HT3
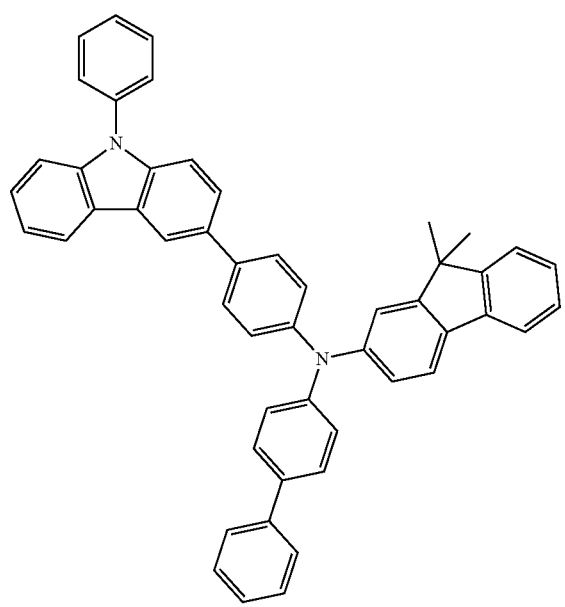
HT5
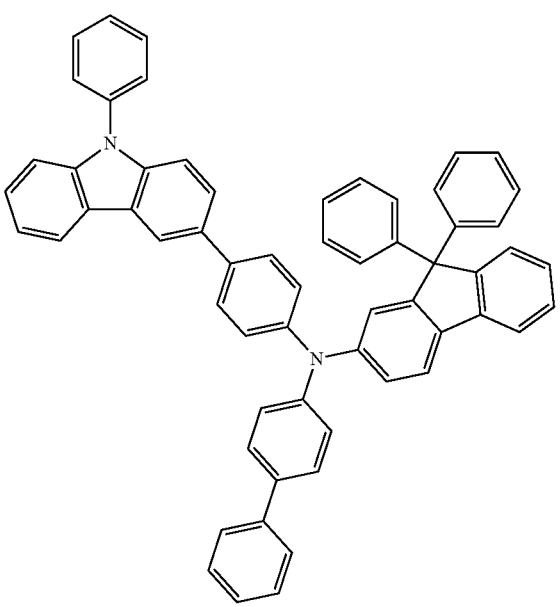

HT6
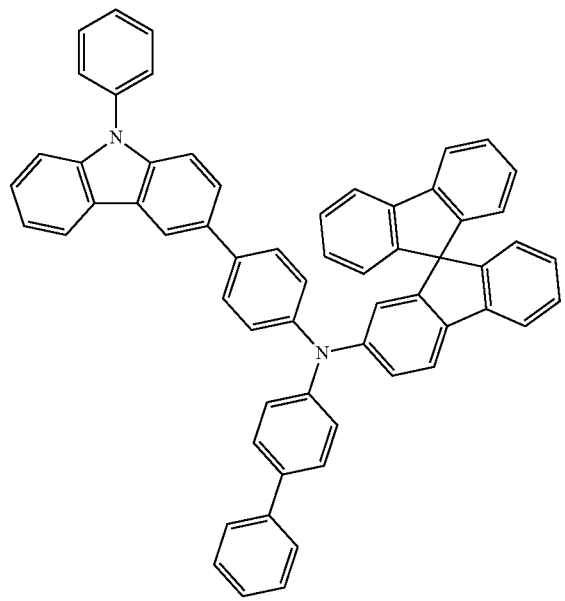
HT8
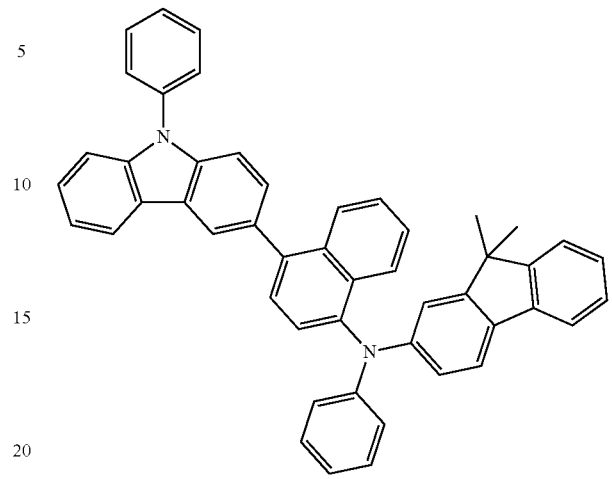
HT9
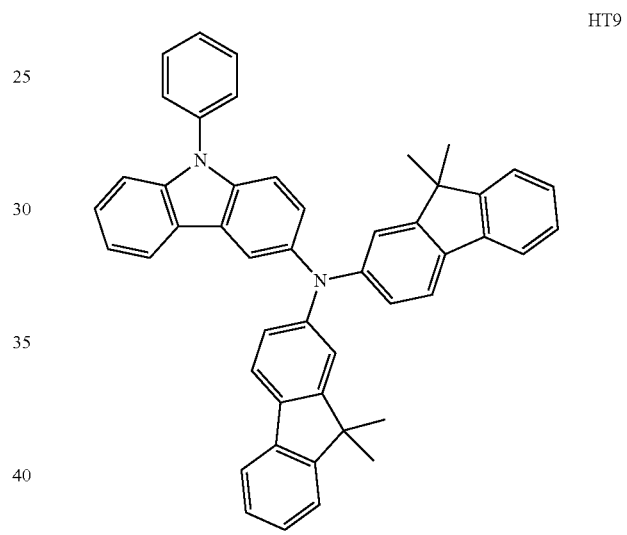
HT7
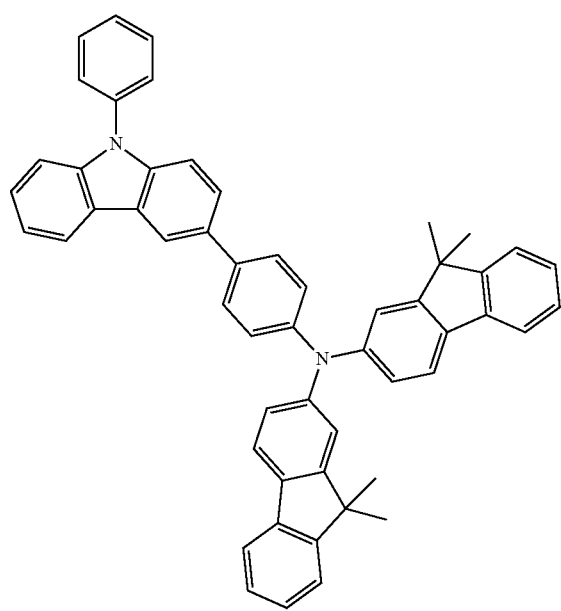
HT10
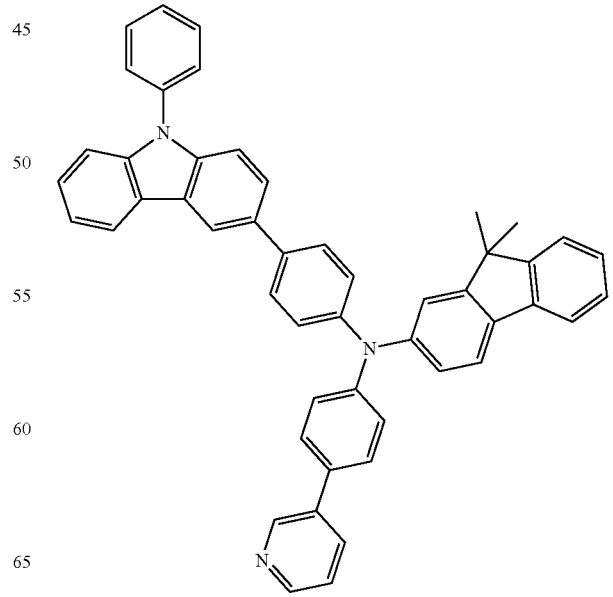

HT11
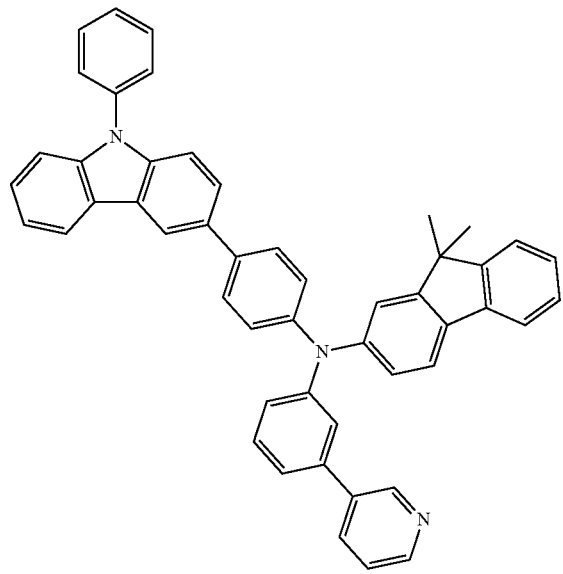
HT12
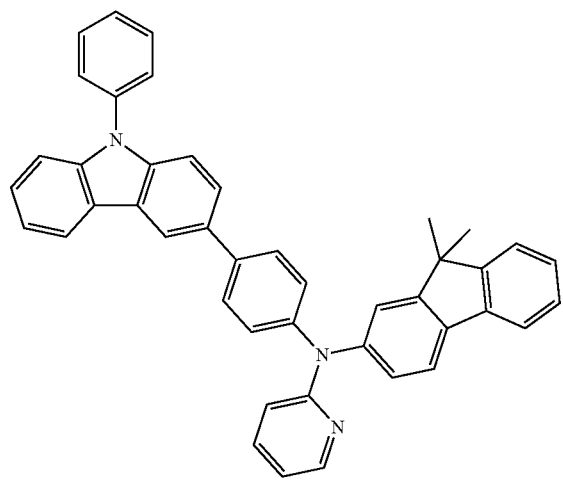
HT13
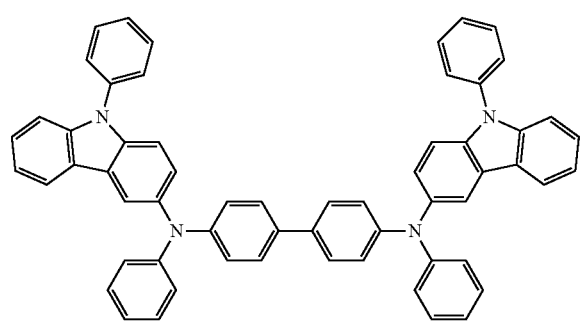
HT14
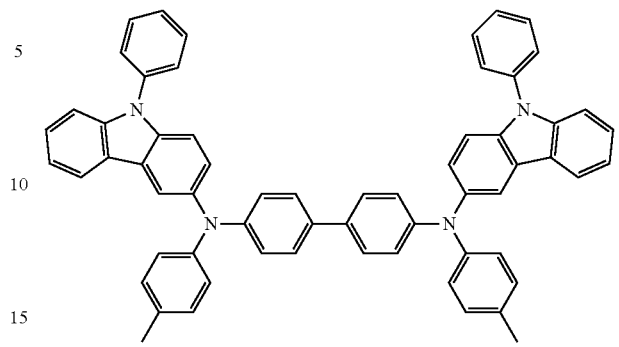
HT15
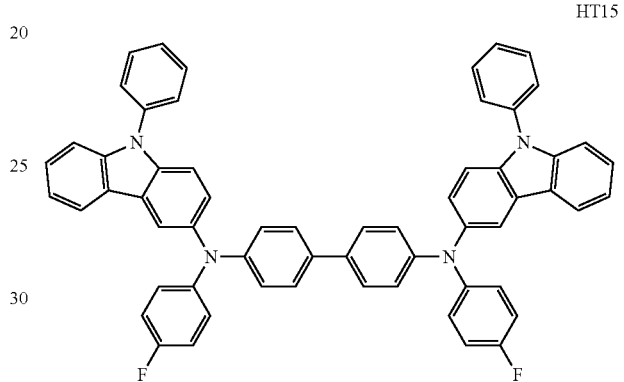
HT16
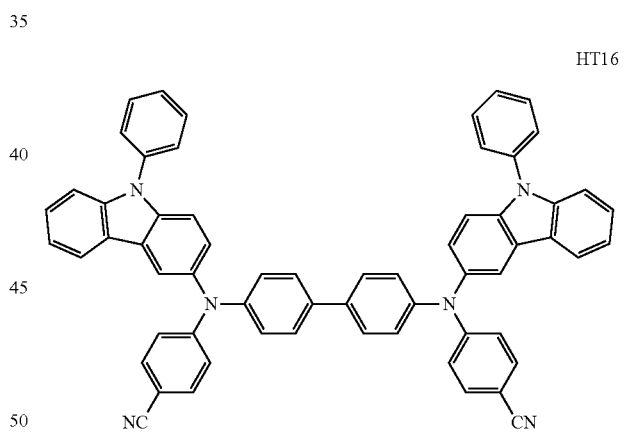
HT17
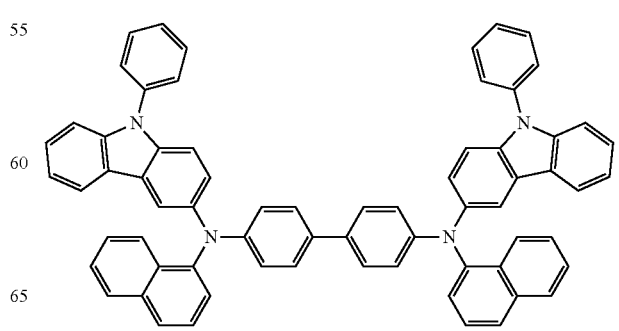

-continued

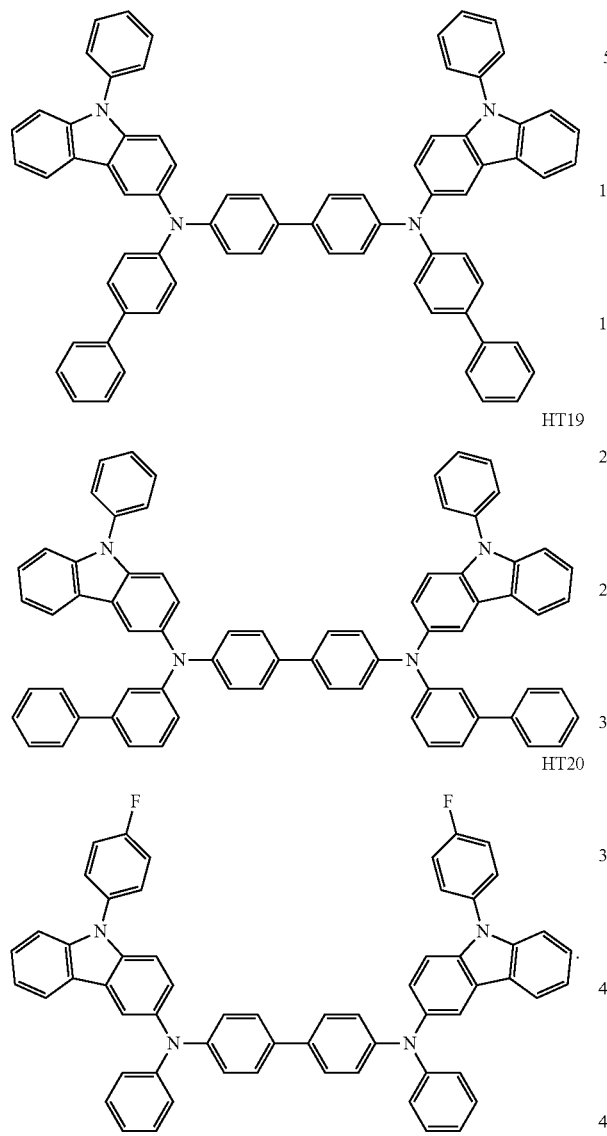

A thickness of the hole transport region may be in a range of about 100 Å to about 10,000 Å, for example, about 100 Å to about 1,000 Å. While not wishing to be bound by theory, it is understood that when the hole transport region includes at least one of a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant include a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 below, but are not limited thereto:

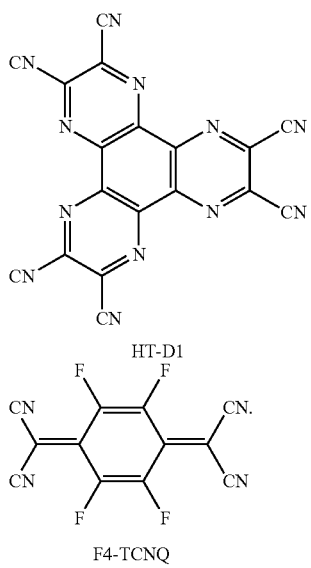

The hole transport region may include a buffer layer.

Also, the buffer layer may compensate for an optical resonance distance according to a wavelength of light emitted from the emission layer, and thus, the efficiency of a formed organic light-emitting device may be improved.

Then, an emission layer may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

Meanwhile, when the hole transport region includes an electron blocking layer, a material for the electron blocking layer may be selected from materials for the hole transport region described above and materials for a host to be explained later. However, the material for the electron blocking layer is not limited thereto. For example, when the hole transport region includes an electron blocking layer, a material for the electron blocking layer may be mCP, which will be explained later.

The emission layer may include a host and a dopant, and the dopant may include the organometallic compound represented by Formula 1.

The host may include at least one selected from TPBi, TBADN, ADN (also referred to as "DNA"), CBP, CDBP, TCP, mCP, Compound H50, and Compound H51:

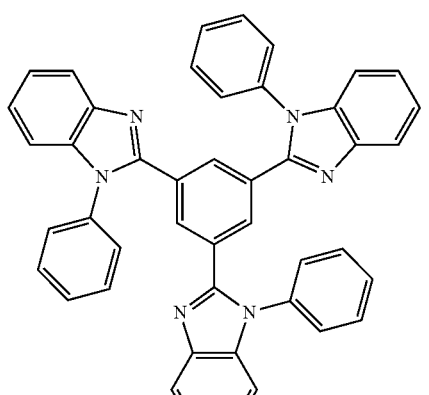
TPBi
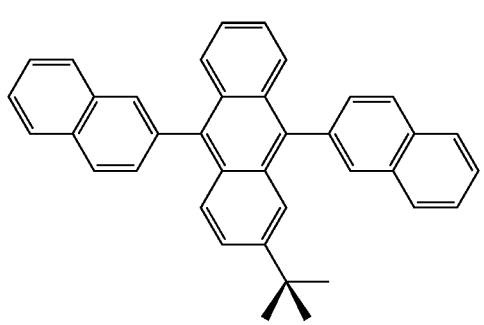
TBADN
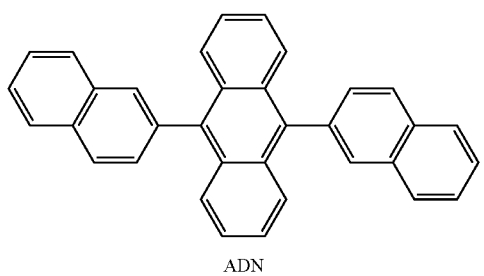
ADN
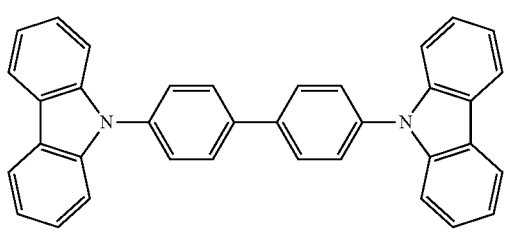
CBP
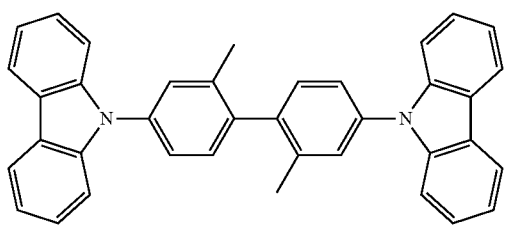
CDBP
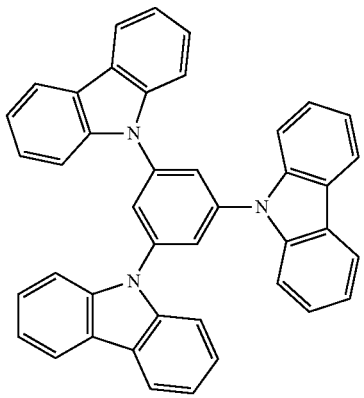
TCP
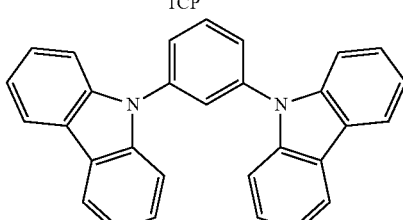
mCP
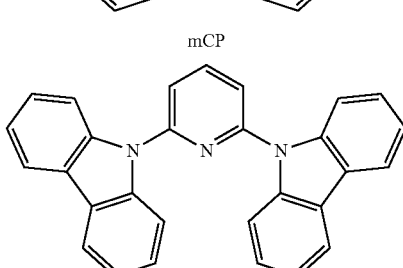
H50
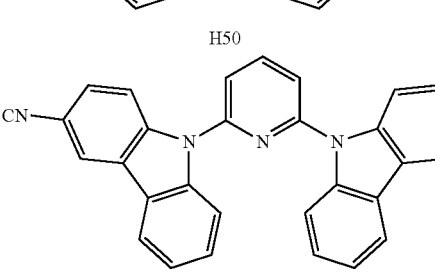
H51
In one or more embodiments, the host may further include a compound represented by Formula 301 below.
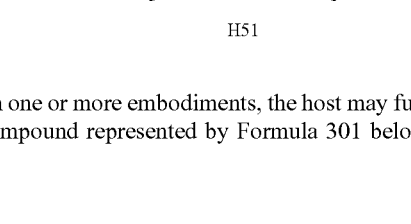
Formula 301
$Ar_{111}$ and $Ar_{112}$ in Formula 301 may each independently be selected from:

a phenylene group, a naphthylene group, a phenanthrenylene group, and a pyrenylene group; and a phenylene group, a naphthylene group, a phenanthrenylene group, and a pyrenylene group, each substituted with at least one selected from a phenyl group, a naphthyl group, and an anthracenyl group.

$Ar_{113}$ to $Ar_{116}$ in Formula 301 may each independently be selected from:

a $C_1$-$C_{10}$ alkyl group, a phenyl group, a naphthyl group, a phenanthrenyl group, and a pyrenyl group; and a phenyl group, a naphthyl group, a phenanthrenyl group, and a pyrenyl group, each substituted with at least one selected from a phenyl group, a naphthyl group, and an anthracenyl group.

g, h, i, and j in Formula 301 may each independently be an integer selected from 0 to 4, and may be, for example, 0, 1, or 2.

$Ar_{113}$ to $Ar_{116}$ in Formula 301 may each independently be selected from:

a $C_1$-$C_{10}$ alkyl group, substituted with at least one selected from a phenyl group, a naphthyl group, and an anthracenyl group;

a phenyl group, a naphthyl group, an anthracenyl group, a pyrenyl group, a phenanthrenyl group, and a fluorenyl group;

a phenyl group, a naphthyl group, an anthracenyl group, a pyrenyl group, a phenanthrenyl group, and a fluorenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group; and but embodiments are not limited thereto.

In one or more embodiments, the host may include a compound represented by Formula 302 below:

Formula 302

$Ar_{122}$ to $Ar_{125}$ in Formula 302 are the same as described in detail in connection with $Ar_{113}$ in Formula 301.

$Ar_{126}$ and $Ar_{127}$ in Formula 302 may each independently be a $C_1$-$C_{10}$ alkyl group (for example, a methyl group, an ethyl group, or a propyl group).

k and l in Formula 302 may each independently be an integer selected from 0 to 4. For example, k and l may be 0, 1, or 2.

The compound represented by Formula 301 and the compound represented by Formula 302 may include Compounds H1 to H42 illustrated below, but are not limited thereto:

H1

H2

H3

H4

H5

H6

-continued
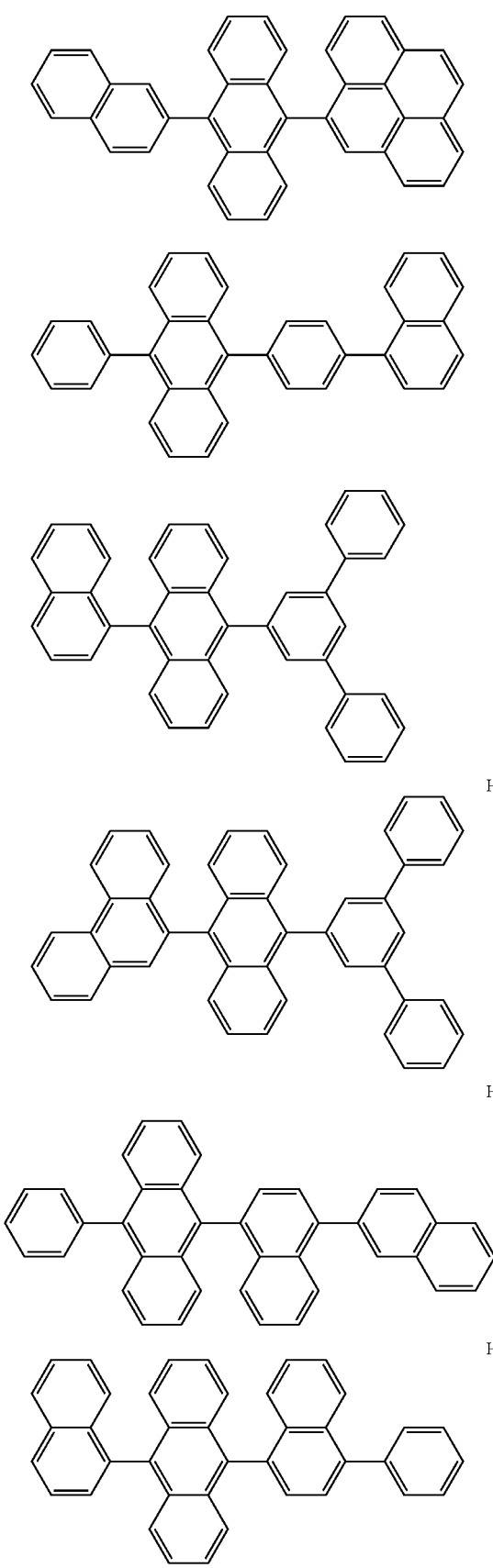
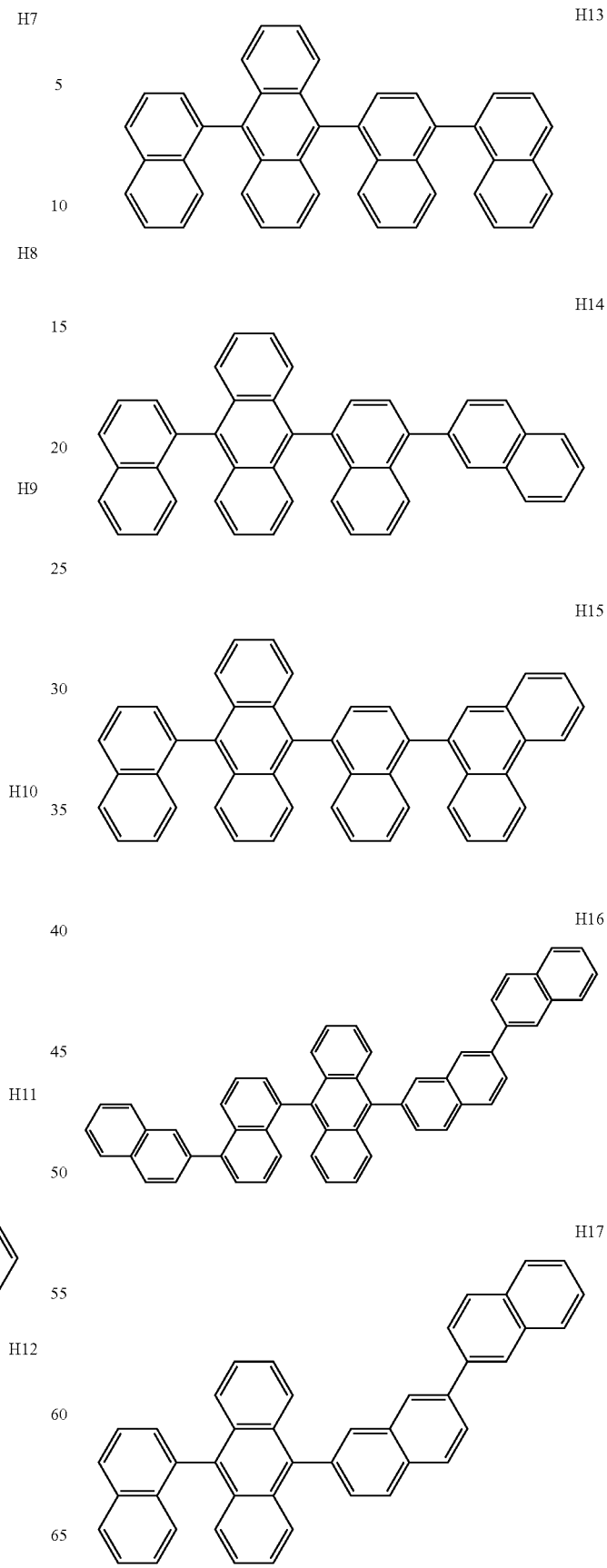

-continued
H18
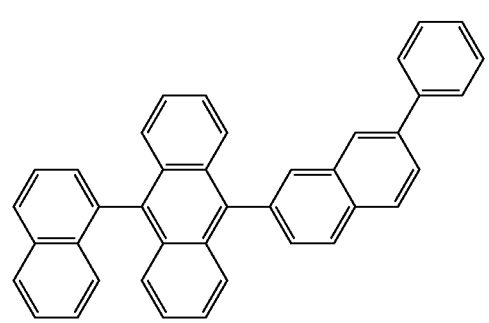
H19
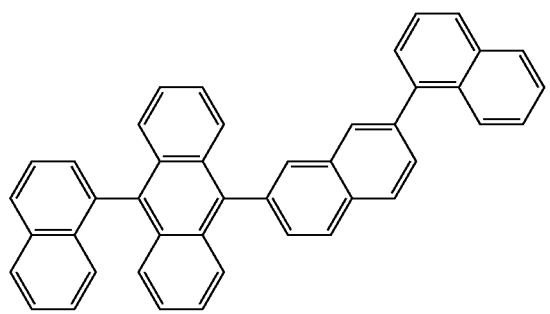
H20
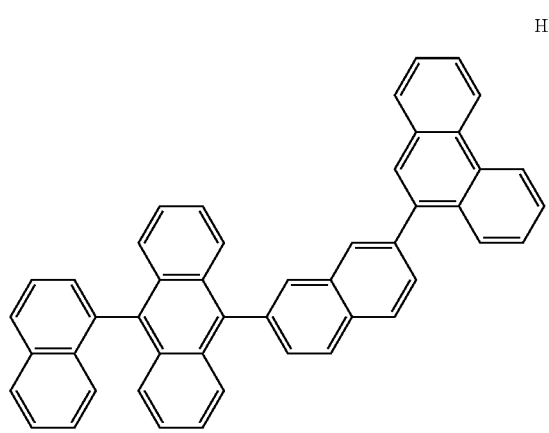
H21
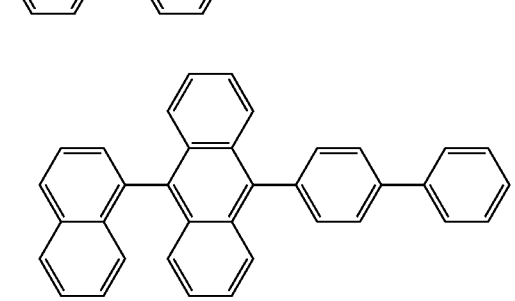
H22
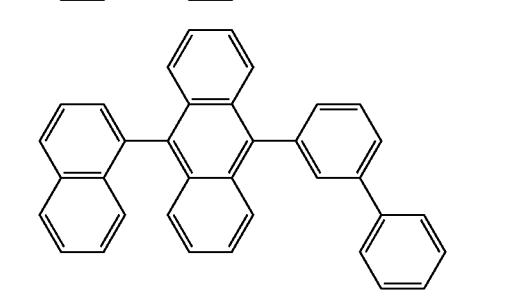
-continued
H23
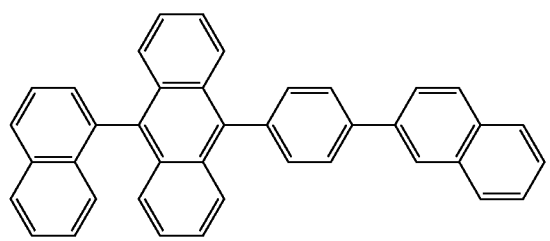
H24
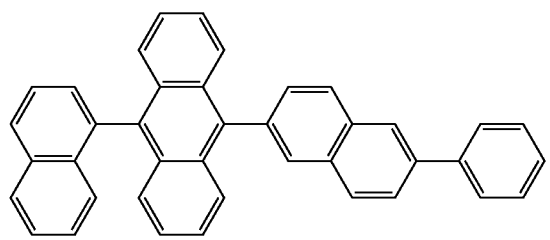
H25
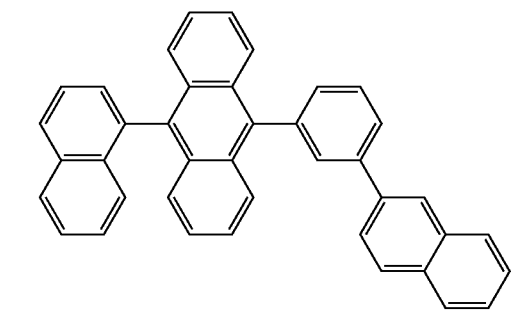
H26
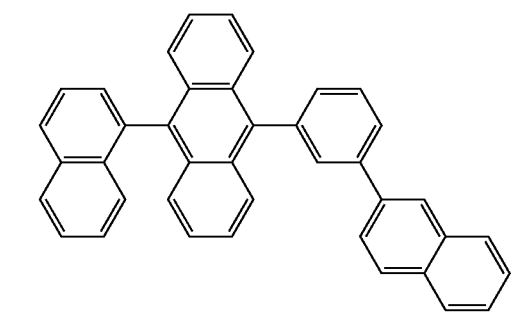
H27
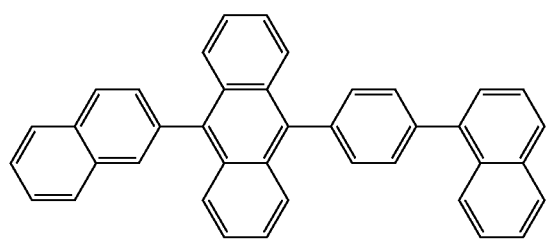

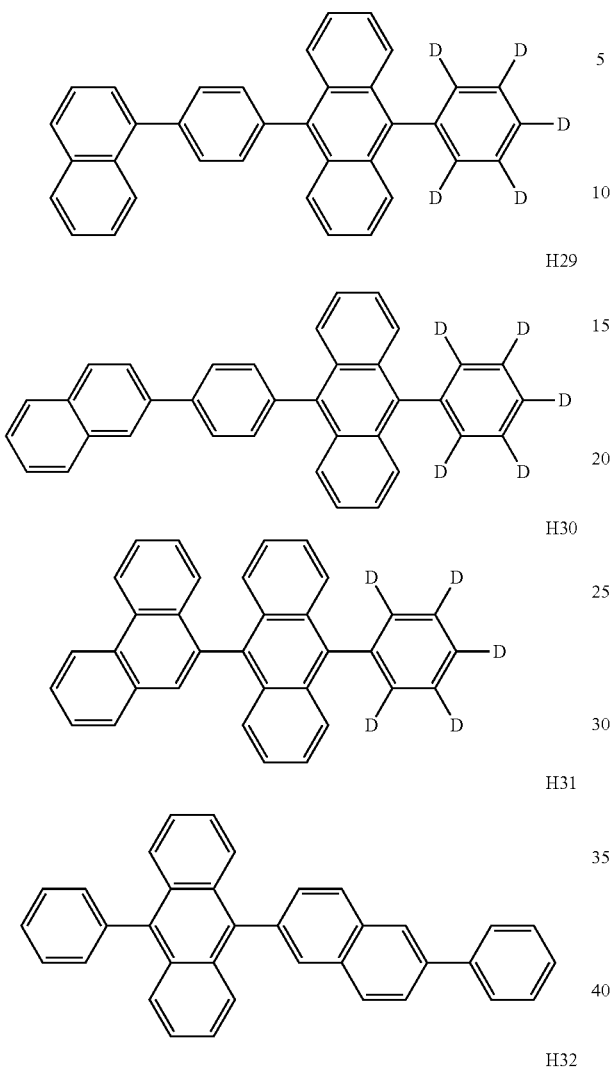
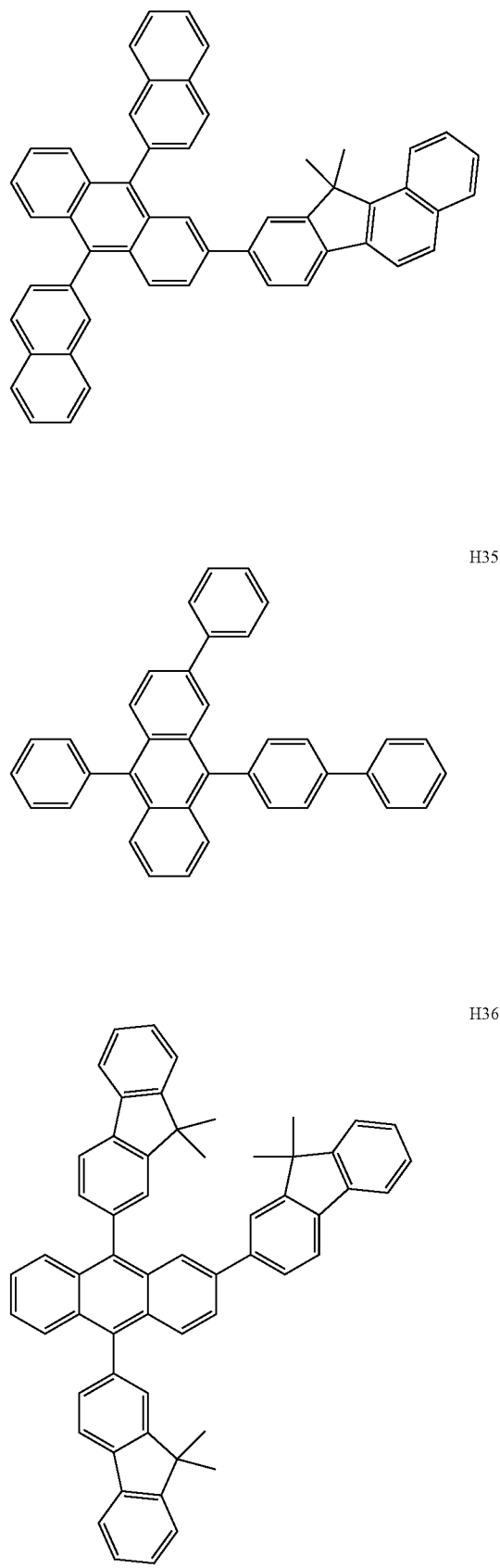

H37
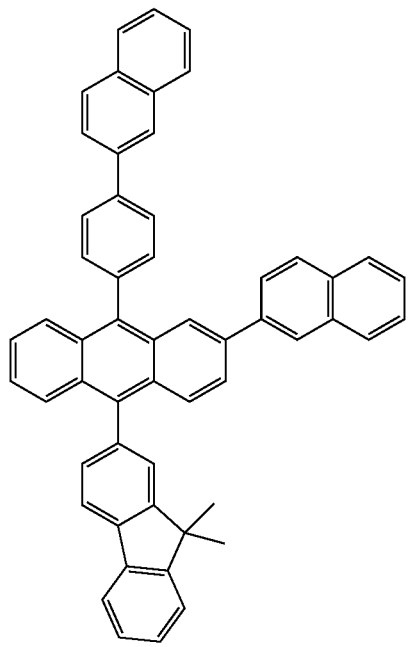
H38
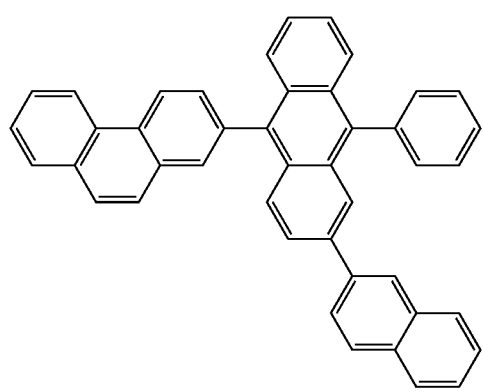
H39
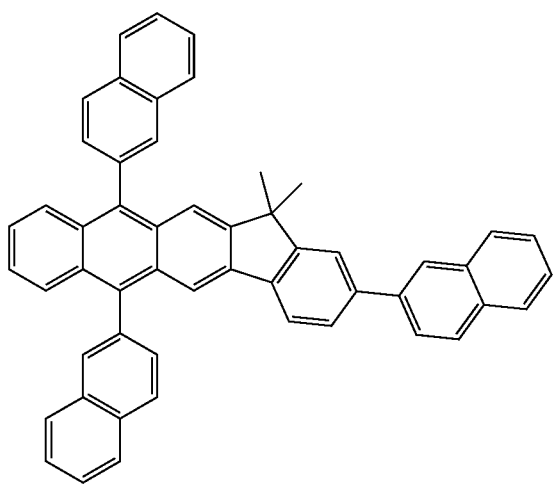
H40
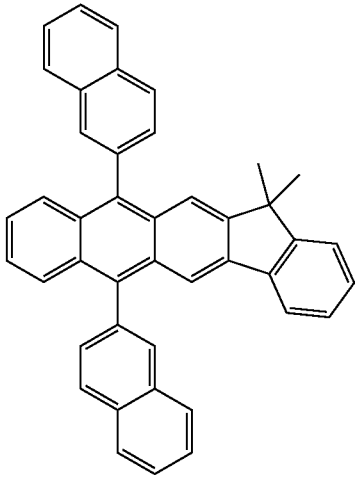
H41
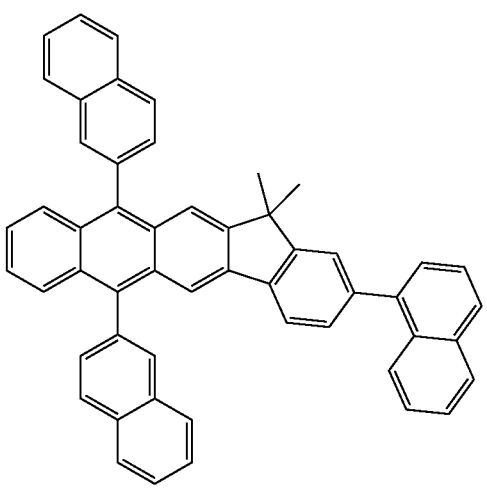
H42
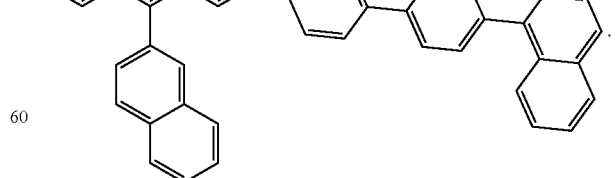
When the organic light-emitting device is a full-color organic light-emitting device, the emission layer may be patterned into a red emission layer, a green emission layer, and a blue emission layer. In one or more embodiments, due to a stack structure including a red emission layer, a green emission layer, and/or a blue emission layer, the emission layer may emit white light.

When the emission layer includes a host and a dopant, an amount of the dopant may be in a range of about 0.01 parts to about 15 parts by weight based on 100 parts by weight of the host, but is not limited thereto.

A thickness of the emission layer may be in a range of about 100 Å to about 1,000 Å, for example, about 200 Å to about 600 Å. While not wishing to be bound by theory, it is understood that when the thickness of the emission layer is within the above ranges, excellent light-emission characteristics may be obtained without a substantial increase in driving voltage.

Then, an electron transport region may be disposed on the emission layer.

The electron transport region may include a hole blocking layer, an electron transport layer, an electron injection layer, or any combination thereof.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP, Bphen, and BAlq, but is not limited thereto:

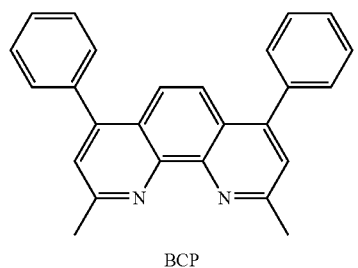

BCP

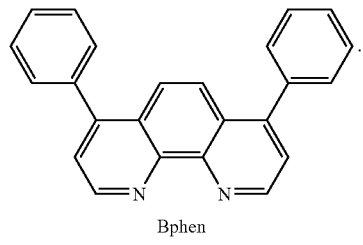

Bphen

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have improved hole blocking ability without a substantial increase in driving voltage.

The electron transport layer may further include at least one selected from BOP, Bphen, $Alq_3$, BAlq, TAZ, and NTAZ:

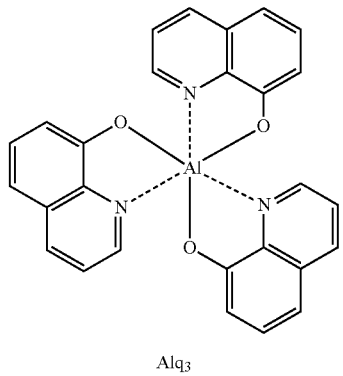

$Alq_3$

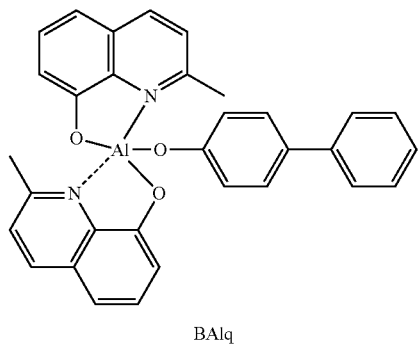

BAlq

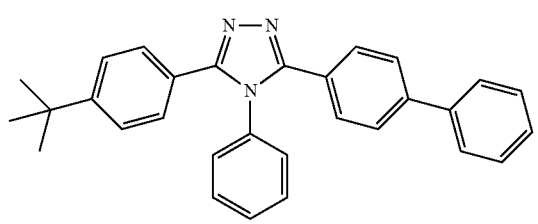

TAZ

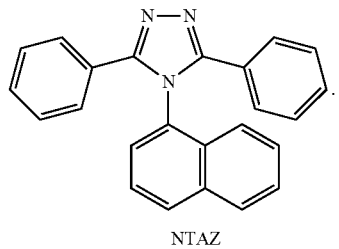

NTAZ

In one or more embodiments, the electron transport layer may include at least one of ET1 and ET2, but are not limited thereto:

ET1

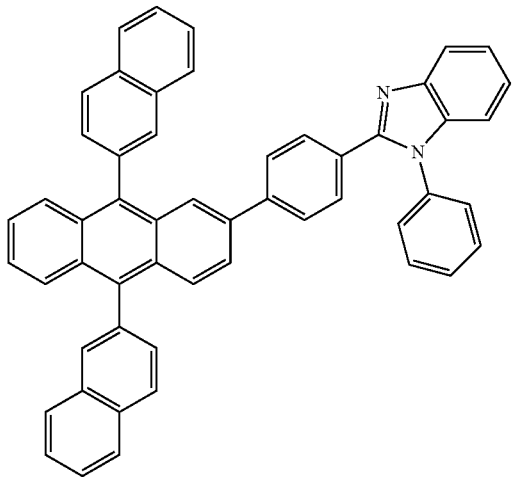

ET2

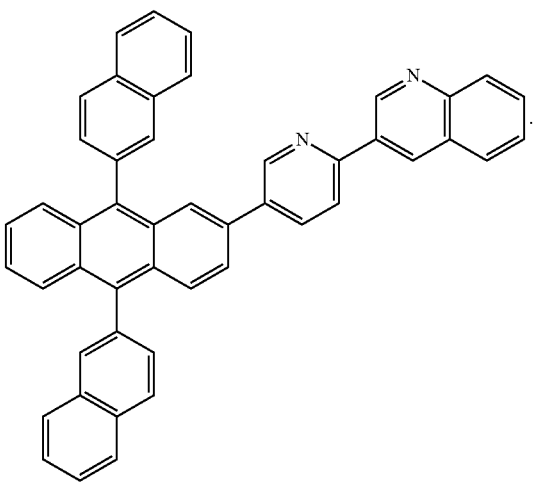

A thickness of the electron transport layer may be in a range of about 100 Å to about 1,000 Å, for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2:

ET-D1

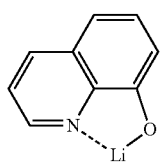

ET-D2

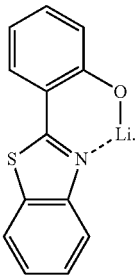

The electron transport region may include an electron injection layer (EIL) that promotes flow of electrons from the second electrode 19 thereinto.

The electron injection layer may include at least one selected from, LiF, NaCl, CsF, $Li_2O$, BaO, and LiQ.

A thickness of the electron injection layer may be in a range of about 1 Å to about 100 Å, for example, about 3 Å to about 90 Å. While not wishing to be bound by theory, it is understood that when the thickness of the electron injection layer is within the ranges described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be selected from metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be used as a material for forming the second electrode 19. In one or more embodiments, to manufacture a top emission type light-emitting device, a transmissive electrode formed using ITO or IZO may be used as the second electrode 19.

Hereinbefore, the organic light-emitting device has been described with reference to FIGURE, but is not limited thereto.

Another aspect of the present disclosure provides a diagnosis composition including at least one organometallic compound represented by Formula 1.

The organometallic compound represented by Formula 1 may provide high luminescent efficiency. Accordingly, a diagnosis composition including the organometallic compound may have high diagnosis efficiency.

Such a diagnosis composition may be used in various applications including diagnosis kits, diagnosis reagents, biosensors, biomarkers, etc.

The term "$C_1$-$C_{60}$ alkyl group," as used herein, refers to a linear or branched aliphatic saturated hydrocarbon monovalent group having 1 to 60 carbon atoms, and examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group," as used herein, refers to a divalent group having the same structure as the $C_1$-$C_{60}$ alkyl group.

The term "$C_1$-$C_{60}$ alkoxy group," as used herein, refers to a monovalent group represented by —$OA_{101}$ (wherein $A_{101}$ is the $C_1$-$C_{60}$ alkyl group), and non-limiting examples thereof include a methoxy group, an ethoxy group, and an iso-propyloxy (iso-propoxy) group.

The term "$C_2$-$C_{60}$ alkenyl group," as used herein, refers to a hydrocarbon group formed by including at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group," as used herein, refers to a divalent group having the same structure as the $C_2$-$C_{60}$ alkenyl group.

The term "$C_2$-$C_{60}$ alkynyl group," as used herein, refers to a hydrocarbon group formed by including at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group," as used herein, refers to a divalent group having the same structure as the $C_2$-$C_{60}$ alkynyl group.

The term "$C_3$-$C_{10}$ cycloalkyl group," as used herein, refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having the same structure as the $C_3$-$C_{10}$ cycloalkyl group.

The term "$C_1$-$C_{10}$ heterocycloalkyl group," as used herein, refers to a monovalent saturated monocyclic group having at least one heteroatom selected from N, O, P, Si, and S as a ring-forming atom and 1 to 10 carbon atoms, and non-limiting examples thereof include a tetrahydrofuranyl group and a tetrahydrothiophenyl group. The term "$C_1$-$C_{10}$ heterocycloalkylene group," as used herein, refers to a divalent group having the same structure as the $C_1$-$C_{10}$ heterocycloalkyl group.

The term "$C_3$-$C_{10}$ cycloalkenyl group," as used herein, refers to a monovalent monocyclic group that has 3 to 10 carbon atoms, at least one carbon-carbon double bond in the ring thereof, and which is not aromatic in the entire molecular structure. Non-limiting examples thereof include a cyclopentenyl group, a cyclohexenyl group, and a cycloheptenyl group. The term "$C_3$-$C_{10}$ cycloalkenylene group," as used herein, refers to a divalent group having the same structure as the $C_3$-$C_{10}$ cycloalkenyl group.

The term "$C_1$-$C_{10}$ heterocycloalkenyl group," as used herein, refers to a monovalent monocyclic group that has at least one heteroatom selected from N, O, P, Si, and S as a ring-forming atom, 1 to 10 carbon atoms, and at least one carbon-carbon double bond in its ring. Non-limiting examples of the $C_1$-$C_{10}$ heterocycloalkenyl group include a 2,3-dihydrofuranyl group and a 2,3-dihydrothiophenyl group. The term "$C_1$-$C_{10}$ heterocycloalkenylene group," as used herein, refers to a divalent group having the same structure as the $C_1$-$C_{10}$ heterocycloalkenyl group.

The term "$C_6$-$C_{60}$ aryl group," as used herein, refers to a monovalent group having a carbocyclic aromatic system having 6 to 60 carbon atoms, and the term "$C_6$-$C_{60}$ arylene group," as used herein, refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group," as used herein, refers to a monovalent group having a heterocyclic aromatic system that has at least one heteroatom selected from N, O, P, Si, and S as a ring-forming atom, and 1 to 60 carbon atoms. The term "$C_1$-$C_{60}$ heteroarylene group," as used herein refers to a divalent group having a heterocyclic aromatic system that has at least one heteroatom selected from N, O, P, Si, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group, as used herein, indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

The term "monovalent non-aromatic condensed polycyclic group," as used herein, refers to a monovalent group (for example, having 8 to 60 carbon atoms) that has two or more rings condensed to each other, only carbon atoms as a ring-forming atom, and which is non-aromatic in the entire molecular structure. Examples of the monovalent non-aromatic condensed polycyclic group include a fluorenyl group. The term "divalent non-aromatic condensed polycyclic group," as used herein, refers to a divalent group having the same structure as the monovalent non-aromatic condensed polycyclic group.

The term "monovalent non-aromatic condensed heteropolycyclic group," as used herein, refers to a monovalent group (for example, having 2 to 60 carbon atoms) that has two or more rings condensed to each other, has a heteroatom selected from N, O, P, Si, and S, other than carbon atoms, as a ring-forming atom, and which is non-aromatic in the entire molecular structure. Non-limiting examples of the monovalent non-aromatic condensed heteropolycyclic group include a carbazolyl group. The term "divalent non-aromatic condensed heteropolycyclic group," as used herein, refers to a divalent group having the same structure as the monovalent non-aromatic condensed heteropolycyclic group.

The term "$C_5$-$C_{30}$ carbocyclic group," as used herein, refers to a saturated or unsaturated cyclic group having 5 to 30 carbons as a ring-forming atom. Examples of the $C_5$-$C_{30}$ carbocyclic group include a monocyclic group and a polycyclic group.

The term "$C_1$-$C_{30}$ heterocyclic group," as used herein, refers to a saturated or unsaturated cyclic group having, at least one heteroatom selected from N, O, P, Si, and S, other than 1 to 30 carbons, as a ring-forming atom. Examples of the $C_1$-$C_{30}$ heterocyclic group include a monocyclic group and a polycyclic group.

At least one of substituents of the substituted $C_5$-$C_{30}$ carbocyclic group, substituted $C_2$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, and —$P(=O)(Q_{18})(Q_{19})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Br, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$, and —$P(=O)(Q_{28})(Q_{29})$; and —$N(Q_{31})(Q_{32})$, —$Si(Q_{33})(Q_{34})(Q_{35})$, —$B(Q_{36})(Q_{37})$, and —$P(=O)(Q_{38})(Q_{39})$, wherein $Q_{11}$ to $Q_{19}$, $Q_{21}$ to $Q_{29}$, and $Q_{31}$ to $Q_{39}$ may each independently be selected from hydrogen, deuterium, —F, —Br, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

When a group containing a specified number of carbon atoms is substituted with any of the groups listed in the preceding paragraphs, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{60}$ alkyl" refers to a $C_1$-$C_{60}$ alkyl group substituted with $C_6$-$C_{60}$ aryl group, the total number of carbon atoms in the resulting aryl substituted alkyl group is $C_7$-$C_{120}$.

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount of A used was identical to an amount of B used, in terms of a molar equivalent.

EXAMPLE

Synthesis Example 1: Synthesis of Compound 2

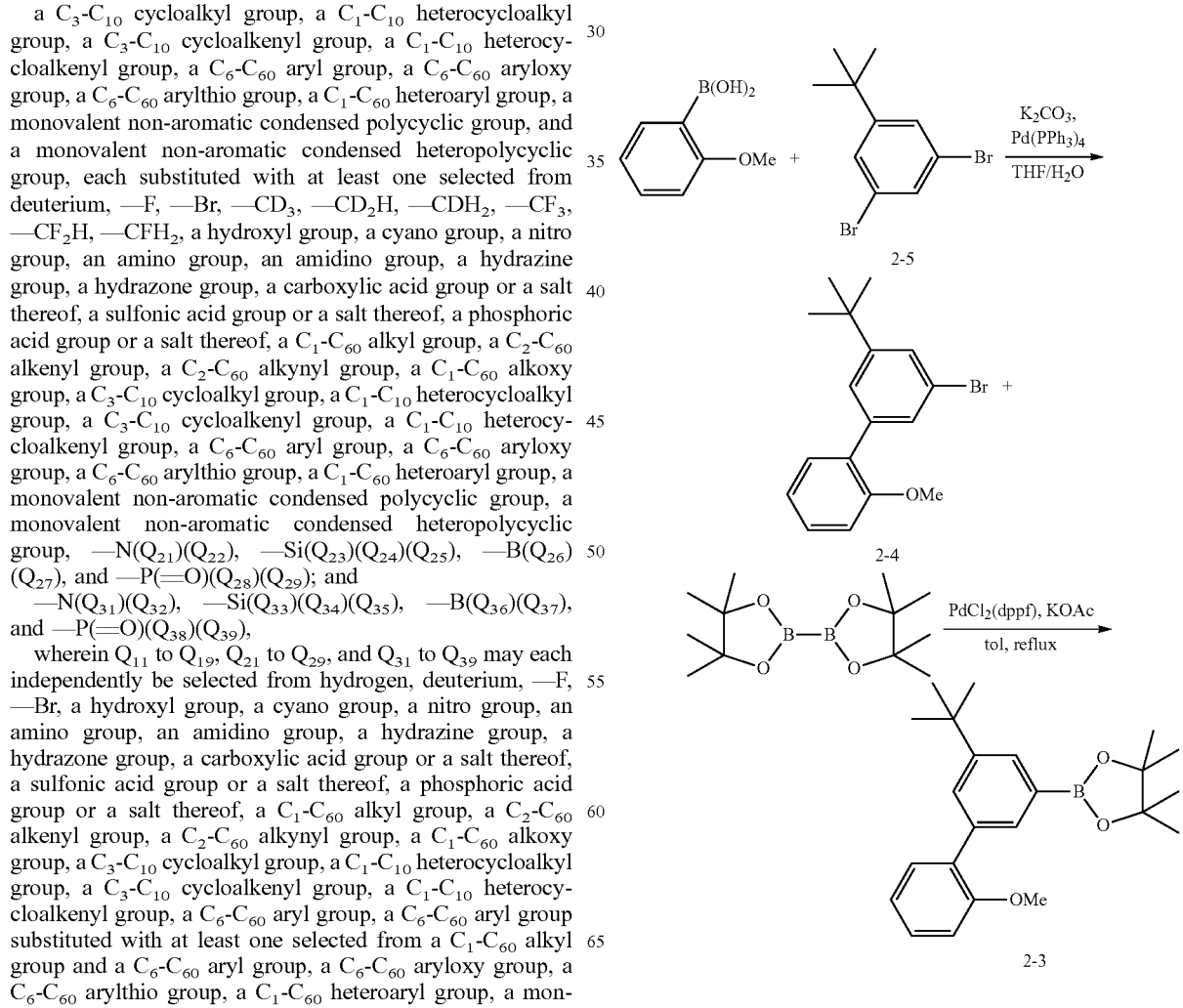

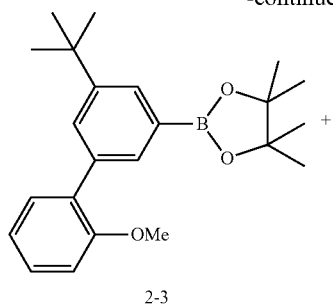

2-3

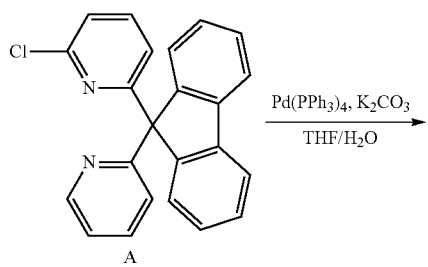

A

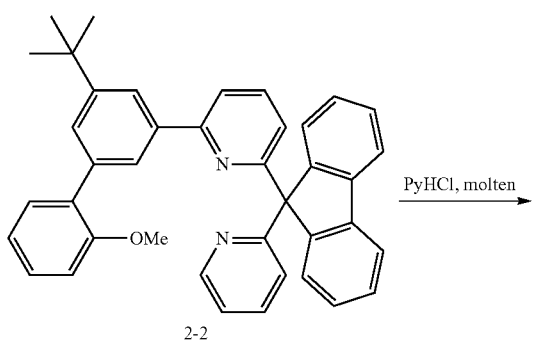

2-2

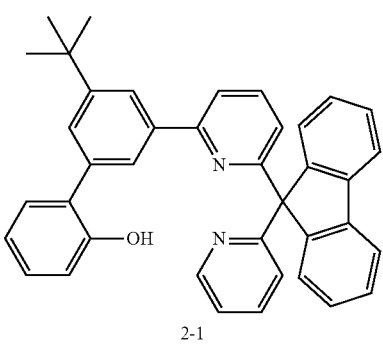

2-1

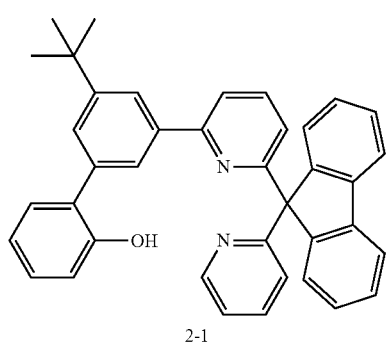

2-1

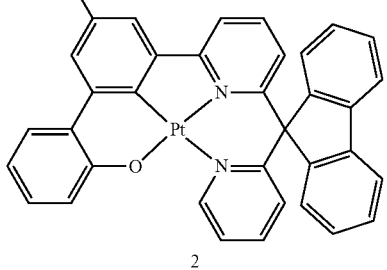

2

Synthesis of Intermediate 2-4

5 grams (g) (32.88 millimoles, mmol) of a (2-methoxyphenyl)boronic acid, 8.5 g (29.31 mmol) of Intermediate 2-5, 10 g (73.27 mmol) of $K_2CO_3$, and 1.7 g (1.46 mmol) $Pd(PPh_3)_4$ were mixed together with 190 milliliters (mL) of THF and 95 mL of $H_2O$, and the mixed solution was heated to a temperature of 80° C. and was stirred under reflux for 16 hours. The obtained reaction solution was cooled to room temperature and extracted by using 400 mL of water and 400 mL of ethyl acetate to obtain an organic layer. The organic layer was dried by using $MgSO_4$, and the residue obtained by evaporating the remaining solvent was separated and purified by using silica gel column chromatography to obtain 6.7 g (72%) of Intermediate 2-4. The obtained compound was identified by LC-MS.

$C_{17}H_{19}BrO$: $M^+$ 318.06

Synthesis of Intermediate 2-3

6.7 g (21.06 mmol) of Intermediate 2-4 and 8 g (31.59 mmol) of bis(pinacolato)diboron, 3.1 g (31.58 mmol) of potassium acetate, and 1 g (1.26 mmol) of $Pd(PPh_3)_2Cl_2$ were mixed together with 100 mL of toluene, and the mixed solution was heated to a temperature of 120° C. and was stirred under reflux for 8 hours. The obtained reaction solution was cooled to room temperature and extracted by using 300 mL of water and 300 mL of ethyl acetate to obtain an organic layer. The organic layer was dried by using $MgSO_4$, and the residue obtained by evaporating the remaining solvent was separated and purified by using silica gel column chromatography to obtain 5.8 g (75%) of Intermediate 2-3. The obtained compound was identified by LC-MS.

$C_{23}H_{31}BO_3$: $M^+$ 366.24

Synthesis of Intermediate 2-2

5.8 g (15.8 mmol) of Intermediate 2-3, 8.3 g (17.4 mmol) of Intermediate A (2-chloro-6-(9-(pyridin-2-yl)-9H-fluoren-9-yl)pyridine), 5.5 g (40 mmol) of $K_2CO_3$, and 1.2 g (1 mmol) of $Pd(PPh_3)_4$ were mixed together with 100 mL of THF and 50 mL of $H_2O$, and the mixed solution was heated to a temperature of 80° C. and was stirred under reflux for 16 hours. The obtained reaction solution was cooled to room temperature and extracted by using 300 mL of water and 300 mL of ethyl acetate to obtain an organic layer. The organic layer was dried by using $MgSO_4$, and the residue obtained by evaporating the remaining solvent was separated and purified by using silica gel column chromatography to obtain 6 g (68%) of Intermediate 2-2. The obtained compound was identified by LC-MS.

$C_{40}H_{34}N_2O$: $M^+$ 558.27

Synthesis of Intermediate 2-1

6 g (10.75 mmol) of Intermediate 2-2 and 35 g (300 mmol) of pyridine hydrochloride were placed into a sealed tube, and the mixed solution was heated to a temperature of 180° C. and was stirred for 16 hours. The obtained reaction solution was cooled to room temperature, and extracted by using a sodium bicarbonate aqueous solution, methylene chloride (MC), and H$_2$O to obtain an organic layer. The organic layer was dried by using MgSO$_4$, and the residue obtained by evaporating the remaining solvent was separated and purified by using silica gel column chromatography to obtain 3.5 g (60%) of Intermediate 2-1. The obtained compound was identified by LC-MS.

C$_{39}$H$_{32}$N$_2$O: M$^+$ 544.25

Synthesis of Compound 2

3.5 g (6.4 mmol) of Intermediate 2-1, 3.2 g (7.7 mmol) of potassium tetrachloroplatinate, and 200 mL of an acetic acid were mixed together with each other, and the mixed solution was heated to a temperature of 120° C. and was stirred under reflux for 16 hours. The obtained reaction solution was cooled to a room temperature, and an extraction process was performed thereon by using a sodium bicarbonate aqueous solution, water, and 300 mL of ethyl acetate to obtain an organic layer. The organic layer was dried by using MgSO$_4$, and the residue obtained by evaporating the remaining solvent was separated and purified by using silica gel column chromatography to obtain 2.6 g (55%) of Compound 2. The obtained compound was identified by LC-MS.

C$_{39}$H$_{30}$N$_2$OPt: M$^+$ 737.20

Synthesis Example 2: Synthesis of Compound 5

Compound 5 was synthesized in the same manner as in Synthesis Example 1, except that 3,5-dibromo-1,1'-biphenyl was used instead of Intermediate 2-5 in synthesizing Intermediate 2-4. The obtained compound was identified by LC-MS.

C$_{41}$H$_{26}$N$_2$OPt: M$^+$ 757.17

Synthesis Example 3: Synthesis of Compound 8

Compound 8 was synthesized in the same manner as in Synthesis Example 1, except that 3,5-dibromo-3',5'-di-tert-butyl-1,1'-biphenyl was used instead of Intermediate 2-5 in synthesizing Intermediate 2-4. The obtained compound was identified by LC-MS.

C$_{49}$H$_{42}$N$_2$OPt: M$^+$ 869.29

Synthesis Example 4: Synthesis of Compound 10

Compound 10 was synthesized in the same manner as in Synthesis Example 1, except that a 5-tert-butyl-2-methoxyphenylboronic acid and 1,3-dibromobenzene were used instead of a (2-methoxyphenyl)boronic acid and Intermediate 2-5 in synthesizing Intermediate 2-4. The obtained compound was identified by LC-MS.

C$_{39}$H$_{30}$N$_2$OPt: M$^+$ 737.20

Synthesis Example 5: Synthesis of Compound 36

36-5

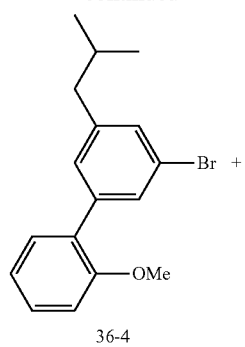

36-4

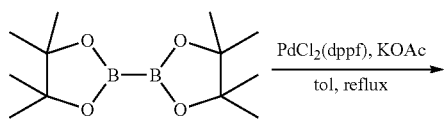

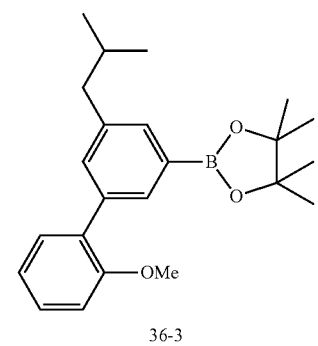

36-3

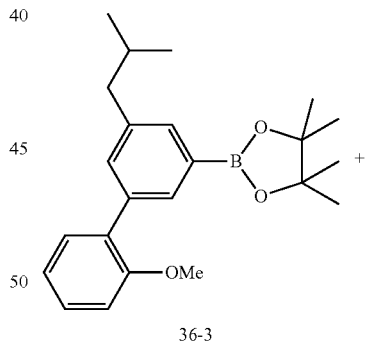

36-3

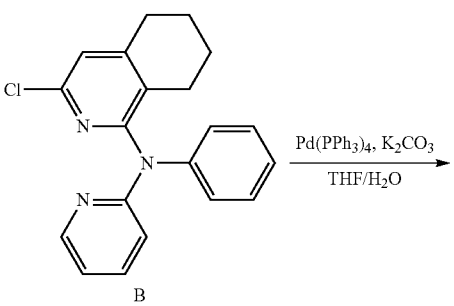

B

-continued

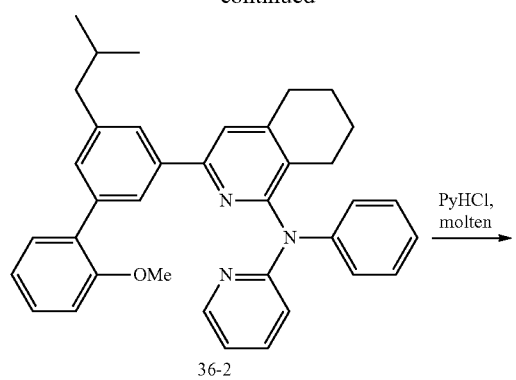

36-2

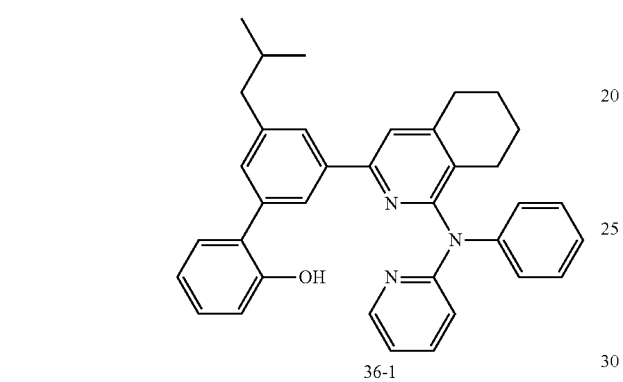

36-1

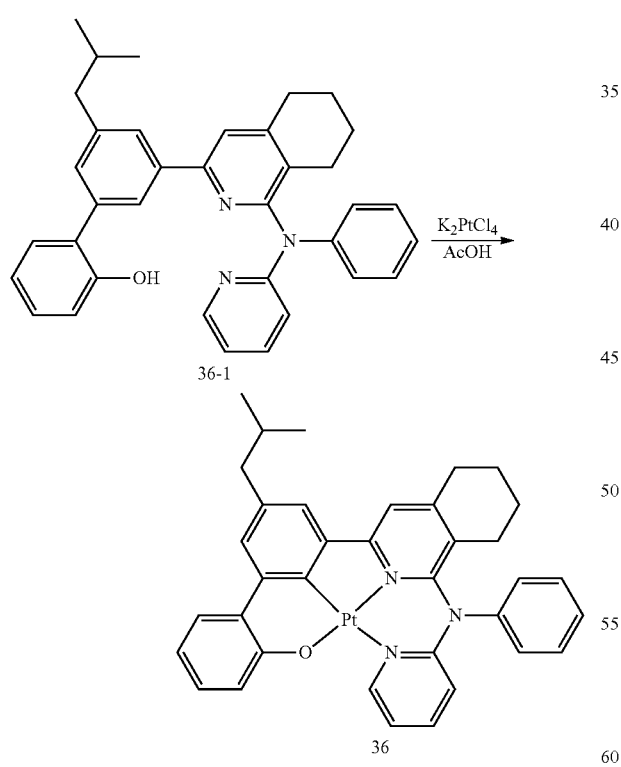

36

Synthesis of Intermediate 36-4

Intermediate 36-4 was synthesized in the same manner as in Synthesis of Intermediate 2-4 in Synthesis Example 1, except that Intermediate 36-5 was used instead of Intermediate 2-5.

Synthesis of Intermediate 36-3

Intermediate 36-3 was synthesized in the same manner as in Synthesis of Intermediate 2-3 in Synthesis Example 1, except that Intermediate 36-4 was used instead of Intermediate 2-4.

Synthesis of Intermediate 36-2

Intermediate 36-2 was synthesized in the same manner as in Synthesis of Intermediate 2-2 in Synthesis Example 1, except that Intermediate 36-3 and Intermediate B were used instead of Intermediate 2-3 and Intermediate A.

Synthesis of Intermediate 36-1

Intermediate 36-1 was synthesized in the same manner as in Synthesis of Intermediate 2-1 in Synthesis Example 1, except that Intermediate 36-2 was used instead of Intermediate 2-2.

Synthesis of Compound 36

Compound 36 was synthesized in the same manner as in Synthesis of Compound 2 in Synthesis Example 1, except that Intermediate 36-1 was used instead of Intermediate 2-1. The obtained compound was identified by LC-MS.

$C_{36}H_{33}N_3OPt$: $M^+$ 718.23

Synthesis Example 6: Synthesis of Compound 44

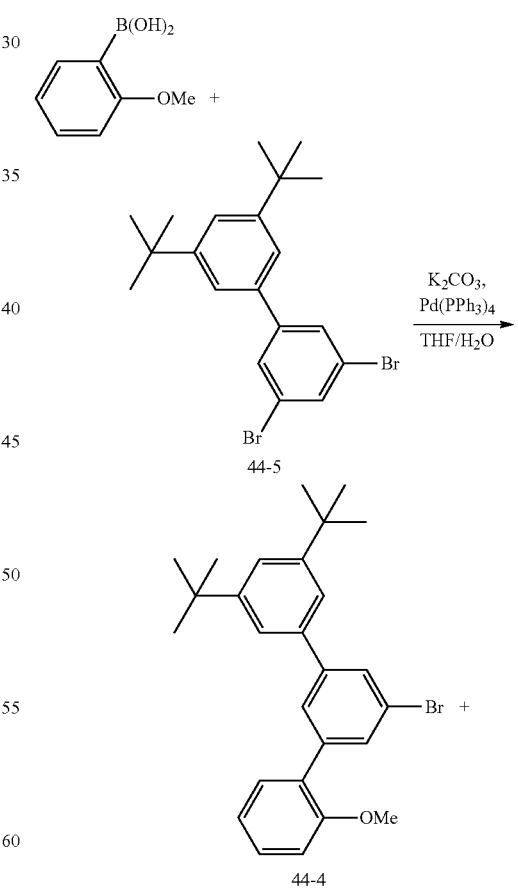

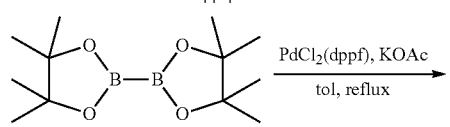

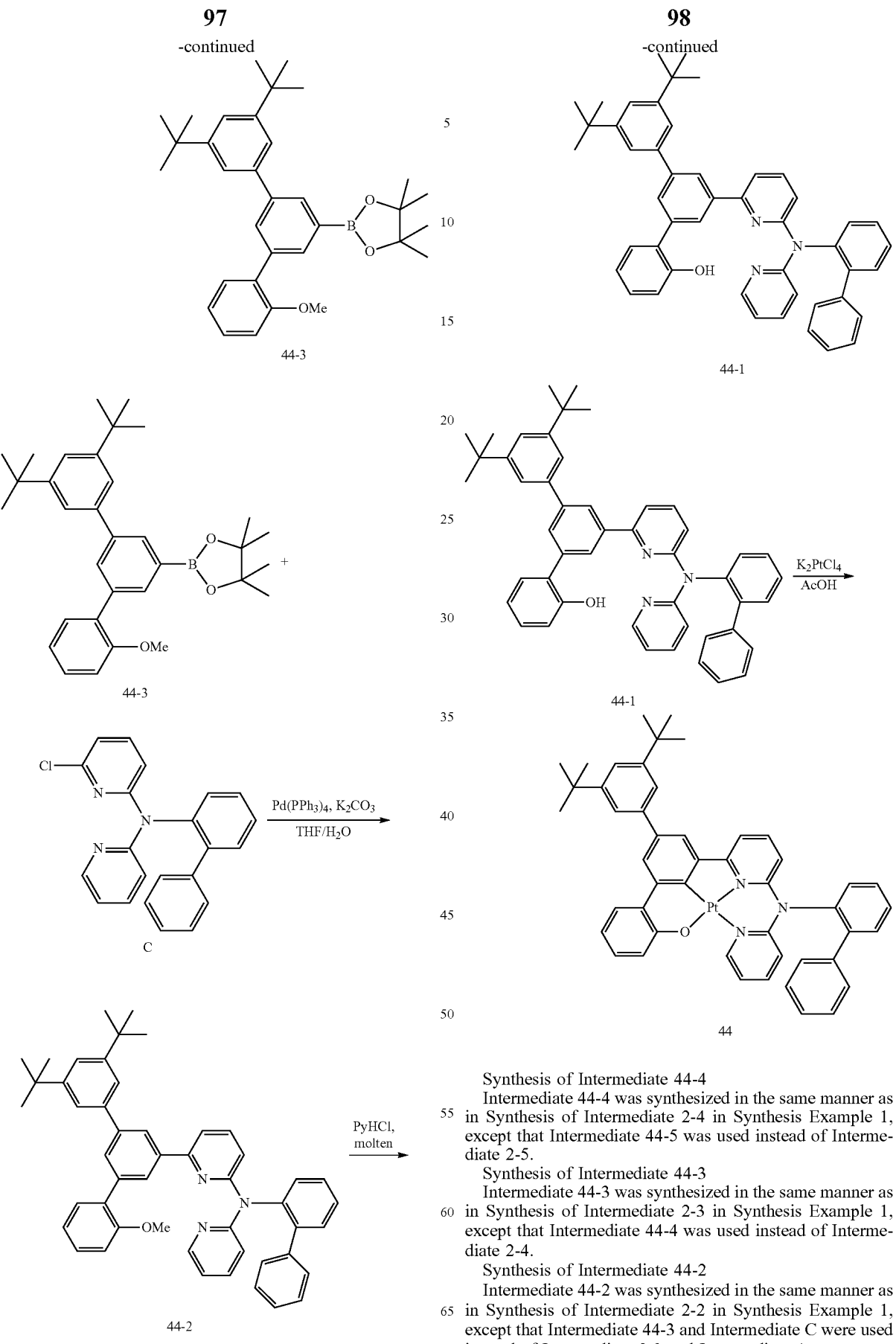

Synthesis of Intermediate 44-4

Intermediate 44-4 was synthesized in the same manner as in Synthesis of Intermediate 2-4 in Synthesis Example 1, except that Intermediate 44-5 was used instead of Intermediate 2-5.

Synthesis of Intermediate 44-3

Intermediate 44-3 was synthesized in the same manner as in Synthesis of Intermediate 2-3 in Synthesis Example 1, except that Intermediate 44-4 was used instead of Intermediate 2-4.

Synthesis of Intermediate 44-2

Intermediate 44-2 was synthesized in the same manner as in Synthesis of Intermediate 2-2 in Synthesis Example 1, except that Intermediate 44-3 and Intermediate C were used instead of Intermediate 2-3 and Intermediate A.

Synthesis of Intermediate 44-1

Intermediate 44-1 was synthesized in the same manner as in Synthesis of Intermediate 2-1 in Synthesis Example 1, except that Intermediate 44-2 was used instead of Intermediate 2-2.

Synthesis of Compound 44

Compound 44 was synthesized in the same manner as in Synthesis of Compound 2 in Synthesis Example 1, except that Intermediate 44-1 was used instead of Intermediate 2-1. The obtained compound was identified by LC-MS.

$C_{48}H_{43}N_3OPt$: M$^+$ 872.31

Synthesis Example 7: Synthesis of Compound 66

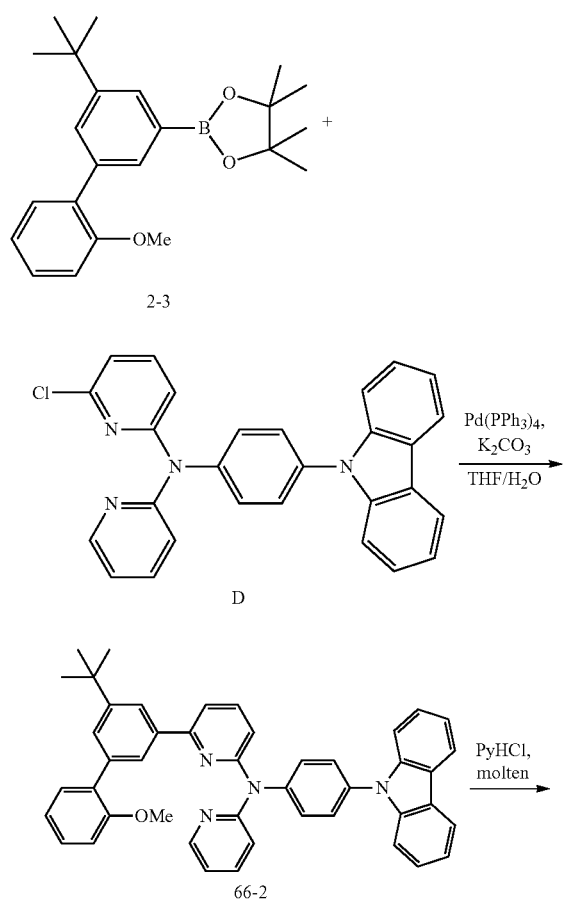

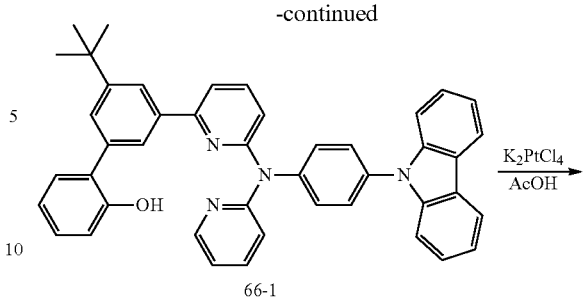

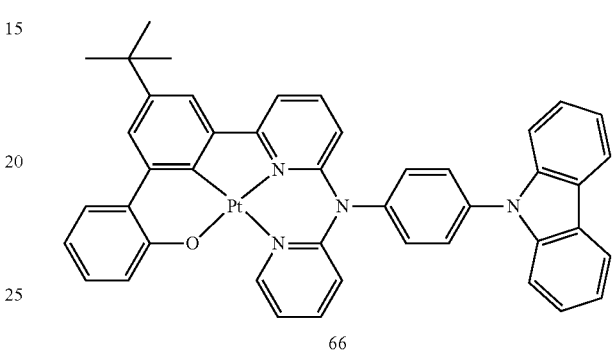

Synthesis of Intermediate 66-2

Intermediate 66-2 was synthesized in the same manner as in Synthesis of Intermediate 2-2 in Synthesis Example 1, except that Intermediate D was used instead of Intermediate A.

Synthesis of Intermediate 66-1

Intermediate 66-1 was synthesized in the same manner as in Synthesis of Intermediate 2-1 in Synthesis Example 1, except that Intermediate 66-2 was used instead of Intermediate 2-2.

Synthesis of Compound 66

Compound 66 was synthesized in the same manner as in Synthesis of Compound 2 in Synthesis Example 1, except that Intermediate 66-1 was used instead of Intermediate 2-1. The obtained compound was identified by LC-MS.

$C_{44}H_{34}N_4OPt$: M$^+$ 829.24

Example 1

An ITO glass substrate, on which an ITO electrode (anode) was deposited, was cut to a size of 50 millimeters (mm)×50 mm×0.5 mm, ultrasonically cleaned using acetone iso-propyl alcohol and pure water each for 15 minutes, and exposed to irradiation of UV light for 30 minutes and ozone to clean.

Then, m-MTDATA was deposited on the ITO electrode (anode) at a deposition rate of 1 Angstroms per second (Å/sec) to form a hole injection layer having a thickness of 600 Angstroms (Å), and α-NPD was deposited on the hole injection layer at a deposition rate of 1 Å/sec to form a hole transport layer having a thickness of 250 Å.

Compound 2 (as a dopant) and CBP (as a host) were respectively co-deposited on the hole transport layer at a deposition rate of 0.1 Å/sec and a deposition rate of 1 Å/sec to form an emission layer having a thickness of 400 Å.

BAlq was deposited on the emission layer at a deposition rate of 1 Å/sec to form a hole blocking layer having a thickness of 50 Å, Alq₃ was deposited on the hole blocking layer to form an electron transport layer having a thickness of 300 Å, LiF was deposited on the electron transport layer to form an electron injection layer having a thickness of 10 Å, and then, Al was vacuum-deposited on the electron injection layer to form a second electrode (cathode) having a thickness of 1,200 Å, thereby completing the manufacture of an organic light-emitting device having a structure of ITO/m-MTDATA (600 Å)/α-NPD (250 Å)/CBP+Compound 2 (10%) (400 Å))/BAlq (50 Å)/Alq₃ (300 Å)/LiF (10 Å)/Al (1,200 Å).

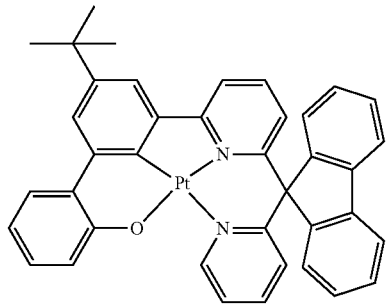

2

Examples 2 to 5 and Comparative Examples 1 and 2

Organic light-emitting devices were manufactured in the same manner as in Example 1, except that compounds shown in Table 2 were used as a dopant, instead of Compound 2 in forming an emission layer.

Evaluation Example 1: Evaluation on Characteristics of Organic Light-Emitting Devices The driving voltage, luminescence efficiency, power efficiency, color purity, quantum efficiency, roll-off ratio, and lifespan ($T_{95}$) of the organic light-emitting devices manufactured in Examples 1 to 5 and Comparative Examples 1 and 2 were evaluated. Results thereof are shown in Table 2. A current-voltage meter (Keithley 2400) and a luminance meter (Minolta Cs-1000A) were used as evaluation devices. The lifespan ($T_{95}$) (at 6,000 nit) was evaluated as a period of time taken until the luminance was reduced to 95% of initial luminance. The roll-off ratio was calculated using Equation 20:

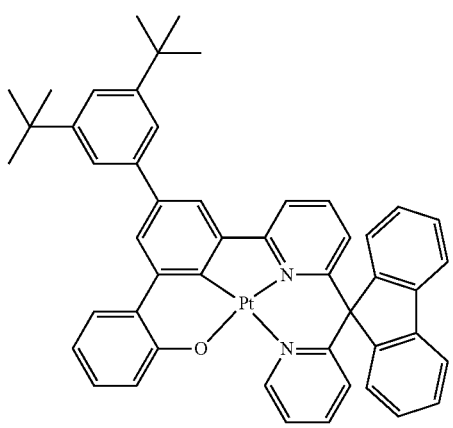

8

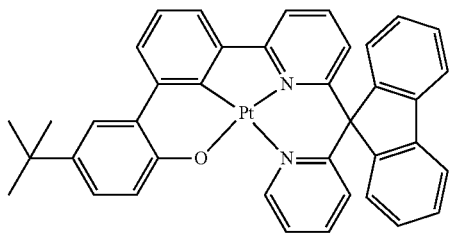

10

Roll-off ratio={1−(efficiency (at 9,000 nit)/maximum emission efficiency)}×100%.  Equation 20

TABLE 2

|  | Dopant | Driving voltage (V) | Luminescence Efficiency (cd/A) | Power Efficiency (lm/W) | CIEx | CIEy | Quantum Efficiency (%) | Roll-off ratio (%) | Lifespan (hr) ($T_{95}$) |
|---|---|---|---|---|---|---|---|---|---|
| Example 1 | Compound 2 | 4.8 | 46.5 | 31.2 | 0.344 | 0.604 | 19 | 21 | 230 |
| Example 2 | Compound 8 | 4.9 | 47.1 | 31.0 | 0.342 | 0.604 | 19 | 20 | 245 |
| Example 3 | Compound 10 | 4.7 | 41.3 | 31.5 | 0.340 | 0.604 | 19 | 10 | 220 |
| Example 4 | Compound 36 | 5.0 | 43.1 | 34.0 | 0.344 | 0.604 | 19 | 18 | 185 |
| Example 5 | Compound 66 | 5.1 | 45.2 | 33.2 | 0.349 | 0.604 | 19 | 20 | 210 |
| Comparative Example 1 | Compound A | 5.2 | 40.2 | 30.1 | 0.344 | 0.604 | 18 | 22 | 180 |
| Comparative Example 2 | Compound B | 6.5 | 35.2 | 20.4 | 0.352 | 0.604 | 18 | 32 | 50 |

-continued

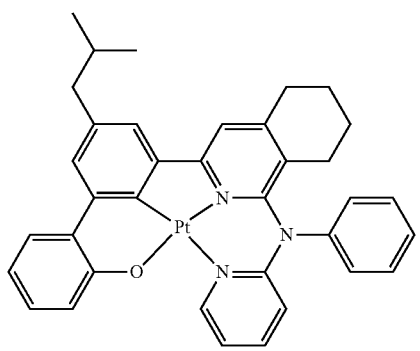

36

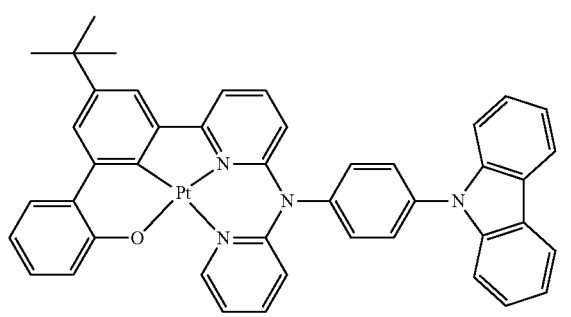

66

Compound A

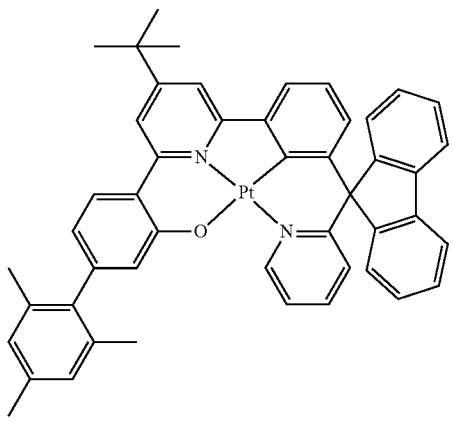

Compound B

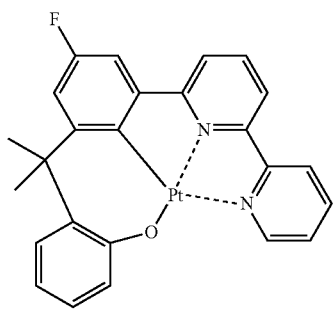

Based on Table 2 results, it was determined that the organic light-emitting devices of Examples 1 to 5 had excellent driving voltage, luminescence efficiency, power efficiency, color purity, quantum efficiency, roll-off ratio, and lifespan characteristics, compared to those of the organic light-emitting devices of Comparative Examples 1 and 2.

The organometallic compound according to embodiments may have excellent electric characteristics and thermal stability. Accordingly, an organic light-emitting device including the organometallic compound may have excellent driving voltage, luminescence efficiency, power efficiency, color purity, and lifespan characteristics. In addition, since the organometallic compound has excellent phosphorescence characteristics, a diagnosis composition having high diagnosis efficiency may be provided by using the organometallic compound.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:

1. An organometallic compound represented by Formula 1:

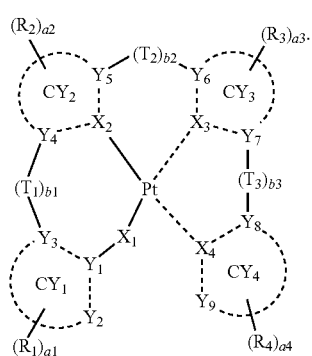

Formula 1 wherein in Formula 1,
$X_1$ is O or S,
$X_2$ is C, and
$X_3$ and $X_4$ are each N,
a bond between Pt and $X_1$ and a bond between Pt and $X_2$ are each a covalent bond, and a bond between Pt and $X_3$ and a bond between Pt and $X_4$ are each a coordinate bond,
$Y_1$ and $Y_3$ to $Y_8$ are each independently C or N,
$Y_2$ and $Y_9$ are each independently C, N, O, or S,
$Y_1$ and $Y_2$ are connected to each other via a single bond or a double bond, $Y_1$ and $Y_3$ are connected to each other via a single bond or a double bond, $X_2$ and $Y_4$ are connected to each other via a single bond or a double bond, $X_2$ and $Y_5$ are connected to each other via a single bond or a double bond, $X_3$ and $Y_6$ are connected to each other via a single bond or a double bond, $X_3$ and $Y_7$ are connected to each other via a single bond or a double bond, $X_4$ and $Y_8$ are connected to each other via a single bond or a double bond, and $X_4$ and $Y_9$ are connected to each other via a single bond or a double bond,
$CY_1$ to $CY_4$ are each independently selected from a $C_5$-$C_{30}$ carbocyclic group and a $C_1$-$C_{30}$ heterocyclic group,
$T_1$ is a single bond,
$T_2$ is selected from a single bond, *—O—*', *—S—*', *—C($R_5$)($R_6$)—*', *—C($R_5$)=C($R_6$)—*', *—C (=O)—*', *—C(=S)—*', *—C≡C—*', *—N(R$_5$)—*', *—Si(R$_5$)(R$_6$)—*', and *—P(R$_5$)(R$_6$)—*', wherein * and *' in each of the foregoing groups independently indicate a binding site to a neighboring atom, T$_3$ is a group selected from *—C(R$_7$)(R$_8$)—*', *—Si(R$_7$)(R$_8$)—*', and *—P(R$_7$)(R$_8$)—*', wherein * and *' in each of the foregoing groups independently indicate a binding site to a neighboring atom, b1 to b3 are 1, R$_5$ and R$_6$ are optionally connected to each other via a first linking group to form a substituted or unsubstituted C$_5$-C$_{30}$ carbocyclic group or a substituted or unsubstituted C$_1$-C$_{30}$ heterocyclic group, R$_1$ to R$_6$ and R$_9$ to R$_{10}$ are each independently selected from hydrogen, deuterium, —F, —Cl, —Br, —I, —SF$_5$, a hydroxy group, a cyano group, a nitro group, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), —B(Q$_6$)(Q$_7$), and —P(=O)(Q$_8$)(Q$_9$), a1 to a4 are each independently 0, 1, 2, 3, 4, or 5, two groups selected from groups R$_1$ in the number of a1 are optionally connected to each other to form a substituted or unsubstituted C$_5$-C$_{30}$ carbocyclic group or a substituted or unsubstituted C$_1$-C$_{30}$ heterocyclic group, two groups selected from groups R$_2$ in the number of a2 are optionally connected to each other to form a substituted or unsubstituted C$_5$-C$_{30}$ carbocyclic group or a substituted or unsubstituted C$_1$-C$_{30}$ heterocyclic group, two group selected from groups R$_3$ in the number of a3 are optionally connected to each other to form a substituted or unsubstituted C$_5$-C$_{30}$ carbocyclic group or a substituted or unsubstituted C$_1$-C$_{30}$ heterocyclic group, two groups selected from groups R$_4$ in the number of a4 are optionally connected to each other to form a substituted or unsubstituted C$_5$-C$_{30}$ carbocyclic group or a substituted or unsubstituted C$_1$-C$_{30}$ heterocyclic group, two or more neighboring groups selected from R$_1$ to R$_4$ are optionally connected to each other to form a substituted or unsubstituted C$_5$-C$_{30}$ carbocyclic group or a substituted or unsubstituted C$_1$-C$_{30}$ heterocyclic group, R$_7$ and R$_8$ are each independently selected from a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, and a substituted or unsubstituted monovalent non-aromatic condensed heteropolycyclic group, R$_7$ and R$_8$ are connected to each other via a second linking group, the second linking group is selected from a single bond, *—O—*', *—S—*', *—C(R$_{10}$)(R$_{10}$)—*', *—C(R$_{10}$)=C(R$_{10}$)—*', *—C(=O)—*', *—C(=S)—*', *—N(R$_{10}$)—*', *—Si(R$_{10}$)(R$_{10}$)—*', and *—P(R$_{10}$)(R$_{10}$)—*', wherein * and *' in each of the foregoing groups independently indicate a binding site to a neighboring atom, at least one substituent selected from a substituent(s) of the substituted C$_5$-C$_{30}$ carbocyclic group, the substituted C$_1$-C$_{30}$ heterocyclic group, the substituted C$_1$-C$_{60}$ alkyl group, the substituted C$_2$-C$_{60}$ alkenyl group, the substituted C$_2$-C$_{60}$ alkynyl group, the substituted C$_1$-C$_{60}$ alkoxy group, the substituted C$_3$-C$_{10}$ cycloalkyl group, the substituted C$_1$-C$_{10}$ heterocycloalkyl group, the substituted C$_3$-C$_{10}$ cycloalkenyl group, the substituted C$_1$-C$_{10}$ heterocycloalkenyl group, the substituted C$_6$-C$_{60}$ aryl group, the substituted C$_6$-C$_{60}$ aryloxy group, the substituted C$_6$-C$_{60}$ arylthio group, the substituted C$_1$-C$_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, —CD$_3$, —CD$_2$H, —CDH$_2$, —CF$_3$, —CF$_2$H, —CFH$_2$, a hydroxy group, a cyano group, a nitro group, a C$_1$-C$_{60}$ alkyl group, a C$_2$-C$_{60}$ alkenyl group, a C$_2$-C$_{60}$ alkynyl group, and a C$_1$-C$_{60}$ alkoxy group;

a C$_1$-C$_{60}$ alkyl group, a C$_2$-C$_{60}$ alkenyl group, a C$_2$-C$_{60}$ alkynyl group, and a C$_1$-C$_{60}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxy group, a cyano group, a nitro group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —N(Q$_{11}$)(Q$_{12}$), —Si(Q$_{13}$)(Q$_{14}$)(Q$_{15}$), —B(Q$_{16}$)(Q$_{17}$), and —P(=O)(Q$_{18}$)(Q$_{19}$);

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group;

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxy group, a cyano group, a nitro group, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), and wherein $Q_1$ to $Q_9$, $Q_{11}$ to $Q_{19}$, $Q_{21}$ to $Q_{29}$, and $Q_{31}$ to $Q_{39}$ are each independently selected from hydrogen, deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

2. The organometallic compound of claim 1, wherein $R_1$ to $R_6$ are each independently selected from:

hydrogen, deuterium, —F, —Cl, —Br, —I, a hydroxy group, a cyano group, a nitro group, —$SF_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxy group, a cyano group, a nitro group, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxy group, a cyano group, a nitro group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —N($Q_1$)($Q_2$), —Si($Q_3$)($Q_4$)($Q_5$), —B($Q_6$)($Q_7$), and —P(=O)($Q_8$)($Q_9$), wherein $Q_1$ to $Q_9$ are each independently selected from:
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

3. The organometallic compound of claim 1, wherein $R_1$ to $R_6$ are each independently selected from:

hydrogen, deuterium, —F, a cyano group, a nitro group, —$SF_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group; and —$N(Q_1)(Q_2)$, —$Si(Q_3)(Q_4)(Q_5)$, —$B(Q_6)(Q_7)$, and —$P(=O)(Q_8)(Q_9)$, wherein $Q_1$ to $Q_9$ are each independently selected from: —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

4. The organometallic compound of claim 1, wherein $R_1$ to $R_6$ are each independently selected from hydrogen, deuterium, —F, a cyano group, a nitro group, —$SF_5$, —$CH_3$, —$CD_3$, —$CD_2H$, —$CDH_2$, —$CF_3$, —$CF_2H$, —$CFH_2$, groups represented by Formulae 9-1 to 9-19, groups represented by Formulae 10-1 to 10-46, and —$Si(Q_3)(Q_4)(Q_5)$:

Formula 9-1

Formula 9-2

Formula 9-3

Formula 9-4

Formula 9-5

Formula 9-6

Formula 9-7

Formula 9-8

Formula 9-9

Formula 9-10

Formula 9-11

Formula 9-12

Formula 9-13

Formula 9-14

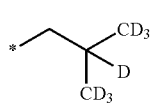
Formula 9-15
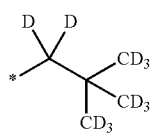
Formula 9-16
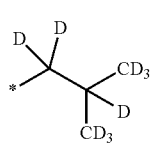
Formula 9-17
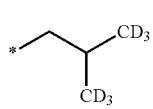
Formula 9-18
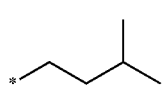
Formula 9-19
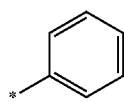
Formula 10-1
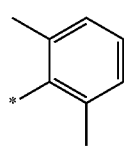
Formula 10-2
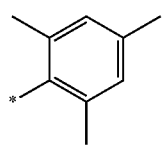
Formula 10-3
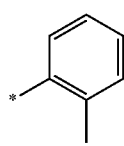
Formula 10-4
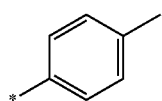
Formula 10-5
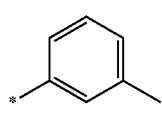
Formula 10-6
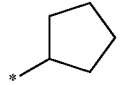
Formula 10-7
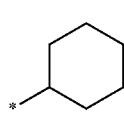
Formula 10-8
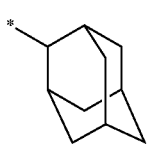
Formula 10-9
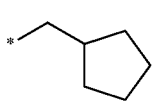
Formula 10-10
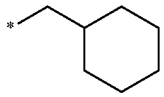
Formula 10-11
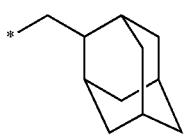
Formula 10-12
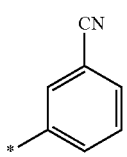
Formula 10-13
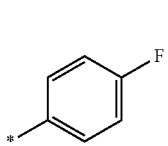
Formula 10-14
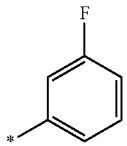
Formula 10-15
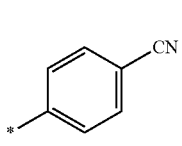
Formula 10-16
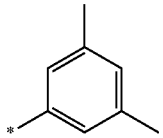
Formula 10-17
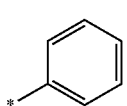
Formula 10-18
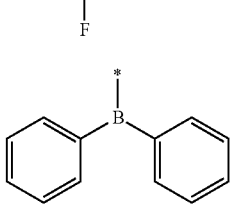
Formula 10-19

-continued
Formula 10-20
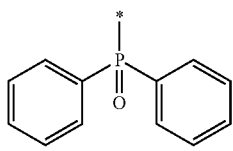
Formula 10-21
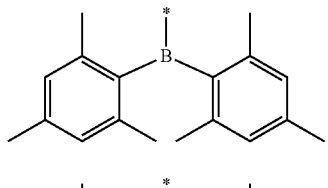
Formula 10-22
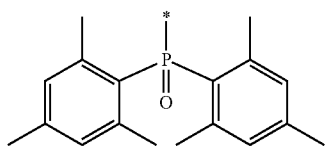
Formula 10-23
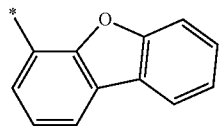
Formula 10-24
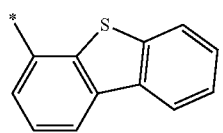
Formula 10-25
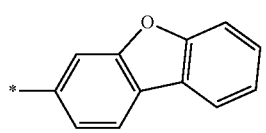
Formula 10-26
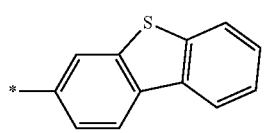
Formula 10-27
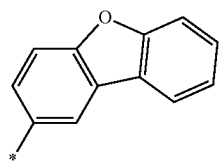
Formula 10-28
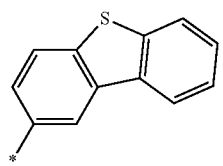
Formula 10-29
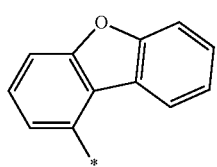
Formula 10-30
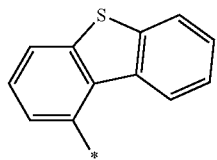
Formula 10-31
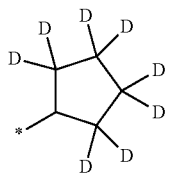
Formula 10-32
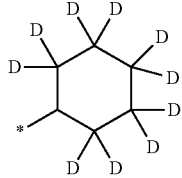
Formula 10-33
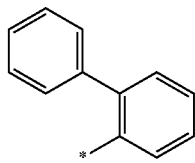
Formula 10-34
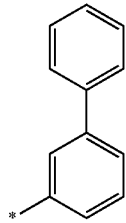
Formula 10-35
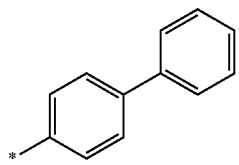
Formula 10-36
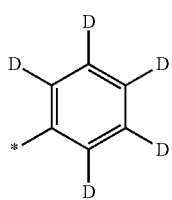
Formula 10-37
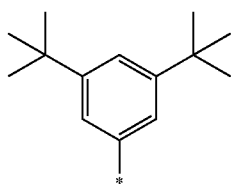

-continued

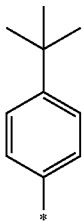

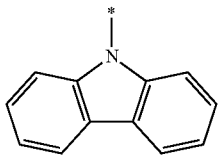

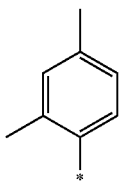

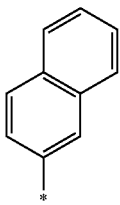

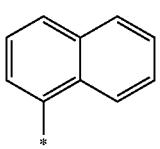

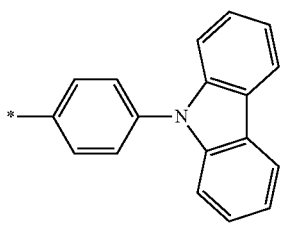

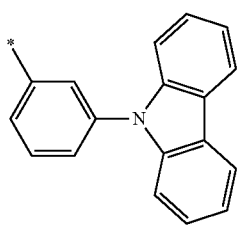

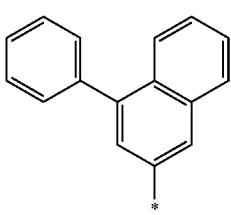

Formula 10-38

Formula 10-39

Formula 10-40

Formula 10-41

Formula 10-42

Formula 10-43

Formula 10-44

Formula 10-45

-continued

Formula 10-46

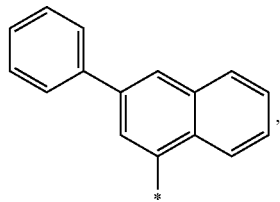

wherein in Formulae 9-1 to 9-19 and 10-1 to 10-46,
* indicates a binding site to a neighboring atom.

5. An organometallic compound represented by Formula 1-1A:

Formula 1-1A

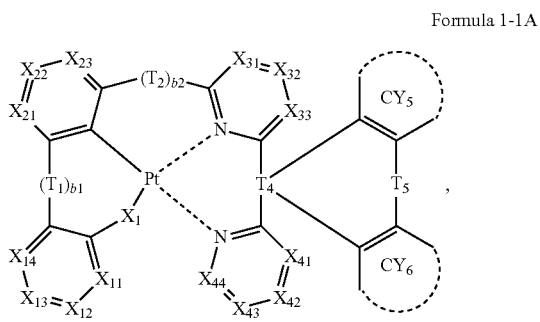

wherein in Formula 1-1 Å, $X_1$ is O or S, $T_1$ is a single bond, $T_2$ is selected from a single bond, *—O—*', *—S—*', *—C($R_5$)($R_6$)—*', *—C($R_5$)=C($R_6$)—*', *—C(=O)—*', *—C(=S)—*', *—C≡C—*', *—N($R_5$)—*', *—Si($R_5$)($R_6$)—*', and *—P($R_5$)($R_6$)—*', wherein * and *' in each of the foregoing groups independently indicate a binding site to a neighboring atom, b1 to b2 are 1, $X_{11}$ is N or C($R_{11}$), $X_{12}$ is N or C($R_{12}$), $X_{13}$ is N or C($R_{13}$), $X_{14}$ is N or C($R_{14}$), $X_{21}$ is N or C($R_{21}$), $X_{22}$ is N or C($R_{22}$), $X_{23}$ is N or C($R_{23}$), $X_{31}$ is N or C($R_{31}$), $X_{32}$ is N or C($R_{32}$), $X_{33}$ is N or C($R_{33}$), $X_{41}$ is N or C($R_{41}$), $X_{42}$ is N or C($R_{42}$), $X_{43}$ is N or C($R_{43}$), and $X_{44}$ is N or C($R_{44}$), $R_{11}$ to $R_{14}$, $R_{21}$ to $R_{23}$, $R_{31}$ to $R_{33}$, and $R_{41}$ to $R_{44}$ are each independently selected from hydrogen, deuterium, —F, —Cl, —Br, —I, —$SF_5$, a hydroxy group, a cyano group, a nitro group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), and —P(=O)($Q_8$)($Q_9$), two groups selected from $R_{11}$ to $R_{14}$ are optionally connected to each other to form a substituted or unsubstituted $C_5$-$C_{30}$ carbocyclic group or a substituted or unsubstituted $C_1$-$C_{30}$ heterocyclic group, two groups selected from $R_{21}$ to $R_{23}$ are optionally connected to each other to form a substituted or unsubstituted $C_5$-$C_{30}$ carbocyclic group or a substituted or unsubstituted $C_1$-$C_{30}$ heterocyclic group, two groups selected from $R_{31}$ to $R_{33}$ are optionally connected to each other to form a substituted or unsubstituted $C_5$-$C_{30}$ carbocyclic group or a substituted or unsubstituted $C_1$-$C_{30}$ heterocyclic group, two groups selected from $R_{11}$ to $R_{44}$ are optionally connected to each other to form a substituted or unsubstituted $C_5$-$C_{30}$ carbocyclic group or a substituted or unsubstituted $C_1$-$C_{30}$ heterocyclic group, two groups selected from $R_{11}$ to $R_{14}$, $R_{21}$ to $R_{23}$, $R_{31}$ to $R_{33}$, and $R_{41}$ to $R_{44}$ are optionally connected to each other to form a substituted or unsubstituted $C_5$-$C_{30}$ carbocyclic group or a substituted or unsubstituted $C_1$-$C_{30}$ heterocyclic group, $T_4$ is C, Si, or P, $T_5$ is a group selected from a single bond, *—O—*', *—S—*', *—C($R_9$)($R_{10}$)—*', *—C($R_9$)=C($R_{10}$)—*', *—C(=O)—*', *—C(=S)—*', *—N($R_9$)—*', *—Si($R_9$)($R_{10}$)—*', and *—P($R_9$)($R_{10}$)—*', wherein * and *' in each of the foregoing groups independently indicate a binding site to a neighboring atom, $R_9$ and $R_{10}$ are each independently the same as $R_{11}$, and $CY_5$ and $CY_6$ are each independently selected from:

a cyclopentane group, a cyclohexane group, a cycloheptane group, a benzene group, a naphthalene group, a fluorene group, a phenanthrene group, an anthracene group, a triphenylene group, a pyrene group, a chrysene group, a pyridine group, a pyrimidine group, a quinoline group, an isoquinoline group, a quinazoline group, and a quinoxaline group; and a cyclopentane group, a cyclohexane group, a cycloheptane group, a benzene group, a naphthalene group, a fluorene group, a phenanthrene group, an anthracene group, a triphenylene group, a pyrene group, a chrysene group, a pyridine group, a pyrimidine group, a quinoline group, an isoquinoline group, a quinazoline group, and a quinoxaline group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxy group, a cyano group, a nitro group, a $C_1$-$C_{10}$ alkyl group, a cyclopentyl group, a cyclohexyl group, a cycloheptyl group, a phenyl group, a naphthyl group, a pyridinyl group, and a pyrimidinyl group.

6. An organometallic compound selected from Compounds 1 to 78 below:

1

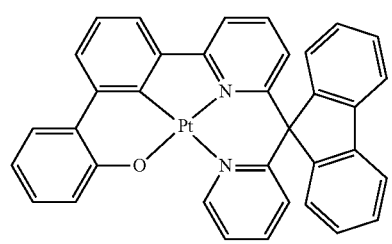

2

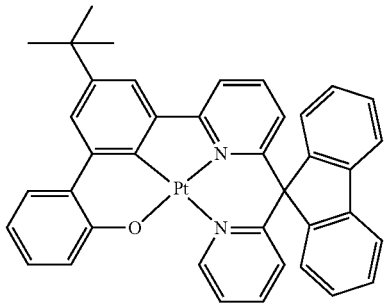

3

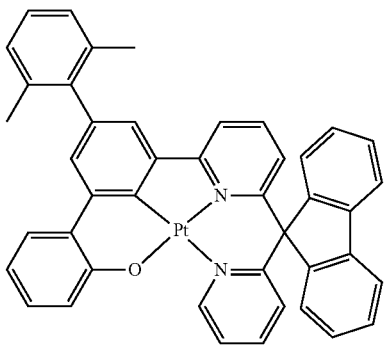

4

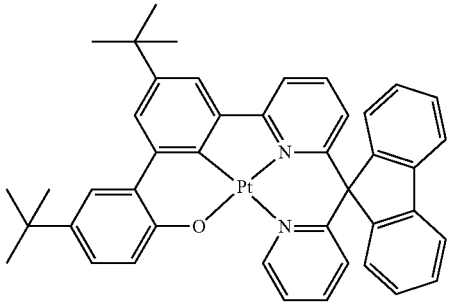

5

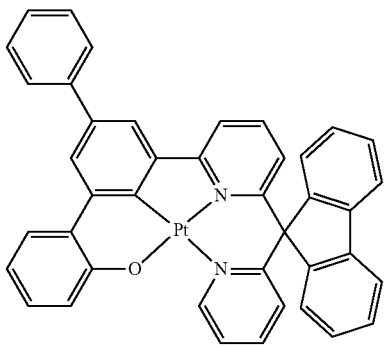

6

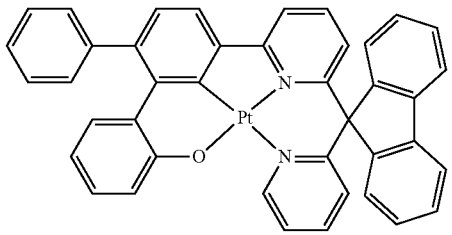

119
-continued
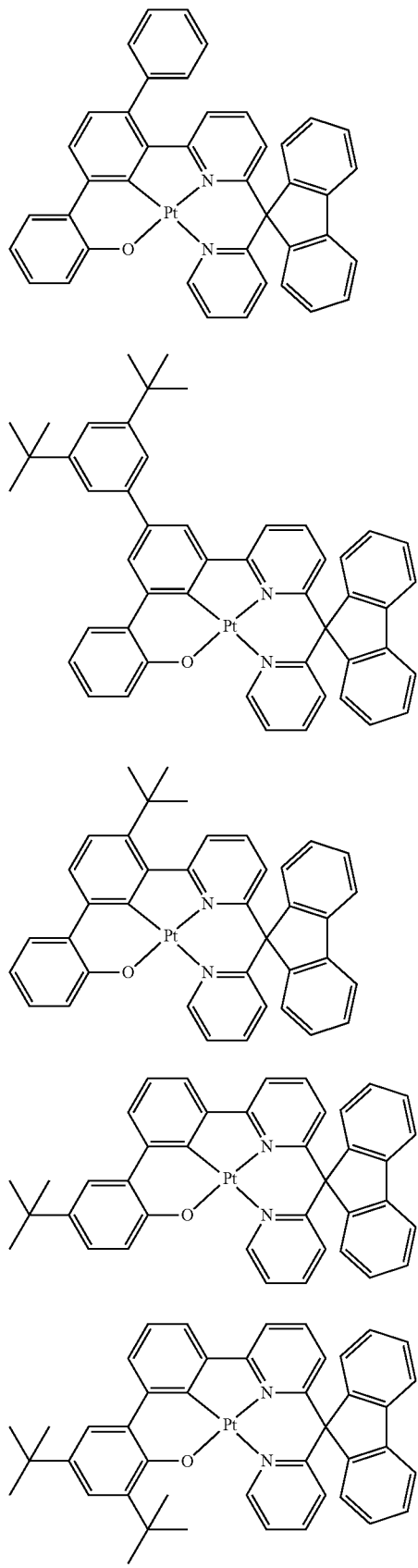
120
-continued
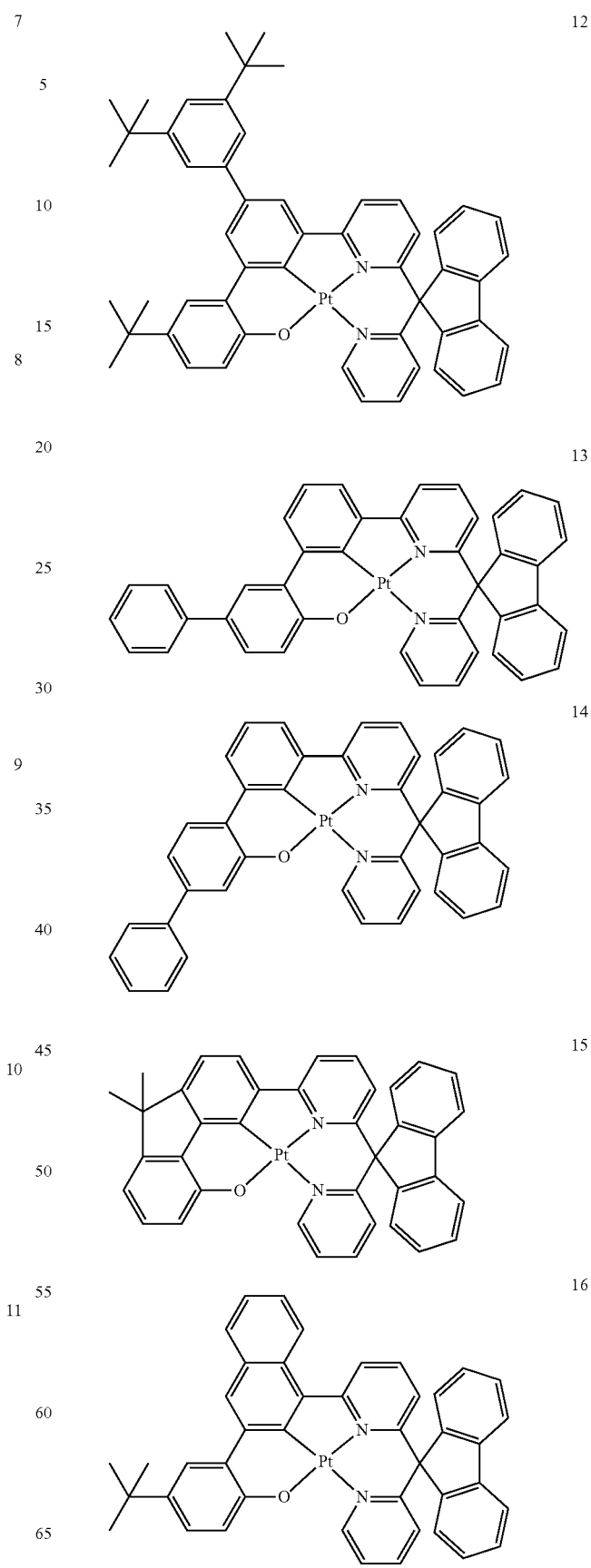

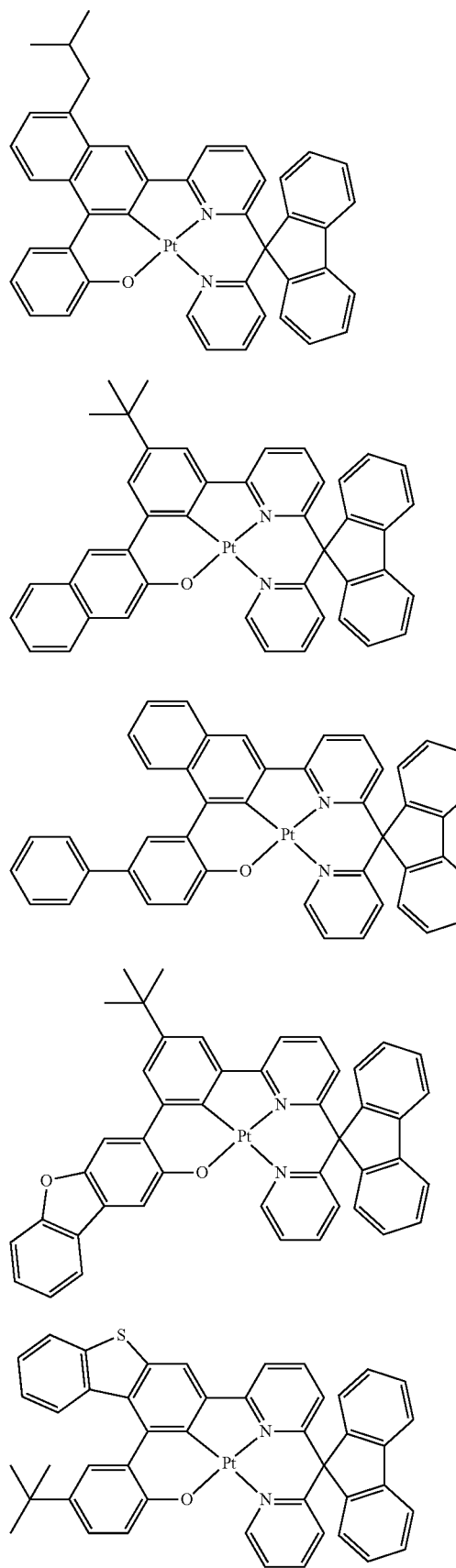
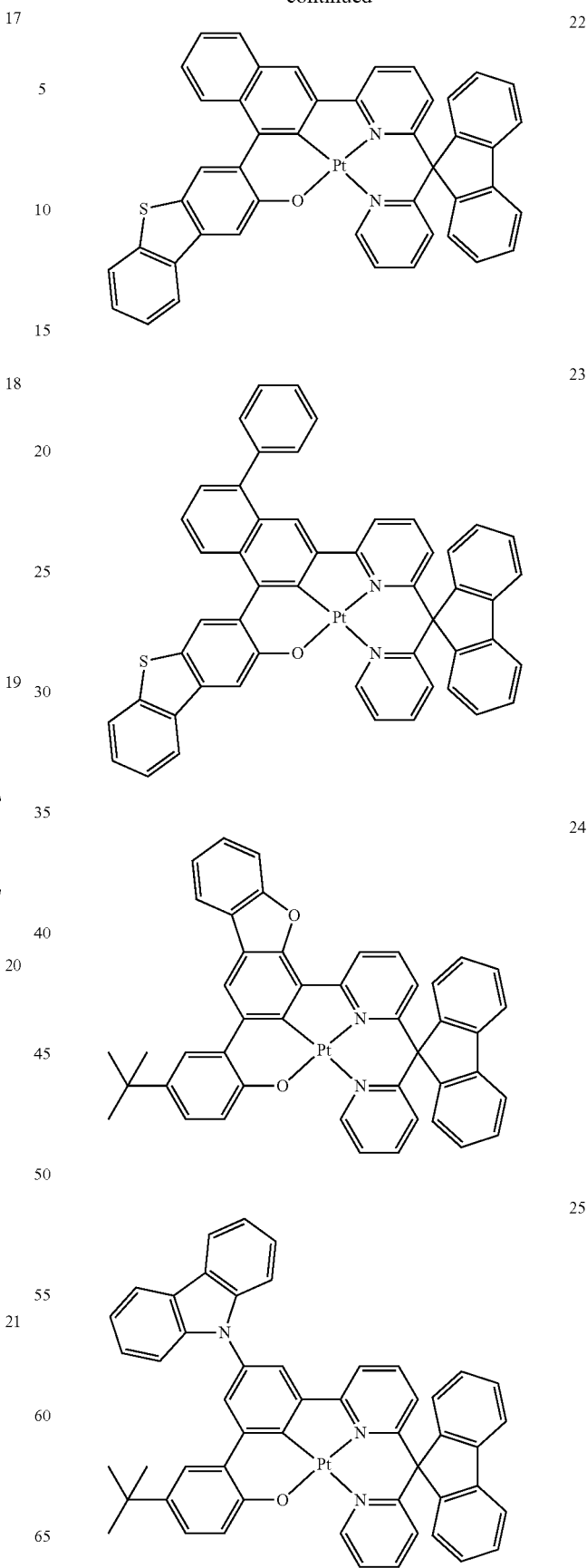

26
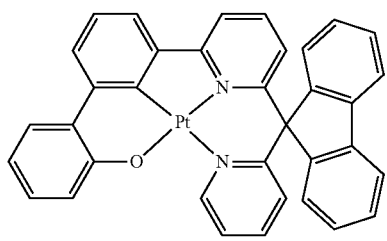
27
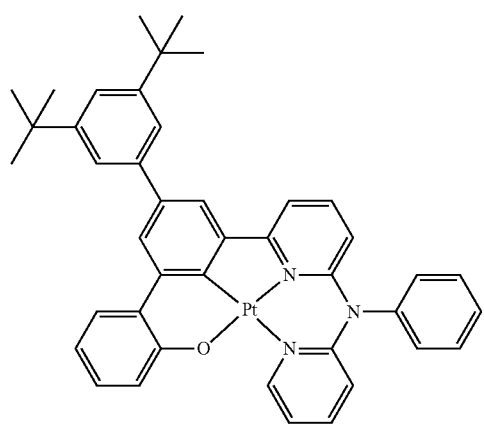
28
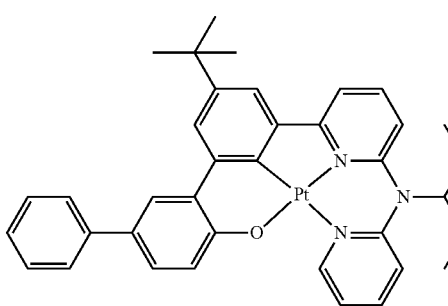
29
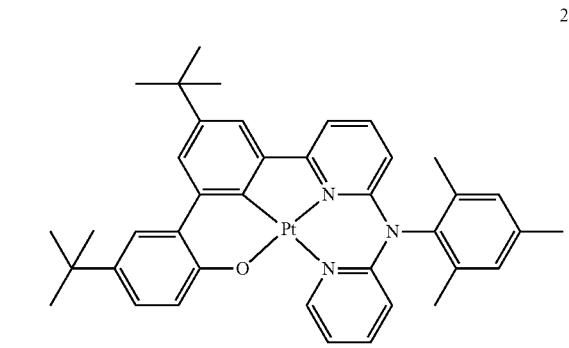
30
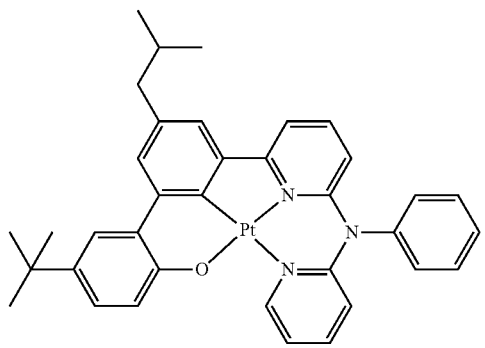
31
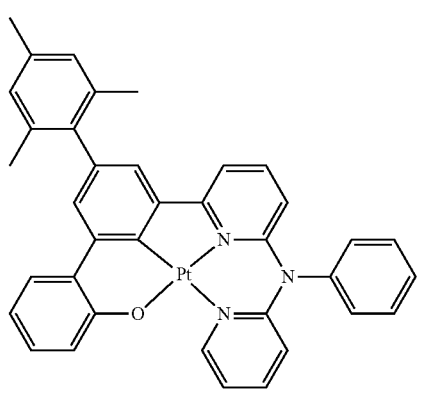
32
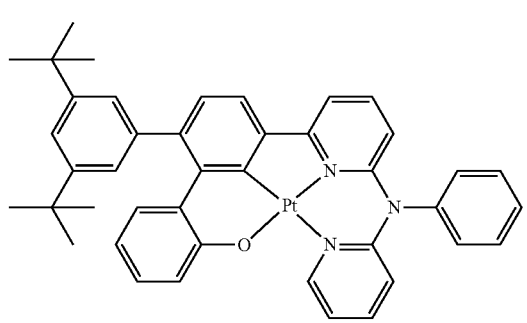
33
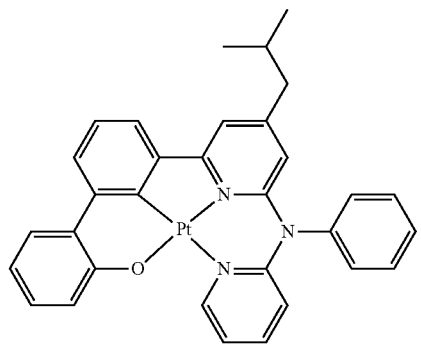

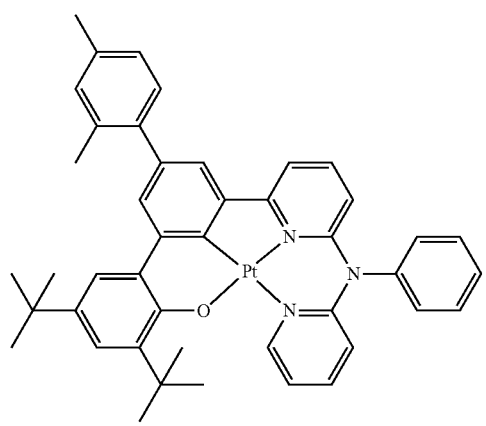
34
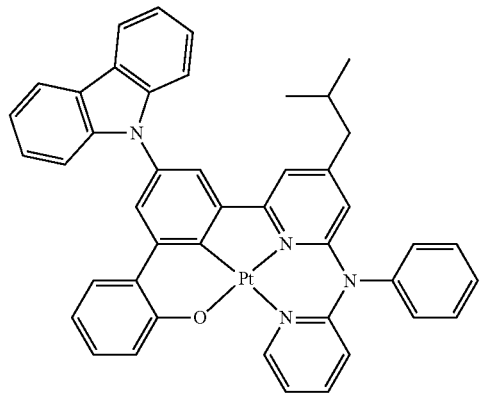
38
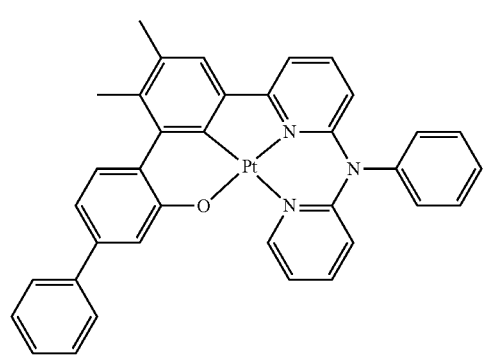
35
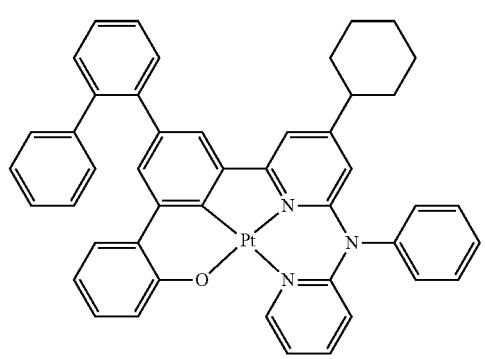
39
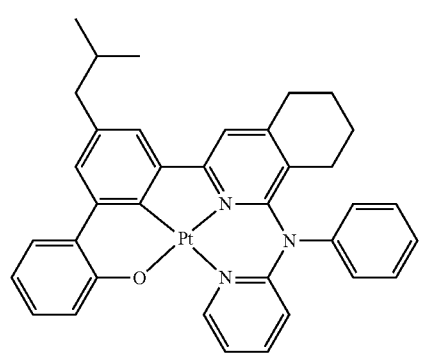
36
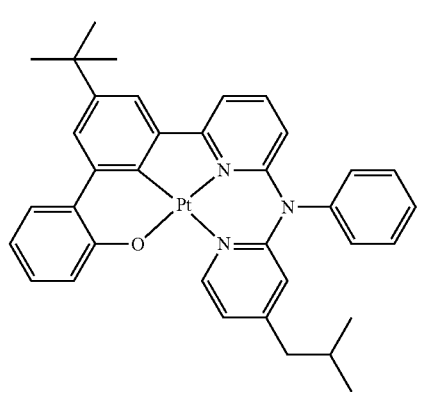
40
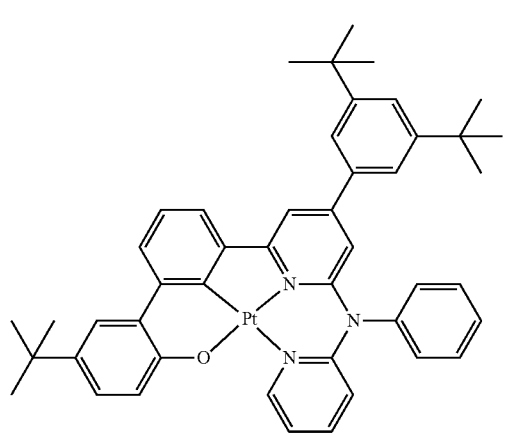
37
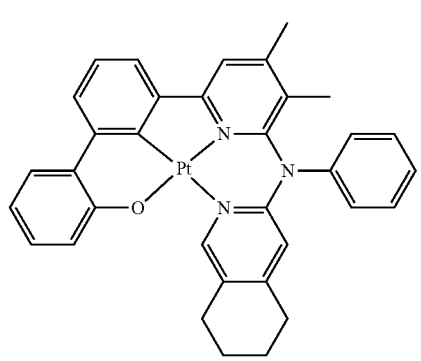
41

42
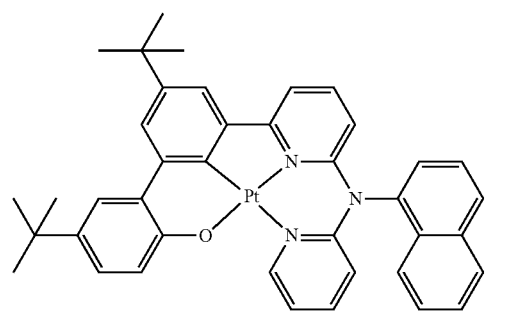
43
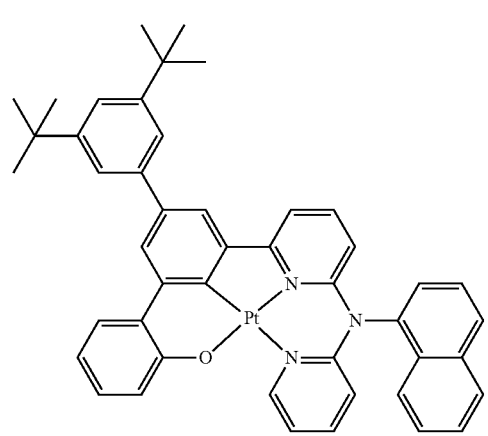
44
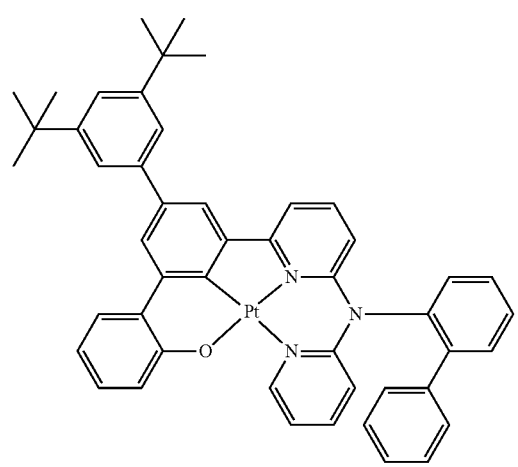
45
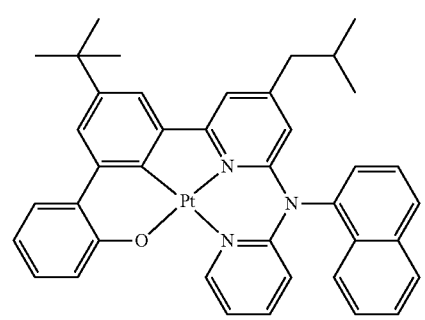
46
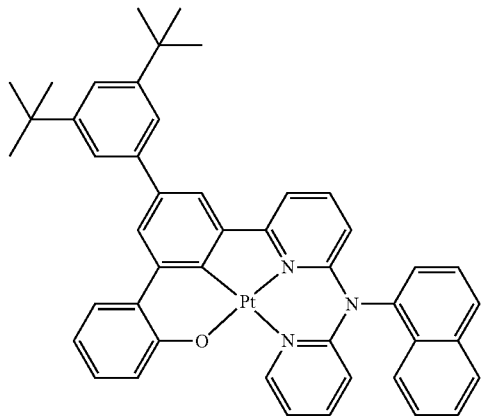
47
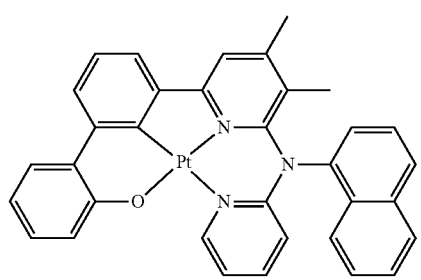
48
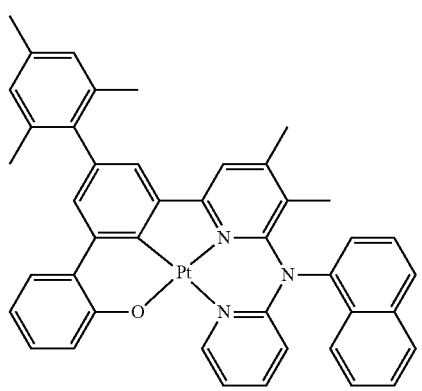
49
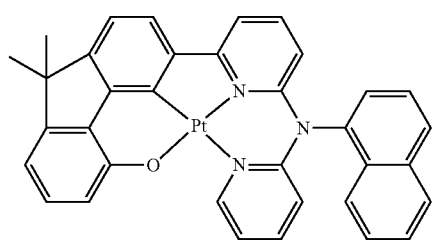
50
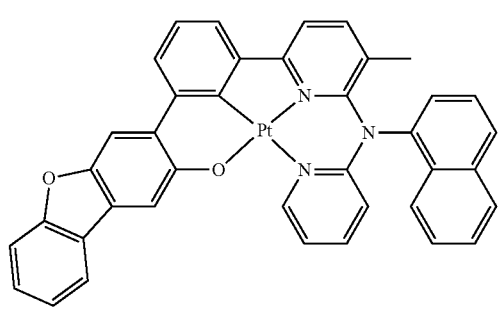

51
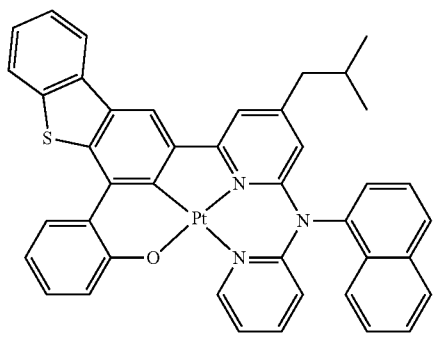
52
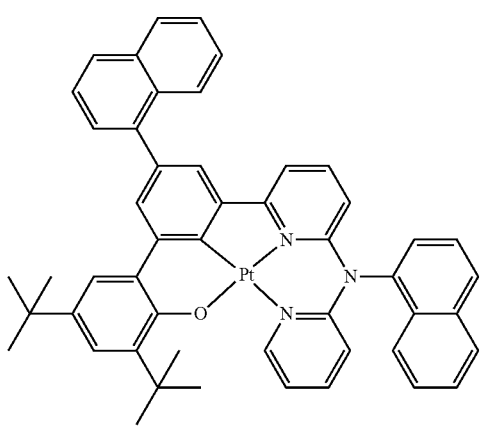
53
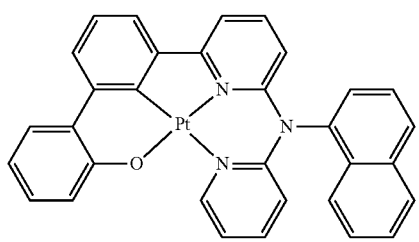
54
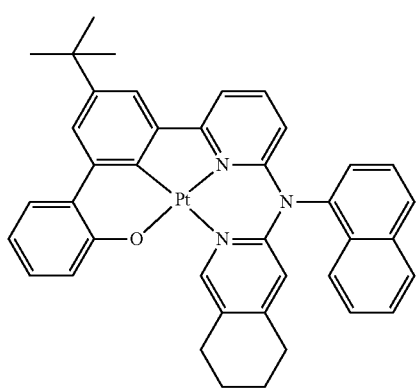
55
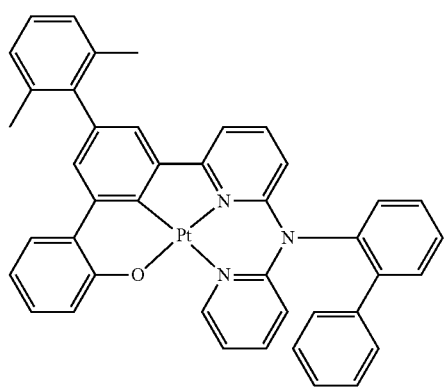
56
57

131
-continued
58
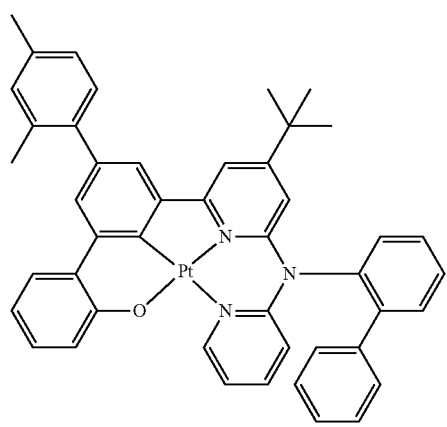
59
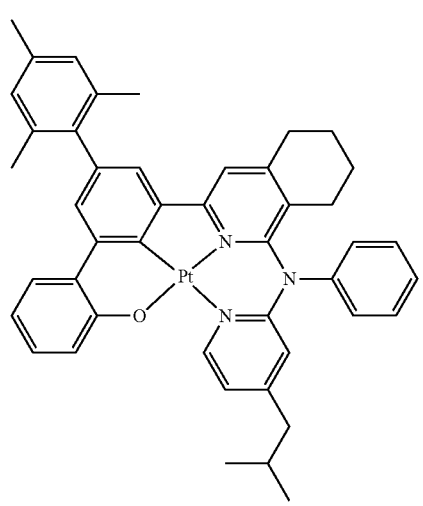
60
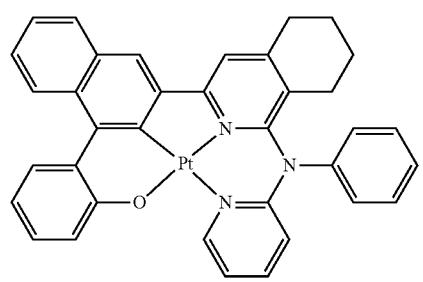
61
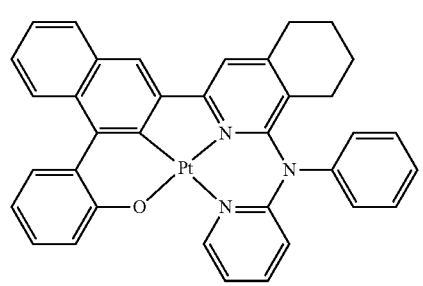
132
-continued
62
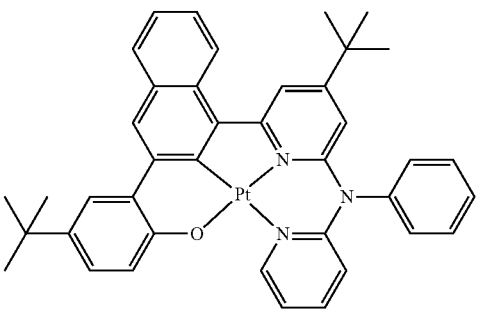
63
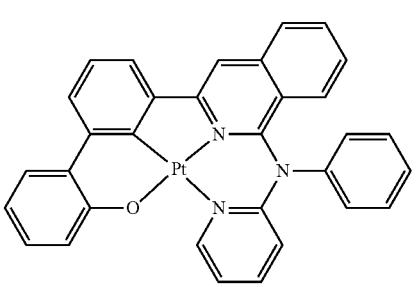
64
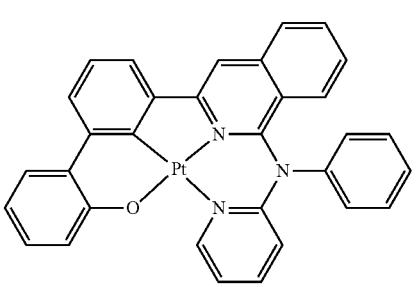
65
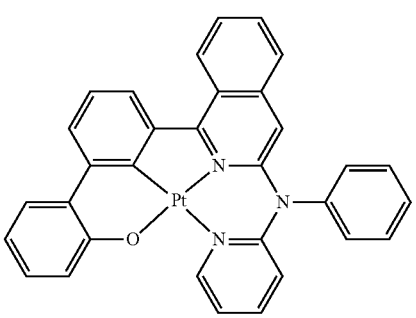
66
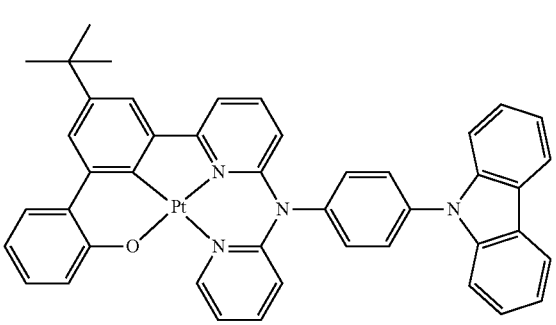

67
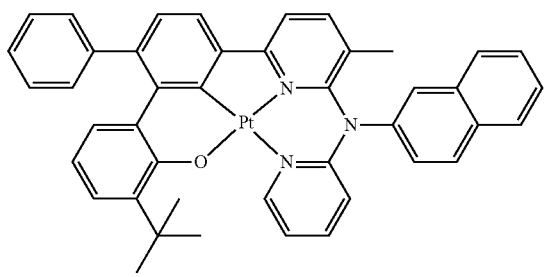
68
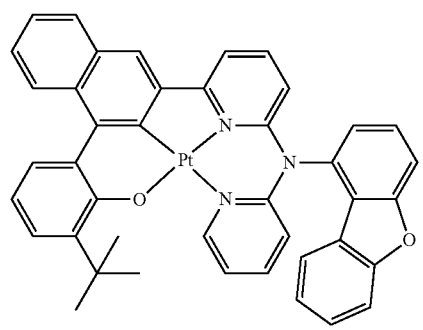
69
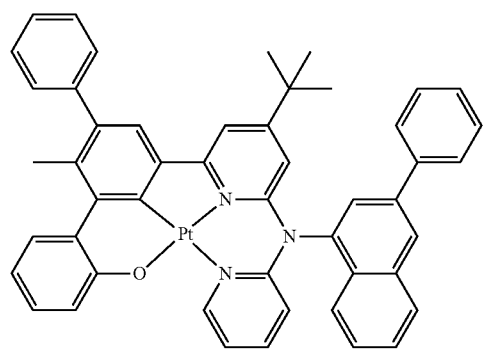
70
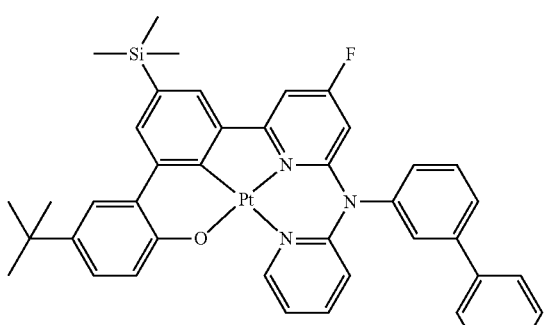
71
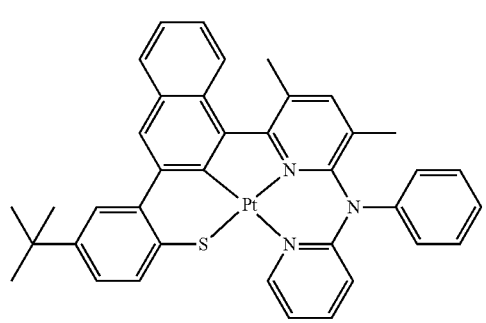
72
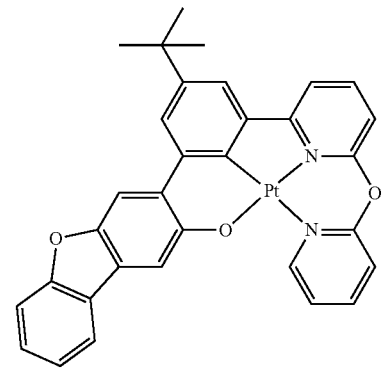
73
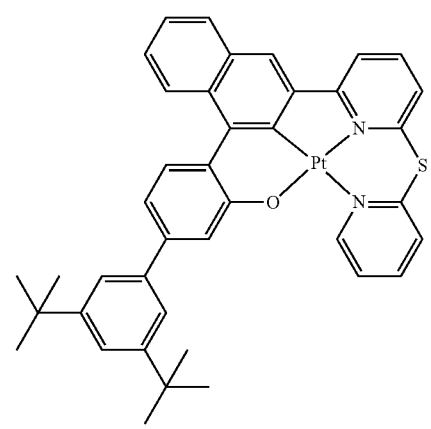
74
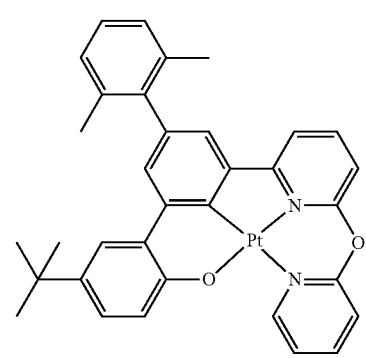
75
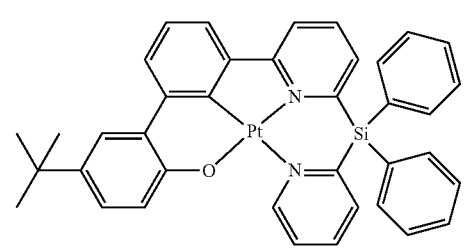

-continued

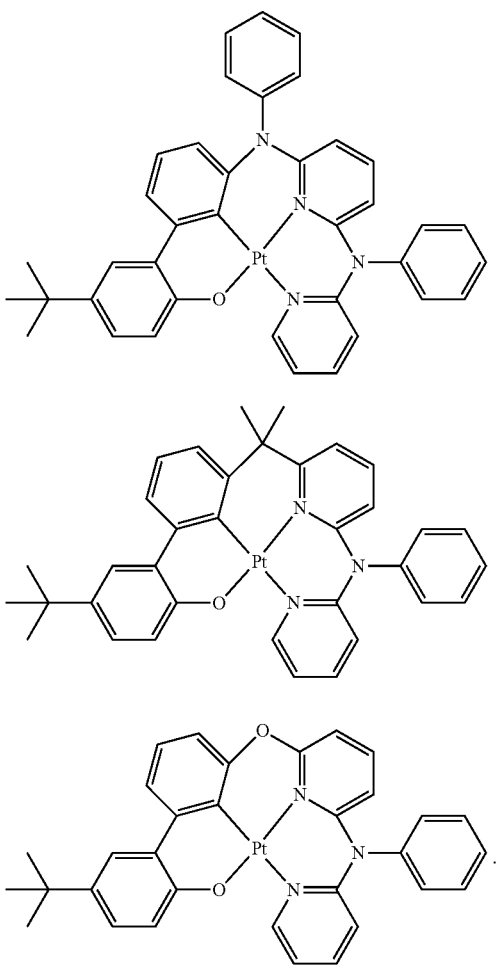

7. An organic light-emitting device comprising:
a first electrode;
a second electrode; and
an organic layer disposed between the first electrode and the second electrode,
wherein the organic layer comprises an emission layer, and
wherein the organic layer comprises at least one organometallic compound of claim 1.

8. The organic light-emitting device of claim 7, wherein
the first electrode is an anode,
the second electrode is a cathode,
the organic layer further comprises a hole transport region disposed between the first electrode and the emission layer, and an electron transport region disposed between the emission layer and the second electrode,
the hole transport region comprises a hole injection layer, a hole transport layer, an electron blocking layer, or any combination thereof, and
the electron transport region comprises a hole blocking layer, an electron transport layer, an electron injection layer, or any combination thereof.

9. The organic light-emitting device of claim 7, wherein the emission layer comprises the organometallic compound.

10. The organic light-emitting device of claim 9, wherein the emission layer further comprises a host, and
an amount of the host is greater than an amount of the organometallic compound.

11. A diagnosis composition comprising at least one organometallic compound of claim 1.

* * * * *